US010032989B2

(12) United States Patent
Pfister et al.

(10) Patent No.: US 10,032,989 B2
(45) Date of Patent: Jul. 24, 2018

(54) SPIROBIFLUORENE DERIVATIVE-BASED MATERIALS FOR ELECTRONIC DEVICES

(71) Applicant: Merck Patent GmbH, Darmstadt (DE)

(72) Inventors: Jochen Pfister, Seeheim-Jugenheim (DE); Teresa Mujica-Fernaud, Darmstadt (DE); Elvira Montenegro, Weinheim (DE)

(73) Assignee: Merck Patent GmbH (DE)

( * ) Notice: Subject to any disclaimer, the term of this patent is extended or adjusted under 35 U.S.C. 154(b) by 0 days.

(21) Appl. No.: 15/551,198

(22) PCT Filed: Jan. 19, 2016

(86) PCT No.: PCT/EP2016/000084
§ 371 (c)(1),
(2) Date: Aug. 15, 2017

(87) PCT Pub. No.: WO2016/131521
PCT Pub. Date: Aug. 25, 2016

(65) Prior Publication Data
US 2018/0026188 A1      Jan. 25, 2018

(30) Foreign Application Priority Data

Feb. 16, 2015 (EP) .................... 15000455

(51) Int. Cl.
| *H01L 51/00* | (2006.01) |
| *C07D 307/94* | (2006.01) |
| *C07D 405/12* | (2006.01) |
| *C07D 407/12* | (2006.01) |
| *C07D 339/08* | (2006.01) |
| *C07D 327/08* | (2006.01) |
| *C07D 409/10* | (2006.01) |
| *C07D 333/78* | (2006.01) |
| *H01L 51/50* | (2006.01) |

(52) U.S. Cl.
CPC .......... *H01L 51/006* (2013.01); *C07D 307/94* (2013.01); *C07D 327/08* (2013.01); *C07D 333/78* (2013.01); *C07D 339/08* (2013.01); *C07D 405/12* (2013.01); *C07D 407/12* (2013.01); *C07D 409/10* (2013.01); *H01L 51/0061* (2013.01); *H01L 51/0052* (2013.01); *H01L 51/0058* (2013.01); *H01L 51/0072* (2013.01); *H01L 51/0073* (2013.01); *H01L 51/0074* (2013.01); *H01L 51/5016* (2013.01); *H01L 51/5056* (2013.01); *H01L 51/5096* (2013.01)

(58) Field of Classification Search
CPC ............... H01L 51/006; H01L 51/0061; H01L 51/0052; H01L 51/0074; H01L 51/0073; H01L 51/0058; H01L 51/0072; H01L 51/5016; H01L 51/5096; H01L 51/5056; C07D 409/10; C07D 307/94; C07D 405/12; C07D 407/12; C07D 339/08; C07D 327/08; C07D 333/78
See application file for complete search history.

(56) References Cited

U.S. PATENT DOCUMENTS

| 9,735,385 | B2* | 8/2017 | Kroeber | ............. H01L 51/5004 |
| 2009/0134384 | A1* | 5/2009 | Stoessel | ................. C07F 5/025 |
| | | | | 257/40 |
| 2009/0159874 | A1* | 6/2009 | Vestweber | ............ C07C 211/54 |
| | | | | 257/40 |
| 2011/0303877 | A1* | 12/2011 | Meyer | ................... C08G 61/122 |
| | | | | 252/500 |
| 2012/0126179 | A1* | 5/2012 | Parham | .................... C07C 13/72 |
| | | | | 252/500 |
| 2012/0228552 | A1* | 9/2012 | Parham | ................ C07D 403/10 |
| | | | | 252/301.16 |
| 2013/0015403 | A1* | 1/2013 | Becker | ................ H01L 51/0059 |
| | | | | 252/301.16 |
| 2013/0334518 | A1 | 12/2013 | Park et al. | |
| 2014/0066656 | A1* | 3/2014 | Bruder | .................. H01L 51/006 |
| | | | | 564/322 |
| 2014/0197401 | A1* | 7/2014 | Kroeber | ............. H01L 51/0067 |
| | | | | 257/40 |
| 2014/0332787 | A1* | 11/2014 | Hong | ..................... H05B 33/14 |
| | | | | 257/40 |

FOREIGN PATENT DOCUMENTS

| EP | 2799515 A1 | 11/2014 |
| WO | WO-2012141229 A1 | 10/2012 |
| WO | WO-2014010910 A1 | 1/2014 |
| WO | WO-2014058232 A2 | 4/2014 |
| WO | WO-2015012618 A1 | 1/2015 |

OTHER PUBLICATIONS

International Search Report for PCT/EP2016/000084 dated Apr. 13, 2016.
Written Opinion of the International Searching Authority for PCT/EP2016/000084 dated Apr. 13, 2016.

* cited by examiner

*Primary Examiner* — Su C Kim
(74) *Attorney, Agent, or Firm* — Drinker Biddle & Reath LLP

(57) ABSTRACT

The present application relates to spirobifluorene derivatives of a formula (I), to the use thereof in electronic devices, and to processes for preparing said derivatives.

19 Claims, No Drawings

SPIROBIFLUORENE DERIVATIVE-BASED MATERIALS FOR ELECTRONIC DEVICES

CROSS-REFERENCE TO RELATED APPLICATIONS

This application is a national stage application (under 35 U.S.C. § 371) of PCT/EP2016/000084, filed Jan. 19, 2016, which claims benefit of European Application No. 15000455.4, filed Feb. 16, 2015, both of which are incorporated herein by reference in their entirety.

The present application relates to a spirobifluorene derivative of a formula (I) defined hereinafter which is suitable for use in electronic devices, especially organic electroluminescent devices (OLEDs).

Electronic devices in the context of this application are understood to mean what are called organic electronic devices, which contain organic semiconductor materials as functional materials. More particularly, these are understood to mean OLEDs.

The structure of OLEDs in which organic compounds are used as functional materials is described, for example, in U.S. Pat. No. 4,539,507, U.S. Pat. No. 5,151,629, EP 0676461 and WO 98/27136. In general, the term OLEDs is understood to mean electronic devices which have one or more layers comprising organic compounds and emit light on application of electrical voltage.

In electronic devices, especially OLEDs, there is great interest in improving the performance data, especially lifetime, efficiency and operating voltage. In these aspects, it has not yet been possible to find any entirely satisfactory solution.

A great influence on the performance data of electronic devices is possessed by layers having a hole-transporting function, for example hole-injecting layers, hole transport layers, electron blocker layers and also emitting layers. For use in these layers, there is a continuous search for new materials having hole-transporting properties.

It is known in the prior art that triarylamines can be used in these layers as materials having hole-transporting properties. The triarylamines may be monotriarylamines as described, for example, in JP 1995/053955, WO 2006/123667 and JP 2010/222268, or bis- or other oligoamines, as described, for example, in U.S. Pat. No. 7,504,163 or US 2005/0184657. Known examples of triarylamine compounds as materials having hole-transporting properties for OLEDs include tris-p-biphenylamine, N,N'-di-1-naphthyl-N,N'-diphenyl-1,1'-biphenyl-4,4'-diamine (NPB) and 4,4',4"-tris(3-methylphenylphenylamino)triphenylamine (MT-DATA). The prior art additionally discloses spirobifluorene-arylamino compounds for this purpose, for example as disclosed in WO 2012/034627 and WO 2013/120577.

Likewise disclosed in the prior art for this use are spirobifluorene derivatives having a benzofuran or benzothiophene unit fused onto the spirobifluorene base skeleton at a particular position, and having one or more arylamino groups bonded to the spirobifluorene (WO 2013/100467).

In the course of studies relating to novel materials for use in OLEDs, it has now been found that, surprisingly, compounds which differ from the abovementioned compounds in that they have a benzofuran or benzothiophene unit fused to the spirobifluorene base structure in a different position are of outstanding suitability for use in OLEDs, especially as materials having hole-transporting function. In particular they are superior to the abovementioned compounds with respect to their performance data in the case of use in OLEDs, very particularly in the case of the lifetime, the operating voltage and the quantum efficiency of the OLEDs. The novel compounds found have furthermore one or more properties selected from very good hole-conducting properties, very good electron-blocking properties, high glass transition temperature, high oxidation stability, good solubility and high thermal stability.

The present invention therefore provides a compound of the formula (I)

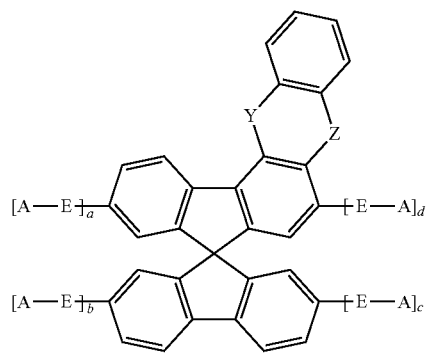

Formula (I)

which may be substituted at one or more positions shown as unsubstituted in the base structure of formula (I) by one $R^1$ radical each; and
which has the following definitions of the variables:
Y is selected from a single bond, O, S and Se;
Z is selected from O, S and Se;
E is the same or different at each instance and is a single bond or an aromatic or heteroaromatic ring system which has 6 to 30 aromatic ring atoms and may be substituted by one or more $R^2$ radicals;
A is the same or different at each instance and is a group of the formula (A1), (A2) or (A3) which is bonded via the bond marked with #;

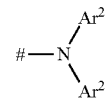

Formula (A1)

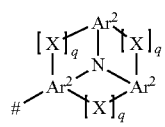

Formula (A2)

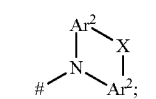

Formula (A3)

$Ar^2$ is the same or different at each instance and is an aromatic or heteroaromatic ring system which has 6 to 30 aromatic ring atoms and may be substituted by one or more $R^2$ radicals;
X is the same or different at each instance and is a single bond or a group selected from $BR^2$, $C(R^2)_2$, $Si(R^2)_2$, $C=O$, O, S, $S=O$, $SO_2$, $NR^2$, $PR^2$ and $P(=O)R^2$;
$R^1$ is the same or different at each instance and is selected from H, D, F, $C(=O)R^3$, CN, $Si(R^3)_3$, $P(=O)(R^3)_2$, $OR^3$, $S(=O)R^3$, $S(=O)_2R^3$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^1$ radicals may be joined to one another and may form a ring; where the alkyl, alkoxy, alkenyl and alkynyl groups mentioned and the aromatic ring systems and heteroaromatic ring systems mentioned may each be substituted by one or more $R^3$ radicals; and where one or more $CH_2$ groups in the alkyl, alkoxy, alkenyl and alkynyl groups mentioned may be replaced by —$R^3C$=$CR^3$—, —C≡C—, $Si(R^3)_2$, C=O, C=$NR^3$, —C(=O)O—, —C(=O)$NR^3$—, $NR^3$, P(=O)($R^3$), —O—, —S—, SO or $SO_2$;

$R^2$ is the same or different at each instance and is selected from H, D, F, C(=O)$R^3$, CN, $Si(R^3)_3$, $N(R^3)_2$, P(=O)($R^3)_2$, $OR^3$, S(=O)$R^3$, S(=O)$_2R^3$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^2$ radicals may be joined to one another and may form a ring; where the alkyl, alkoxy, alkenyl and alkynyl groups mentioned and the aromatic ring systems and heteroaromatic ring systems mentioned may each be substituted by one or more $R^3$ radicals; and where one or more $CH_2$ groups in the alkyl, alkoxy, alkenyl and alkynyl groups mentioned may be replaced by —$R^3C$=$CR^3$—, —C≡C—, $Si(R^3)_2$, C=O, C=$NR^3$, —C(=O)O—, —C(=O)$NR^3$—, $NR^3$, P(=O)($R^3$), —O—, —S—, SO or $SO_2$;

$R^3$ is the same or different at each instance and is selected from H, D, F, C(=O)$R^4$, CN, $Si(R')_3$, $N(R^4)_2$, P(=O)($R^4)_2$, $OR^4$, S(=O)$R^4$, S(=O)$_2R^4$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^1$ or $R^2$ radicals may be joined to one another and may form a ring; where the alkyl, alkoxy, alkenyl and alkynyl groups mentioned and the aromatic ring systems and heteroaromatic ring systems mentioned may each be substituted by one or more $R^4$ radicals; and where one or more $CH_2$ groups in the alkyl, alkoxy, alkenyl and alkynyl groups mentioned may be replaced by —$R^4C$=$CR^4$—, —C≡C—, $Si(R^4)_2$, C=O, C=$NR^4$, —C(=O)O—, —C(=O)$NR^4$—, $NR^1$, P(=O)($R^4$), —O—, —S—, SO or $SO_2$;

$R^4$ is the same or different at each instance and is selected from H, D, F, CN, alkyl groups having 1 to 20 carbon atoms, aromatic ring systems having 6 to 40 aromatic ring atoms and heteroaromatic ring systems having 5 to 40 aromatic ring atoms; where two or more $R^4$ radicals may be joined to one another and may form a ring; and where the alkyl groups, aromatic ring systems and heteroaromatic ring systems mentioned may be substituted by F or CN;

q is the same or different at each instance and is 0 or 1, where at least one q in formula (A2) is 1;

a, b, c and d are the same or different at each instance and are 0 or 1, where at least one of the indices a, b, c and d is 1, and where, in the case that one or more of the indices a, b, c and d are 0, an $R^1$ group is attached at the position in question.

An aryl group in the context of this invention contains 6 to 40 aromatic ring atoms of which none is a heteroatom. An aryl group in the context of this invention is understood to mean either a simple aromatic cycle, i.e. benzene, or a fused aromatic polycycle, for example naphthalene, phenanthrene or anthracene. A fused aromatic polycycle in the context of the present application consists of two or more simple aromatic cycles fused to one another. Fusion between cycles is understood here to mean that the cycles share at least one edge with one another.

A heteroaryl group in the context of this invention contains 5 to 40 aromatic ring atoms of which at least one is a heteroatom. The heteroatoms of the heteroaryl group are preferably selected from N, O and S. A heteroaryl group in the context of this invention is understood to mean either a simple heteroaromatic cycle, for example pyridine, pyrimidine or thiophene, or a fused heteroaromatic polycycle, for example quinoline or carbazole. A fused heteroaromatic polycycle in the context of the present application consists of two or more simple heteroaromatic cycles fused to one another. Fusion between cycles is understood here to mean that the cycles share at least one edge with one another.

An aromatic ring system in the context of this invention contains 6 to 40 carbon atoms in the ring system and does not include any heteroatoms as aromatic ring atoms. An aromatic ring system in the context of this invention therefore does not contain any heteroaryl groups. An aromatic ring system in the context of this invention shall be understood to mean a system which does not necessarily contain only aryl groups but in which it is also possible for a plurality of aryl groups to be bonded by a single bond or by a non-aromatic unit, for example one or more optionally substituted C, Si, N, O or S atoms. In this case, the nonaromatic unit comprises preferably less than 10% of the atoms other than H, based on the total number of atoms other than H in the system. For example, systems such as 9,9'-spirobifluorene, 9,9'-diarylfluorene, triarylamine, diaryl ethers and stilbene are also to be regarded as aromatic ring systems in the context of this invention, and likewise systems in which two or more aryl groups are joined, for example, by a linear or cyclic alkyl, alkenyl or alkynyl group or by a silyl group. In addition, systems in which two or more aryl groups are joined to one another via single bonds are also to be regarded as aromatic ring systems in the context of this invention, for example systems such as biphenyl and terphenyl.

A heteroaromatic ring system in the context of this invention contains 5 to 40 aromatic ring atoms, at least one of which is a heteroatom. The heteroatoms of the heteroaromatic ring system are preferably selected from N, O and/or S. A heteroaromatic ring system corresponds to the above-mentioned definition of an aromatic ring system, but has at least one heteroatom as one of the aromatic ring atoms. In this way, it differs from an aromatic ring system in the sense of the definition of the present application, which, according to this definition, cannot contain any heteroatom as aromatic ring atom.

An aryl or heteroaryl group is especially understood to mean groups derived from benzene, naphthalene, anthracene, phenanthrene, pyrene, dihydropyrene, chrysene, perylene, triphenylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, Indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aromatic ring system having 6 to 40 aromatic ring atoms or a heteroaromatic ring system having 5 to 40 aromatic ring atoms is especially understood to mean groups derived from the groups mentioned above under aryl groups and heteroaryl groups, and from biphenyl, terphenyl, quaterphenyl, fluorene, spirobifluorene, dihydrophenanthrene, dihydropyrene, tetrahydropyrene, indenofluorene, truxene, isotruxene, spirotruxene, spiroisotruxene, indenocarbazole, or from combinations of these groups.

In the context of the present invention, a straight-chain alkyl group having 1 to 20 carbon atoms and a branched or cyclic alkyl group having 3 to 20 carbon atoms and an alkenyl or alkynyl group having 2 to 40 carbon atoms in which individual hydrogen atoms or $CH_2$ groups may also be replaced by the groups mentioned above in the definition of the radicals are preferably understood to mean the methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl radicals.

An alkoxy or thioalkyl group having 1 to 20 carbon atoms in which individual hydrogen atoms or $CH_2$ groups may also be replaced by the groups mentioned above in the definition of the radicals is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethythio, ethenylthio, propenytthio, butenylthio, pentenylthio, cyclopentenylthio, hexenylthio, cyclohexenylthio, heptenylthio, cycloheptenylthio, octenylthio, cyclooctenylthio, ethynytthio, propynylthio, butynylthio, pentynylthio, hexynylthio, heptynylthio or octynythio.

The wording that two or more radicals together may form a ring, in the context of the present application, shall be understood to mean, inter alia, that the two radicals are joined to one another by a chemical bond. In addition, however, the abovementioned wording shall also be understood to mean that, if one of the two radicals is hydrogen, the second radical binds to the position to which the hydrogen atom was bonded, forming a ring.

According to the invention, it is preferable that Y is selected from a single bond, O and S. According to the invention, it is further preferable that Z is selected from O and S. It is particularly preferable that Y is a single bond, and that Z is selected from O and S. According to a further embodiment of the invention, it is preferable that Y is selected from O and S, and that Z is selected from O and S.

It is further preferable that E is the same or different at each instance and is selected from a single bond and a divalent group derived from benzene, biphenyl, terphenyl, fluorene, spirobifluorene, indenofluorene, carbazole, dibenzofuran or dibenzothiophene, each optionally substituted by $R^2$ radicals, or a combination of two or more of these groups, where not more than 30 aromatic ring atoms are present in the E group.

E groups are preferably selected from a singe bond or from groups of the following formulae:

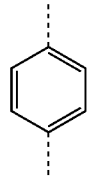

E-1

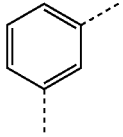

E-2

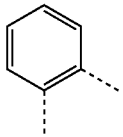

E-3

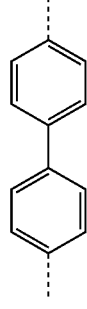

E-4

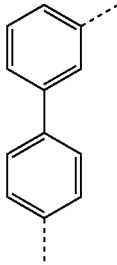

E-5

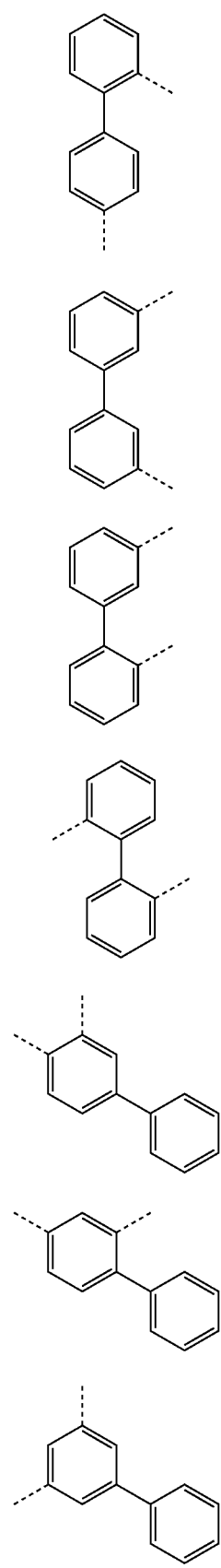
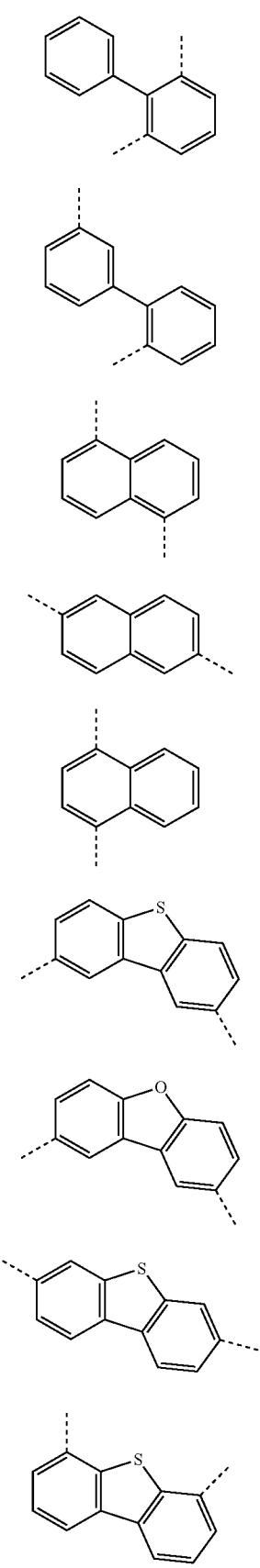

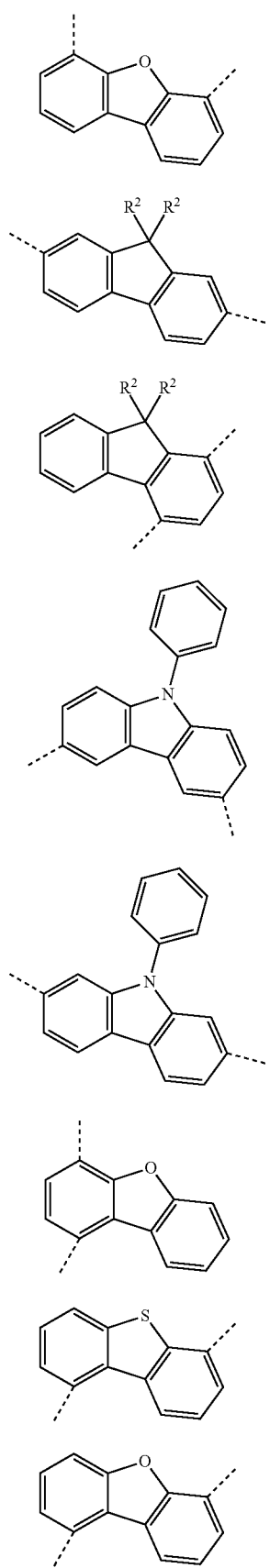
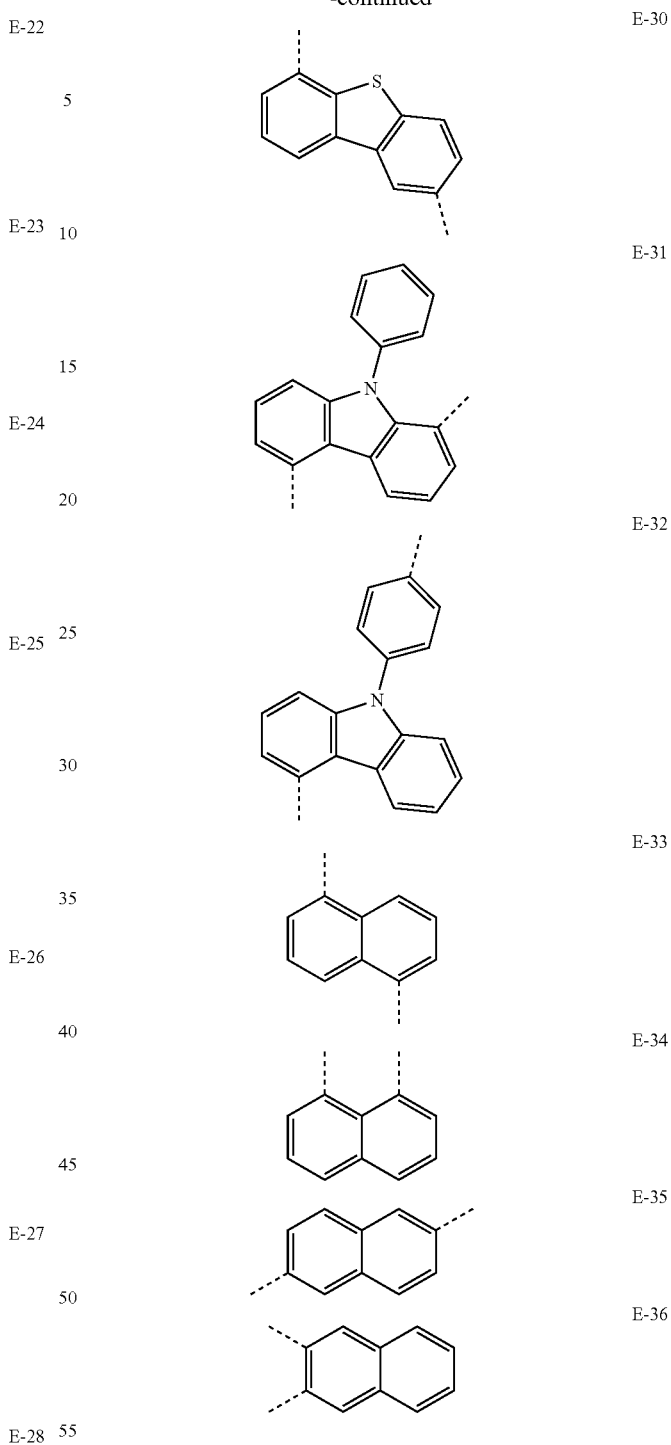

where the dotted bonds represent the bonds to the radical of the formula and the groups may be substituted at the free positions by one or more $R^2$ radicals, but are preferably unsubstituted at the free positions.

$R^2$ in the groups of the formulae (E-23) and (E-24) is preferably the same or different and is an alkyl group having 1 to 10 carbon atoms, especially methyl, or is a phenyl group which may be substituted by one or more $R^3$ radicals and is preferably unsubstituted. Two alkyl groups $R^2$ may also form a ring with formation of a spiro group, preferably a cyclohexyl ring or a cyclopentyl ring.

It is preferable that A is the same or different at each instance and is a group of the formula (A-1) or (A-3), more preferably a group of the formula (A-1).

A preferred embodiment of the group of the formula (A-3) is a group of the following formula (A-3-1):

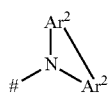

Formula (A-3-1)

where the Ar² group is as defined above, and is preferably defined according to the preferred embodiments thereof.

Preferred embodiments of the groups of the formula (A-3-1) correspond to the following formulae

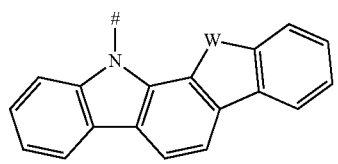

Formula (A-3-1a)

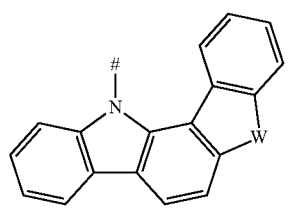

Formula (A-3-1b)

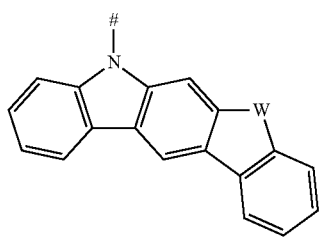

Formula (A-3-1c)

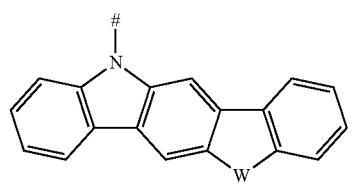

Formula (A-3-1d)

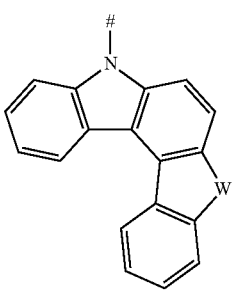

Formula (A-3-1e)

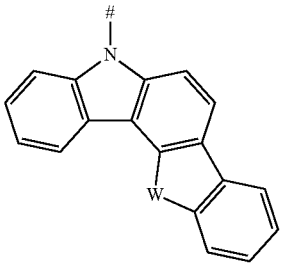

Formula (A-3-1f)

Formula (A-3-1g)

where the groups may be substituted at the unoccupied positions by one $R^2$ radical each, and where W is the same or different at each instance and is selected from $BR^2$, $C(R^2)_2$, $Si(R^2)_2$, C=O, O, S, S=O, $SO_2$, $NR^2$, $PR^2$ and $P(=O)R^2$, and is preferably selected from $C(R^2)_2$, O, S and $NR^2$, and is more preferably $C(R^2)_2$.

Among the groups of the formulae (A-3-1a) to (A-3-1g), particular preference is given to the groups (A-3-1c) and (A-3-1g).

It is preferable that Ar² is the same or different at each instance and is selected from an aromatic or heteroaromatic ring system which has 6 to 25 aromatic ring atoms and may be substituted by one or more $R^2$ radicals. Particular preference is given to phenyl, biphenyl, terphenyl, fluorenyl, spirobifluorenyl, indenofluorenyl, naphthyl, phenanthrenyl, furanyl, benzofuranyl, dibenzofuranyl, thiophenyl, benzothiophenyl, dibenzothiophenyl, carbazolyl, indolocarbazolyl and indenocarbazolyl, each of which may be substituted by one or more $R^2$ radicals.

Ar² groups are preferably the same or different at each instance and are selected from groups of the following formulae:

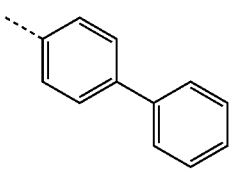

Ar²-1

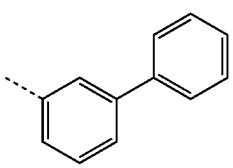

Ar²-2

-continued
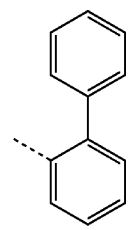
Ar²-3
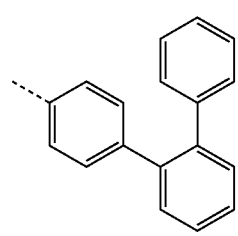
Ar²-4
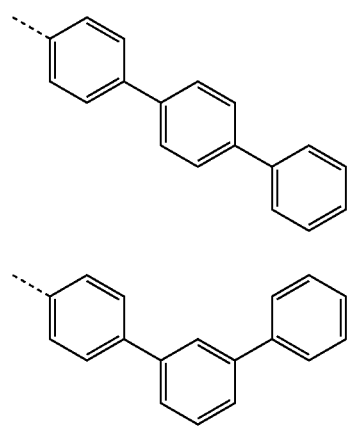
Ar²-5
Ar²-6
Ar²-7
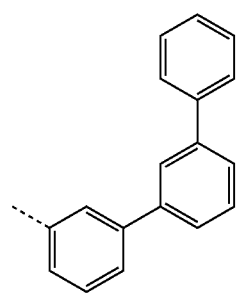
Ar²-8
-continued
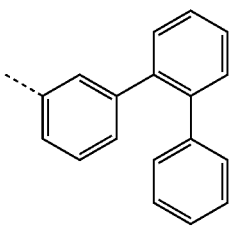
Ar²-9
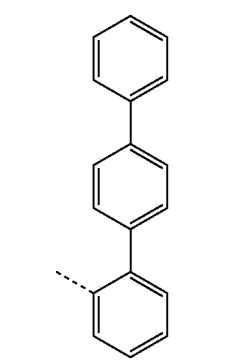
Ar²-10
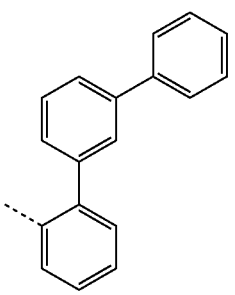
Ar²-11
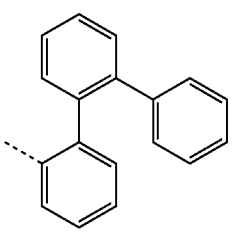
Ar²-12
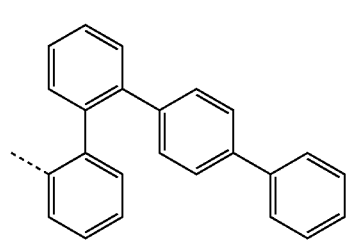
Ar²-13

Ar²-14
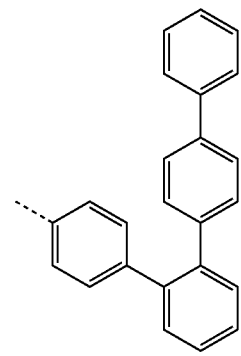
Ar²-15
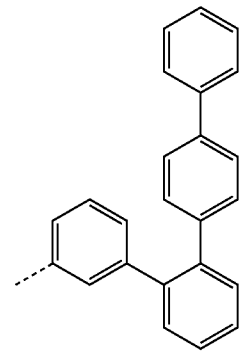
Ar²-16
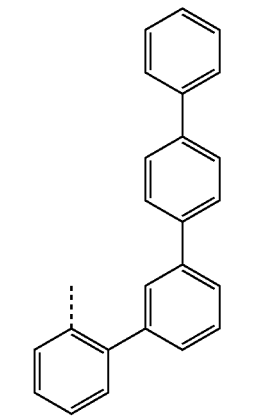
Ar²-17
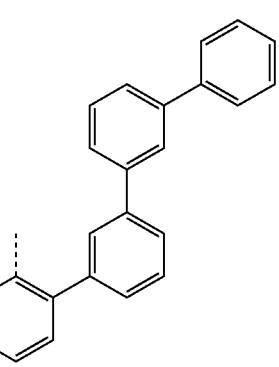
Ar²-18
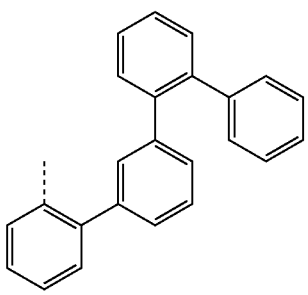
Ar²-19
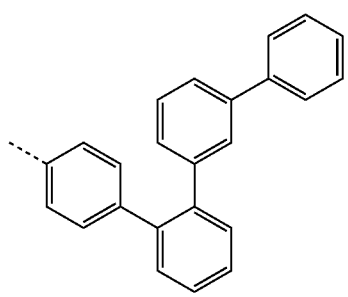
Ar²-20
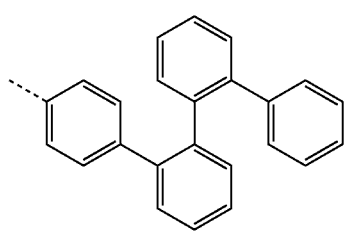
Ar²-21
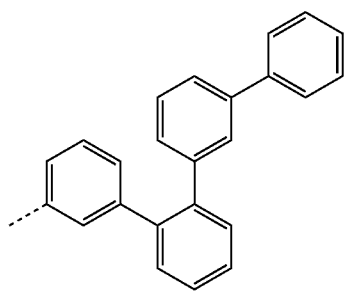
Ar²-22
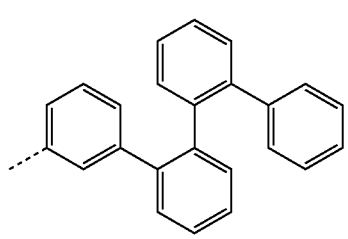

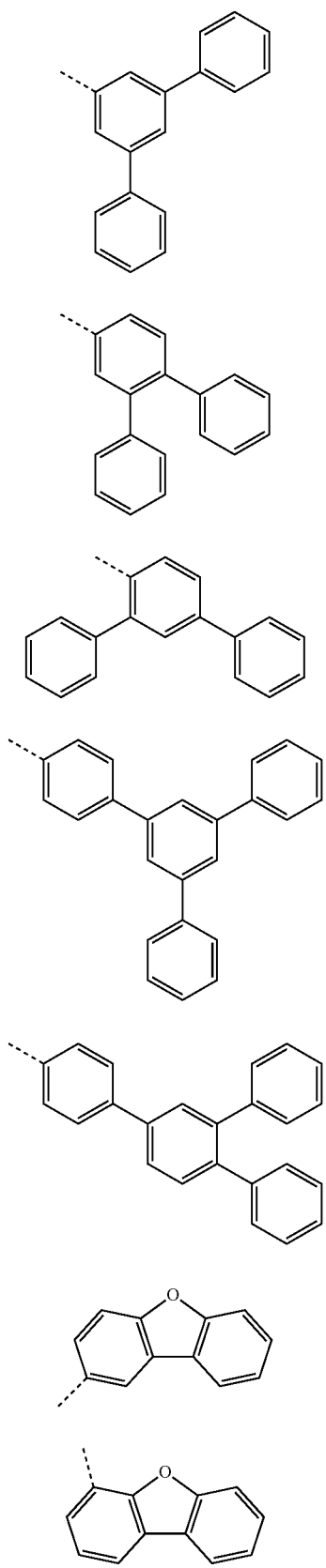

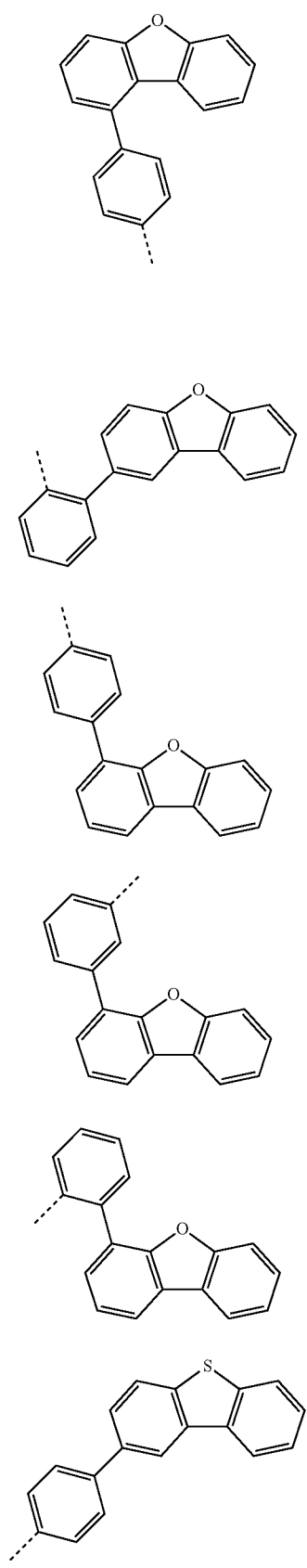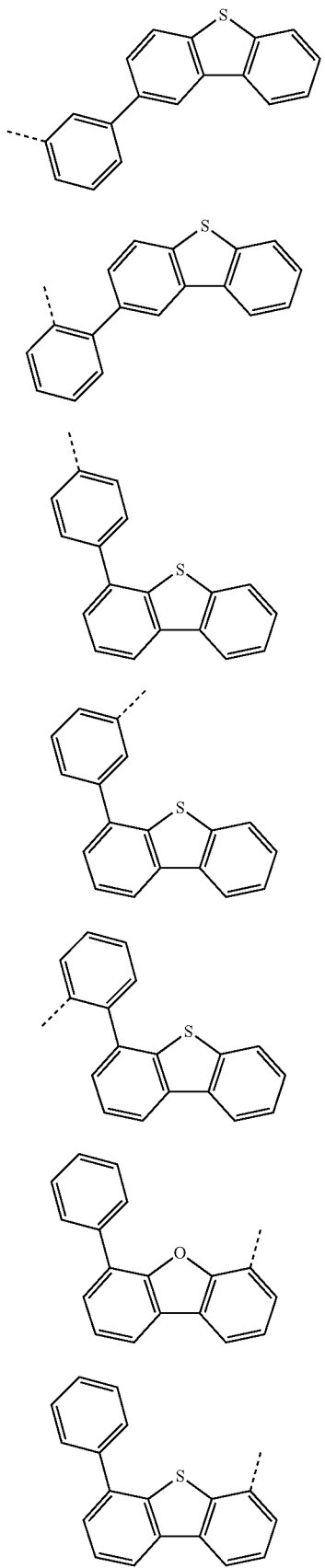

Ar²-52 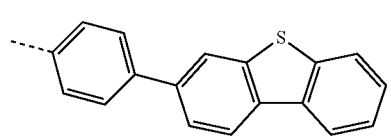
Ar²-53 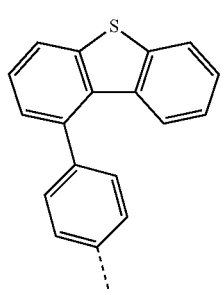
Ar²-54 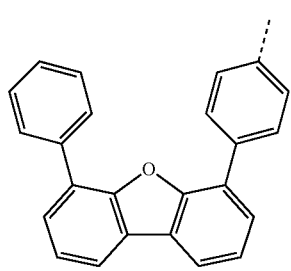
Ar²-55 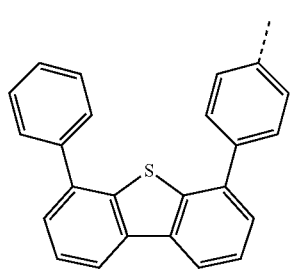
Ar²-56 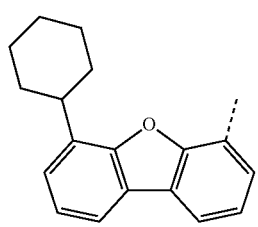
Ar²-57 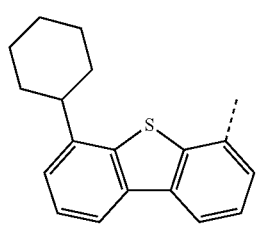
Ar²-58 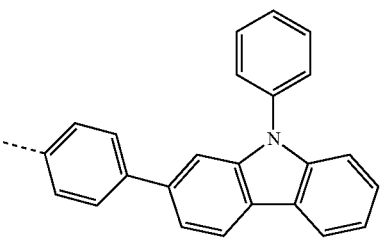
Ar²-59 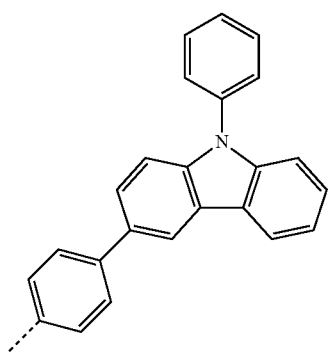
Ar²-60 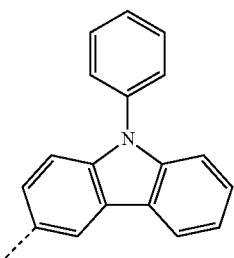
Ar²-61 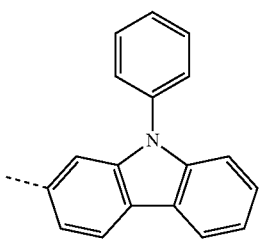
Ar²-62 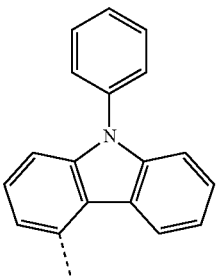

Ar²-63 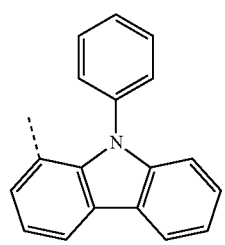
Ar²-64 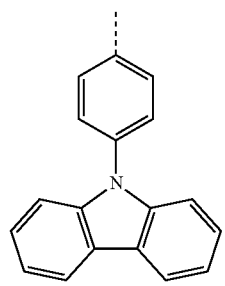
Ar²-65 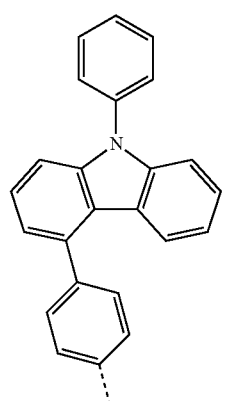
Ar²-66 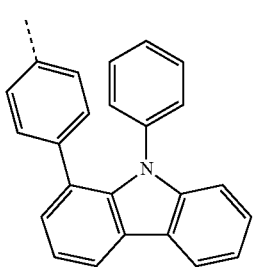
Ar²-67 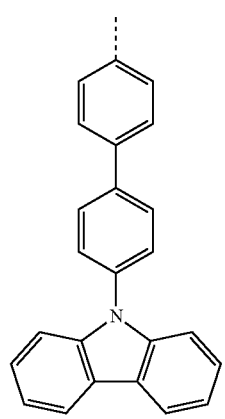
Ar²-68 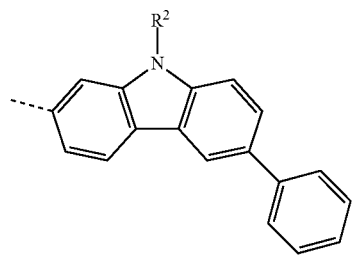
Ar²-69 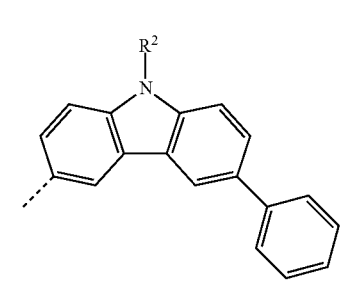
Ar²-70 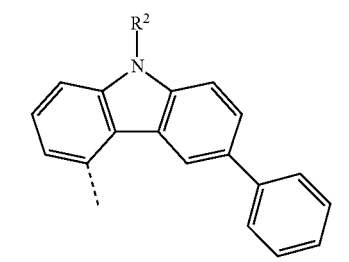
Ar²-71 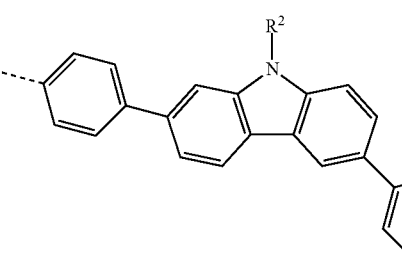
Ar²-72 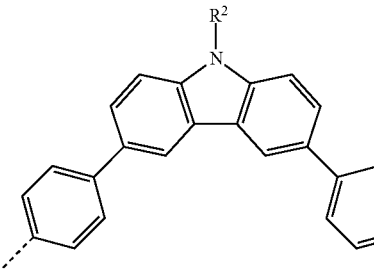

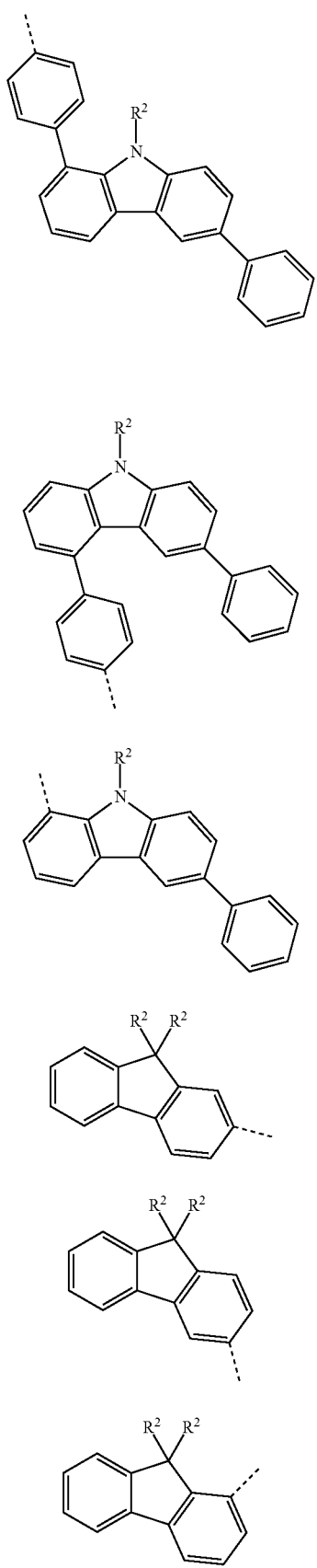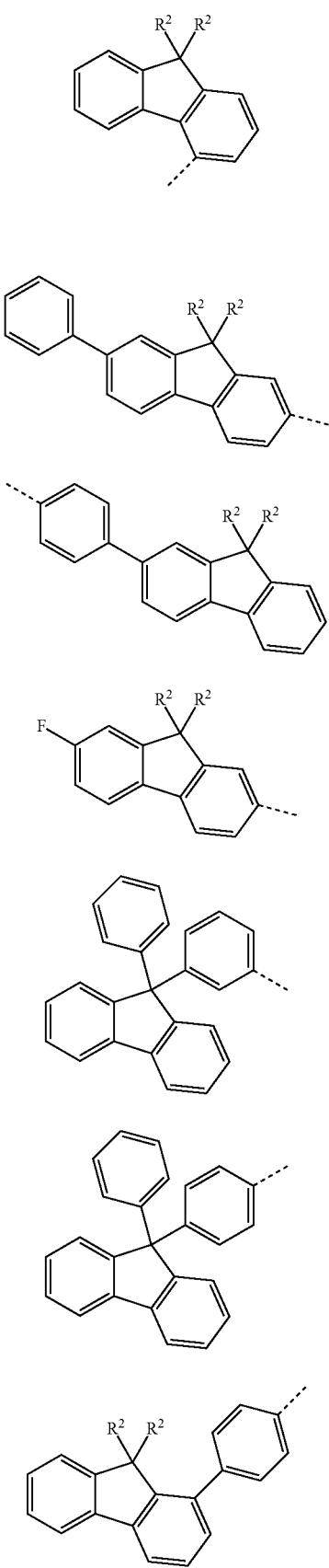

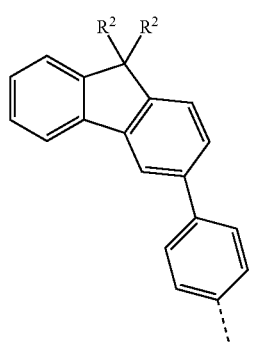
Ar²-86
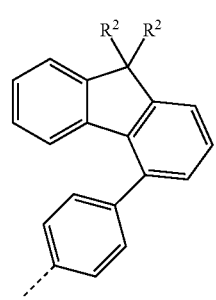
Ar²-87
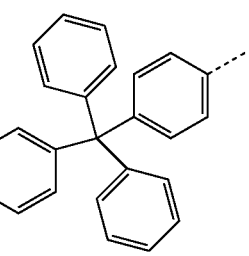
Ar²-88
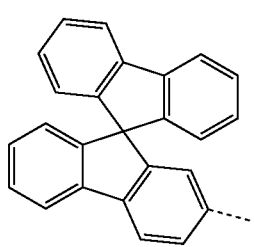
Ar²-89
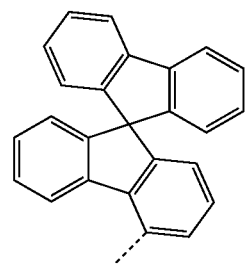
Ar²-90
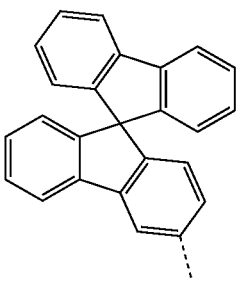
Ar²-91
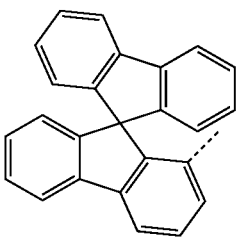
Ar²-92
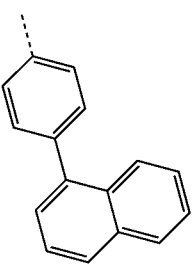
Ar²-93
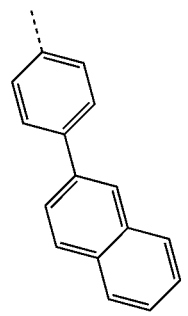
Ar²-94
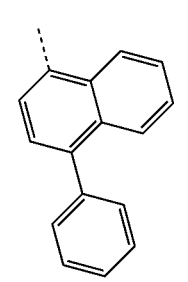
Ar²-95
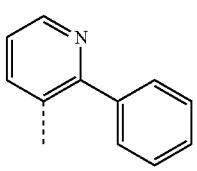
Ar²-96

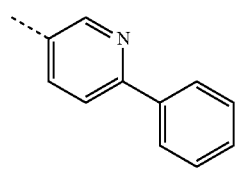 Ar²-97
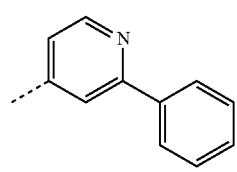 Ar²-98
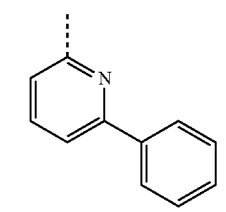 Ar²-99
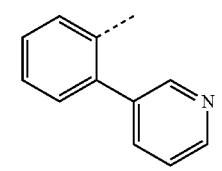 Ar²-100
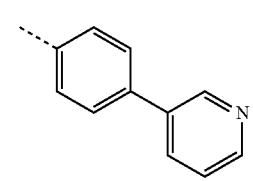 Ar²-101
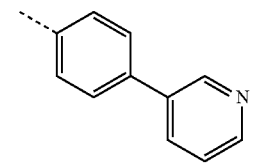 Ar²-102
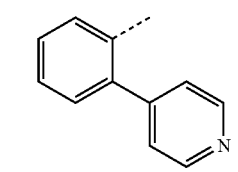 Ar²-103
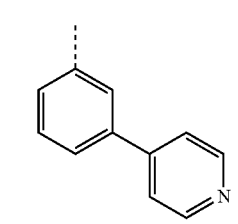 Ar²-104
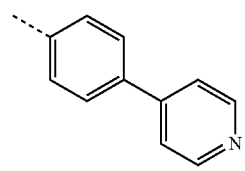 Ar²-105
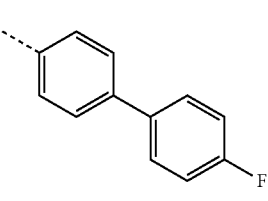 Ar²-106
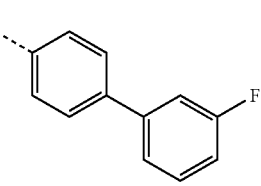 Ar²-107
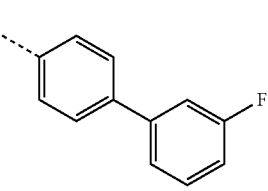 Ar²-108
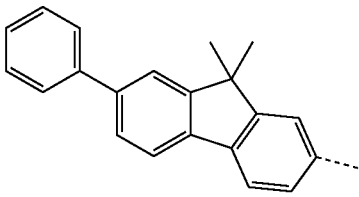 Ar²-109
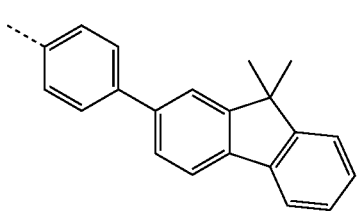 Ar²-110
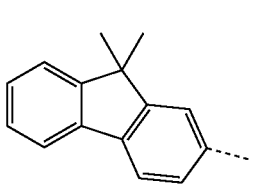 Ar²-111
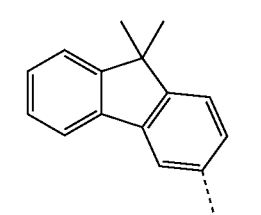 Ar²-112

Ar²-113 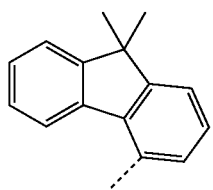

Ar²-114 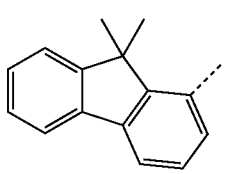

Ar²-115 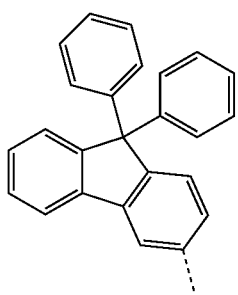

Ar²-116 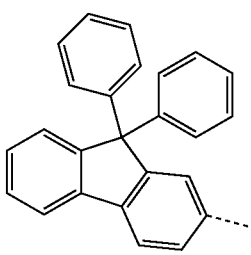

Ar²-117 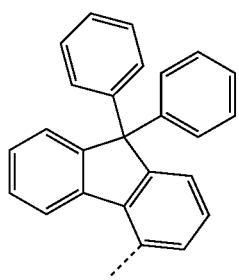

Ar²-118 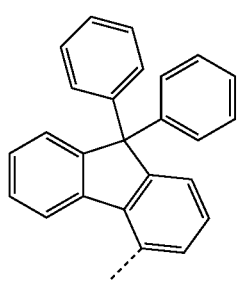

Ar²-119 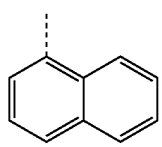

Ar²-120 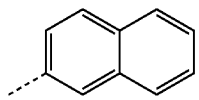

Ar²-121 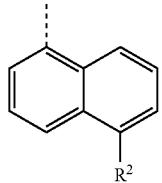

Ar²-122 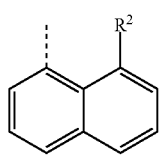

Ar²-123 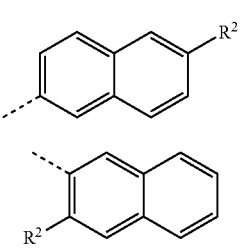

Ar²-124 where the dotted bond represents the bond to the nitrogen and the groups may be substituted at the free positions by one or more R² radicals, but are preferably unsubstituted at the free positions.

R² in the groups of the formulae (Ar²-68) to (Ar²-82) and (Ar²-85) to (Ar²-87) is preferably the same or different and is an alkyl group having 1 to 10 carbon atoms, especially methyl, or a phenyl group which may be substituted by one or more R³ radicals and is preferably unsubstituted. Two alkyl groups R² may also form a ring with formation of a spiro group, preferably a cyclohexyl ring or a cyclopentyl ring.

It is preferable that X is the same or different at each instance and is selected from a single bond or a group selected from C(R²)₂, C=O, O, S and NR²; more preferably, X is a single bond.

Preferably, R¹ is the same or different at each instance and is H, D, F, CN, Si(R³)₃, a straight-chain alkyl or alkoxy group having 1 to 10 carbon atoms, a branched or cyclic alkyl or alkoxy group having 3 to 10 carbon atoms, or an aromatic or heteroaromatic ring system having 6 to 30 aromatic ring atoms, where two or more $R^1$ radicals may be joined to one another and may form a ring, where the alkyl and alkoxy groups mentioned and the aromatic and heteroaromatic ring systems mentioned may each be substituted by one or more $R^3$ radicals, and where, in the alkyl and alkoxy groups mentioned, one or more $CH_2$ groups may be replaced by —C≡C—, —$R^3$C=C$R^3$—, Si($R^3$)$_2$, C=O, C=N$R^3$, —N$R^3$—, —O—, —S—, —C(=O)O— or —C(=O)N$R^3$—. More preferably, $R^1$ is the same or different at each instance and is H, D, F, CN, a straight-chain alkyl group having 1 to 10 carbon atoms or a branched or cyclic alkyl group having 3 to 10 carbon atoms, or an aromatic or heteroaromatic ring system having 6 to 25 aromatic ring atoms, where the alkyl and alkoxy groups mentioned and the aromatic and heteroaromatic ring systems mentioned may each be substituted by one or more $R^3$ radicals. Even more preferably, $R^1$ is the same or different at each instance and is H, F, CN, methyl, tert-butyl, phenyl, biphenyl, dibenzofuran, dibenzothiophene or carbazole, and even more preferably still is H.

Preferably, $R^2$ is the same or different at each instance and is H, D, F, CN, Si($R^3$)$_3$, a straight-chain alkyl or alkoxy group having 1 to 10 carbon atoms, a branched or cyclic alkyl or alkoxy group having 3 to 10 carbon atoms or an aromatic or heteroaromatic ring system having 6 to 30 aromatic ring atoms, where two or more $R^2$ radicals may be joined to one another and may form a ring, where said alkyl and alkoxy groups and said aromatic and heteroaromatic ring systems may each be substituted by one or more $R^3$ radicals, and where one or more $CH_2$ groups in the alkyl and alkoxy groups mentioned may be replaced by —C≡C—, —$R^3$C=C$R^3$—, Si($R^3$)$_2$, C=O, C=N$R^3$, —N$R^3$—, —O—, —S—, —C(=O)O— or —C(=O)N$R^3$—. More preferably, $R^2$ is the same or different at each instance and is H, D, F, CN, a straight-chain alkyl group having 1 to 10 carbon atoms or a branched or cyclic alkyl group having 3 to 10 carbon atoms, or an aromatic or heteroaromatic ring system having 6 to 25 aromatic ring atoms, where said alkyl and alkoxy groups and said aromatic or heteroaromatic ring systems may each be substituted by one or more $R^3$ radicals. Most preferably, $R^2$ is the same or different at each instance and is H, F, CN, methyl, tert-butyl, phenyl, biphenyl, dibenzofuran, dibenzothiophene or carbazole.

Preferably, $R^3$ is the same or different at each instance and is H, D, F, CN, Si($R^4$)$_3$, N(R')$_2$, a straight-chain alkyl or alkoxy group having 1 to 10 carbon atoms or a branched or cyclic alkyl or alkoxy group having 3 to 10 carbon atoms or an aromatic or heteroaromatic ring system having 5 to 30 aromatic ring atoms, where two or more $R^3$ radicals may be joined to one another and may form a ring, where said alkyl and alkoxy groups and said aromatic or heteroaromatic ring systems may each be substituted by one or more R radicals, and where one or more $CH_2$ groups in the alkyl and alkoxy groups mentioned may be replaced by —C≡C—, —$R^4$C=C$R^4$—, Si($R^4$)$_2$, C=O, C=N$R^4$, —N$R^4$—, —O—, —S—, —C(=O)O— or —C(=O)N$R^4$—. More preferably, $R^3$ is the same or different at each instance and is H, D, F, CN, N($R^4$)$_2$, a straight-chain alkyl group having 1 to 10 carbon atoms or a branched or cyclic alkyl group having 3 to 10 carbon atoms, or an aromatic or heteroaromatic ring system having 6 to 25 aromatic ring atoms, where said alkyl and alkoxy groups and said aromatic or heteroaromatic ring systems may each be substituted by one or more R radicals.

It is preferable in accordance with the invention that exactly one of the indices a, b, c and d is 1, and the other indices are 0; or that exactly two of the indices a, b, c and d are 1, and the other indices are 0.

In addition, it is preferable that the index d is 0, and that one or more, preferably exactly one or exactly two, of the indices a, b and c are 1.

In addition, it is preferable that, when Y is a single bond, and Z is O, and the index a is 1, at least one of the indices b, c and d is 1. It is particularly preferable that, when the index a is 1, at least one of the indices b, c and d is 1.

A preferred embodiment of the formula (I) corresponds to the following formula:

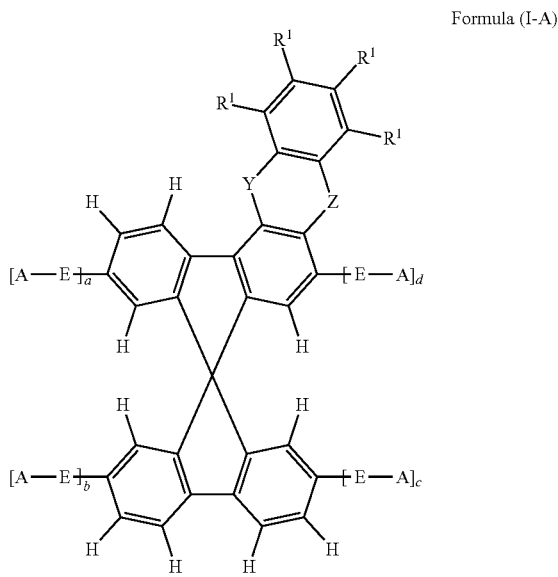

Formula (I-A)

where the variables that occur are as defined above, and preferably correspond to the preferred embodiments thereof. Only hydrogen can be present at the positions indicated by "H". Preferably, in formula (I-A), $R^1$ is hydrogen.

In this case too, it is preferable that, when Y is a single bond, and Z is O, and the index a is 1, at least one the indices b, c and d is 1. It is particularly preferable that, when the index a is 1, at least one of the indices b, c and d is 1.

Preferred embodiments of the formula (I) correspond to the following formulae

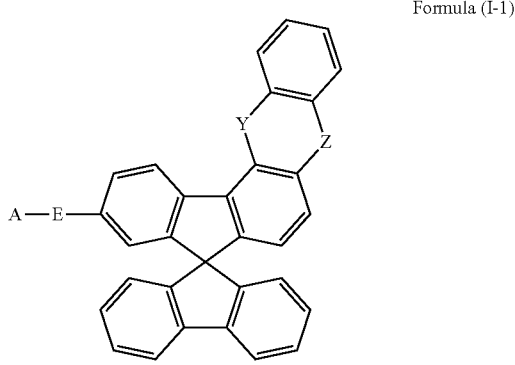

Formula (I-1)

Formula (I-2)

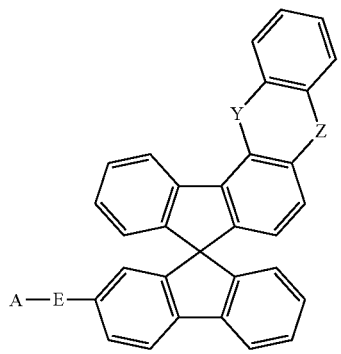

Formula (I-6)

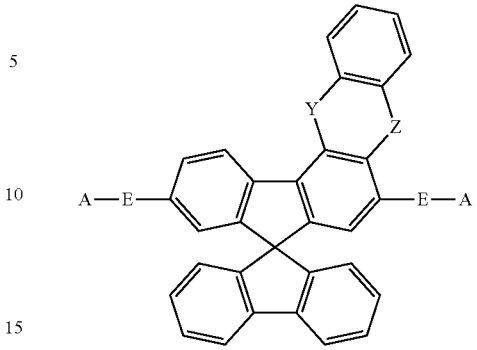

Formula (I-3)

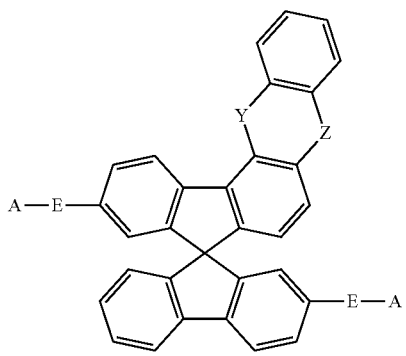

where the variables that occur are as defined above, and preferably correspond to the preferred embodiments thereof, and where the base structure of formula (I-1) to (I-6) may be substituted at one or more positions shown as unsubstituted by one $R^1$ radical each.

For formula (I-1), it is preferable that the case that Y is a single bond and, at the same time, Z is O is ruled out.

Among the formulae (I-1) to (I-6), preference is given to the formulae (I-1) to (I-4), particular preference to the formulae (I-1) and (I-2), and very particular preference to the formula (I-2).

Preferred embodiments of the formulae (I-1) to (I-6) correspond to the following formulae Formula (I-4)

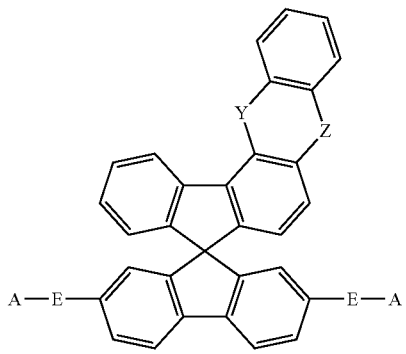

Formula (I-A-1)

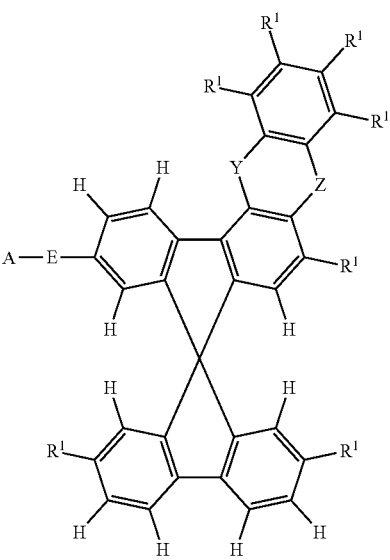

Formula (I-5)

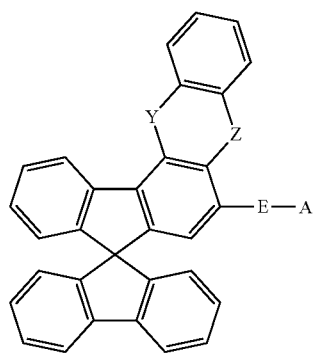

Formula (I-A-2)
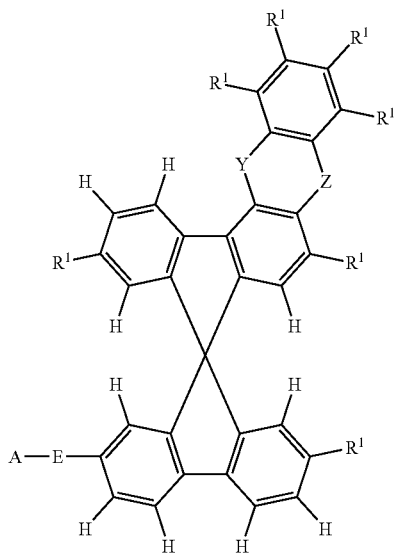

Formula (I-A-3)
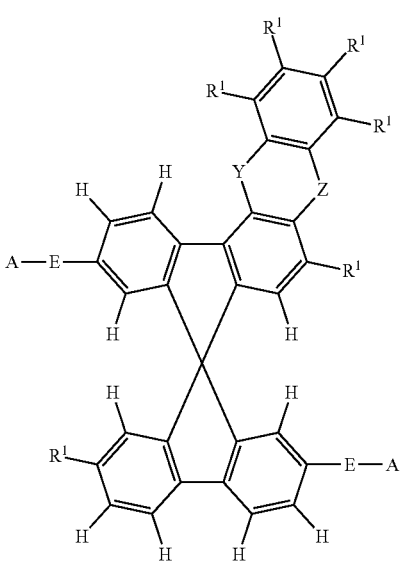

Formula (I-A-4)
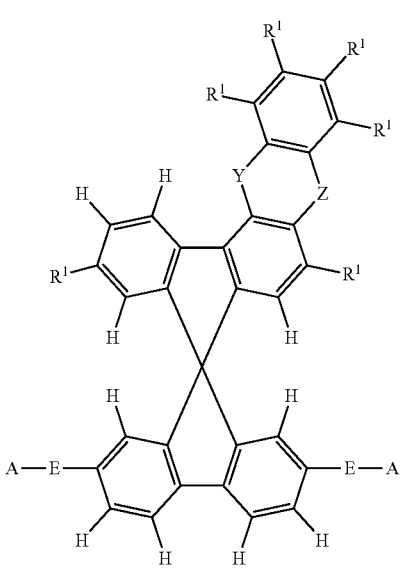

Formula (I-A-5)
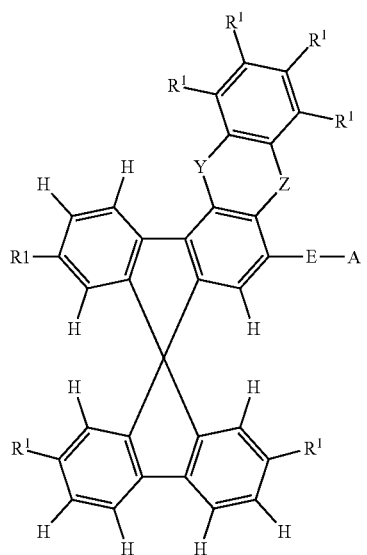

Formula (I-A-6)
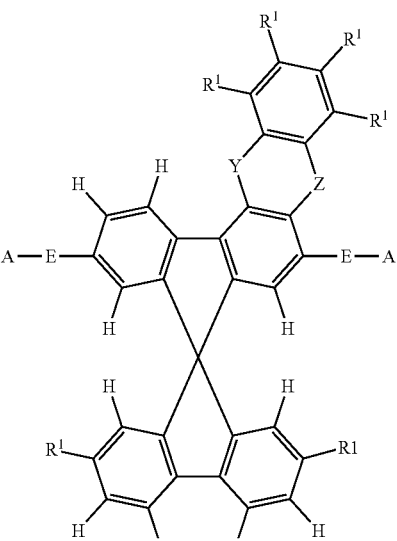

where the variables that occur are as defined above, and preferably correspond to the preferred embodiments thereof. Only hydrogen can be present at the positions indicated by "H". Preferably, in the formulae (I-A-1) to (I-A-6), $R^1$ is hydrogen.

Among the formulae (I-A-1) to (I-A-6), preference is given to the formulae (I-A-1) to (I-A-4), particular preference to the formulae (I-A-1) and (I-A-2), and very particular preference to the formula (I-A-2).

For formula (I-A-1), it is preferable that the case that Y is a single bond and, at the same time, Z is O is ruled out.

In addition, preferred embodiments of the formulae (I-1) to (I-6) correspond to the following formulae Formula (I-1-1)
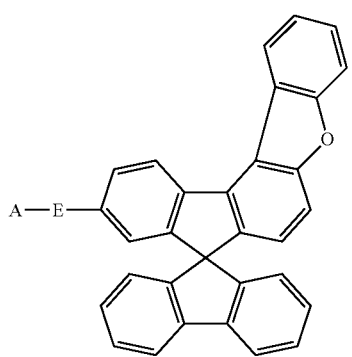
Formula (I-3-1)
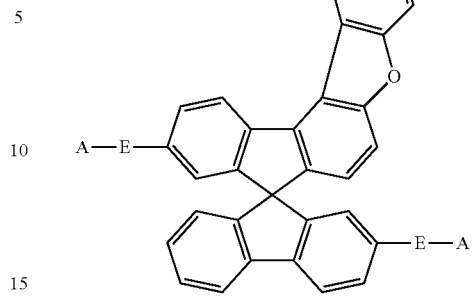
Formula (I-1-2)
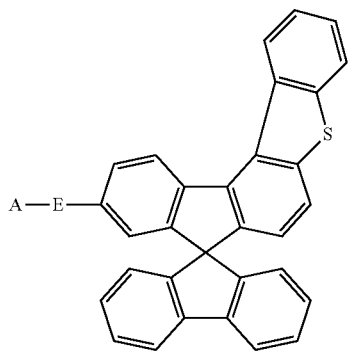
Formula (I-3-2)
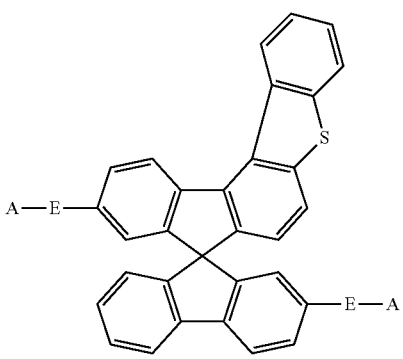
Formula (I-2-1)
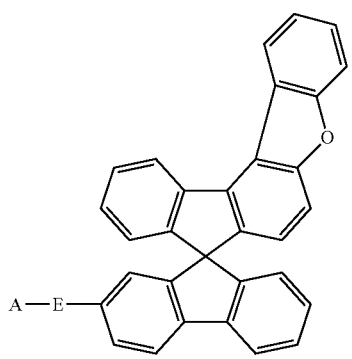
Formula (I-4-1)
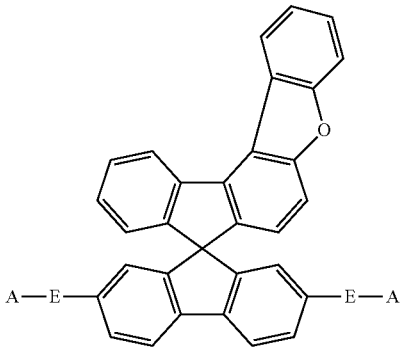
Formula (I-2-2)
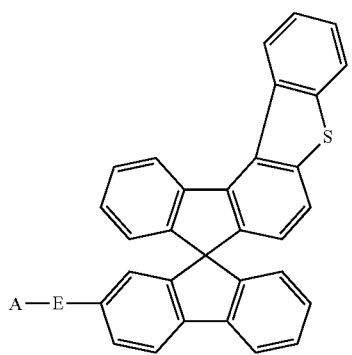
Formula (I-4-2)
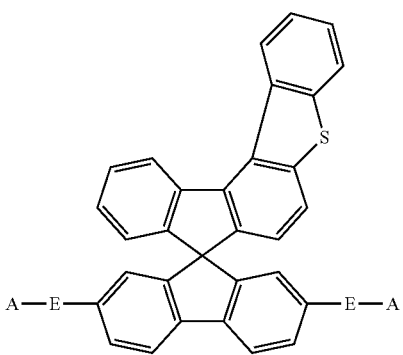

-continued

Formula (I-5-1)

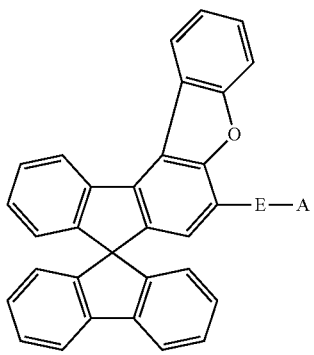

Formula (I-5-2)

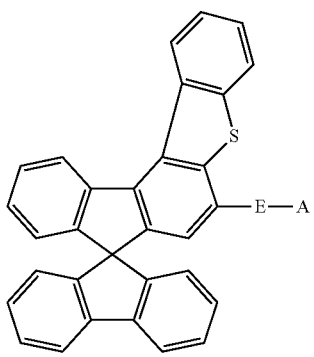

Formula (I-6-1)

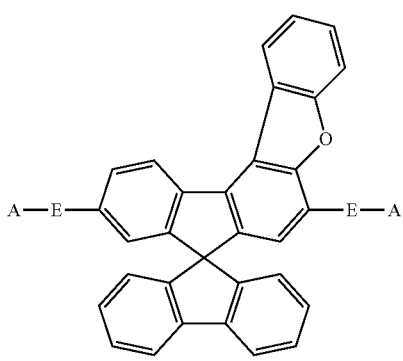

Formula (I-6-2)

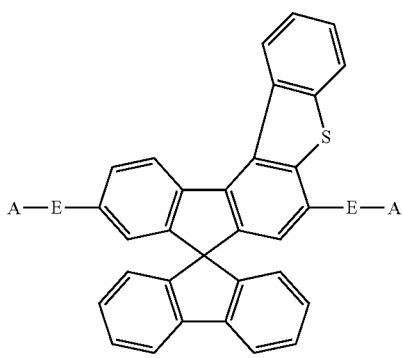

where the variables that occur are as defined above, and preferably correspond to the preferred embodiments thereof, and where the base structure of formula (I-1-1) to (I-6-2) may be substituted at one or more positions shown as unsubstituted by one $R^1$ radical each.

Among the formulae mentioned, preference is given to the formulae (I-1-1) to (I-4-2).

Very particularly preferred embodiments of the compounds of formula (I) correspond to one of the formulae (I-A-1) to (I-A-6) or one of the formulae (I-1-1) to (I-6-2), in which case, in addition:

Y is, if present, selected from a single bond, O and S;

Z is, if present, selected from O and S;

E is the same or different at each instance and is selected from a single bond and a divalent group derived from benzol, biphenyl, terphenyl, fluorene, spirobifluorene, indenofluorene, carbazole, dibenzofuran, dibenzothiophene, each optionally substituted by $R^2$ radicals, or a combination of two or more of these groups, where not more than 30 aromatic ring atoms are present in the E group;

A is a group of the formula (A-1) or (A-3), preferably a group of the formula (A-1);

$Ar^2$ is the same or different at each instance and is selected from an aromatic or heteroaromatic ring system which has 6 to 25 aromatic ring atoms and may be substituted by one or more $R^2$ radicals, and is preferably selected from phenyl, biphenyl, terphenyl, fluorenyl, spirobifluorenyl, indenofluorenyl, naphthyl, phenanthrenyl, furanyl, benzofuranyl, dibenzofuranyl, thiophenyl, benzothiophenyl, dibenzothiophenyl, carbazolyl, indolocarbazolyl and indenocarbazolyl, each of which may be substituted by one or more $R^2$ radicals;

$R^1$ is the same or different at each instance and is H, D, F, CN, a straight-chain alkyl group having 1 to 10 carbon atoms or a branched or cyclic alkyl group having 3 to 10 carbon atoms, or an aromatic or heteroaromatic ring system having 6 to 25 aromatic ring atoms, where the alkyl and alkoxy groups mentioned and the aromatic or heteroaromatic ring systems mentioned may each be substituted by one or more $R^3$ radicals; preferably, $R^1$ is the same or different at each instance and is H, F, CN, methyl, tert-butyl, phenyl, biphenyl, dibenzofuran, dibenzothiophene or carbazole, even more preferably still H.

Examples of compounds according to present invention are:

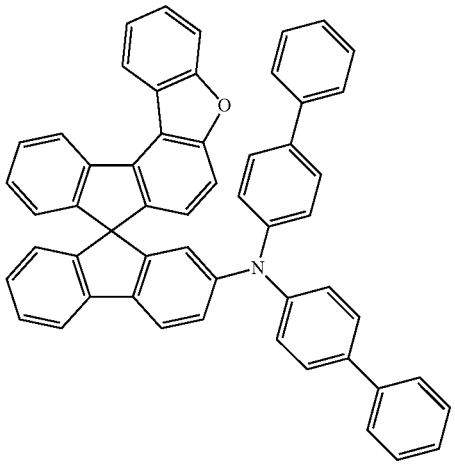

1

2
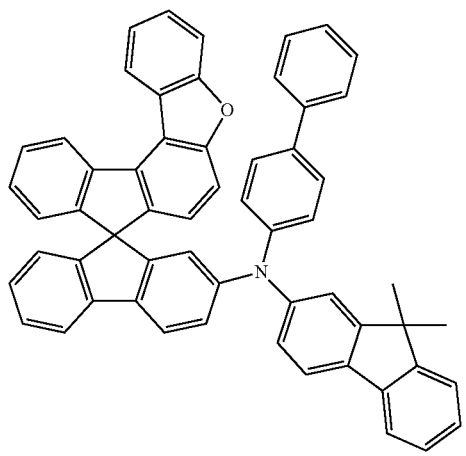
3
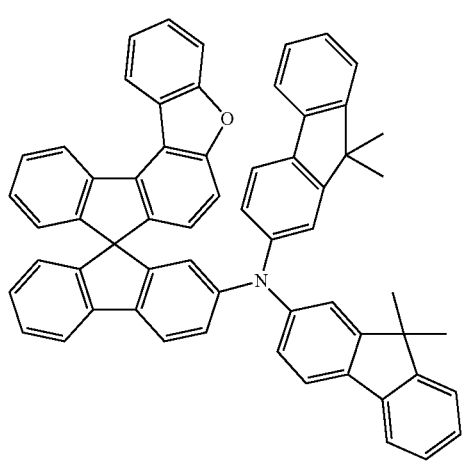
4
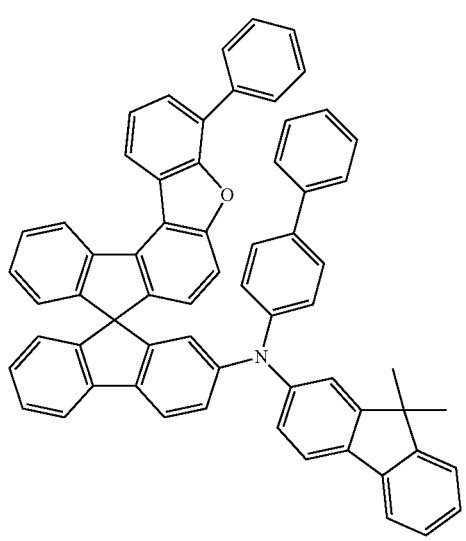
5
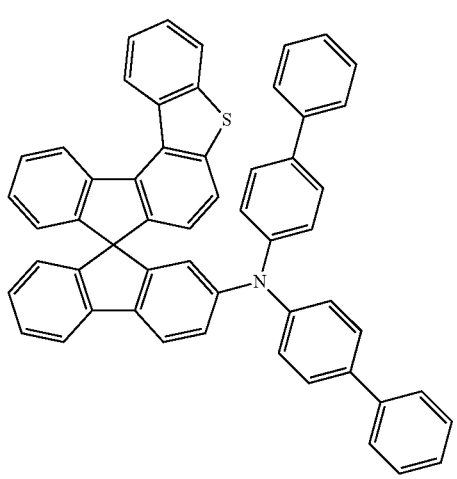
6
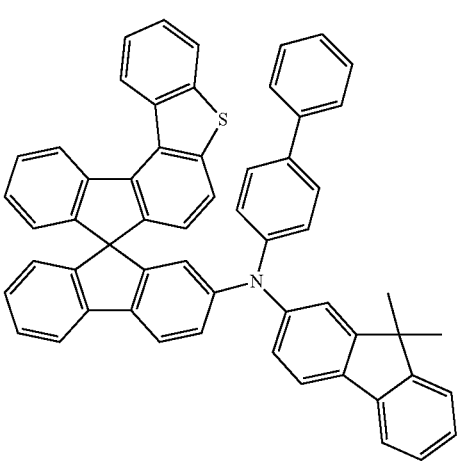
7
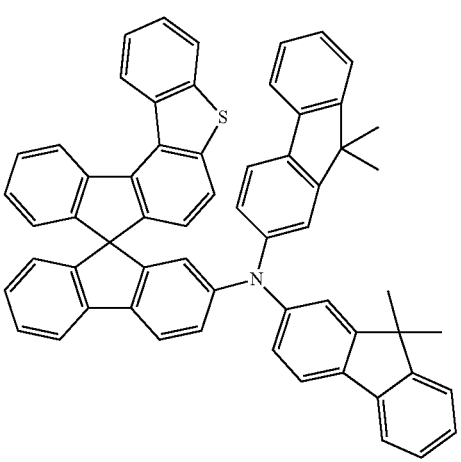

8
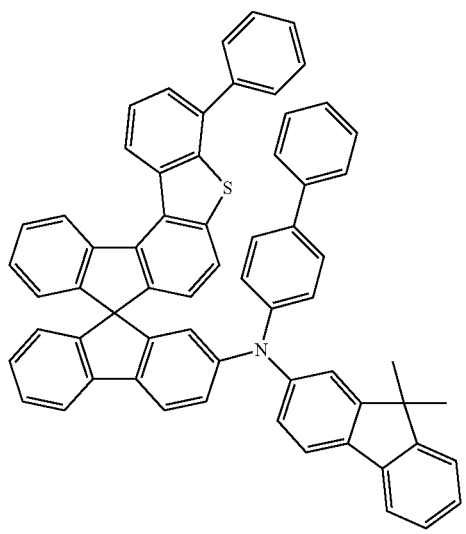
9
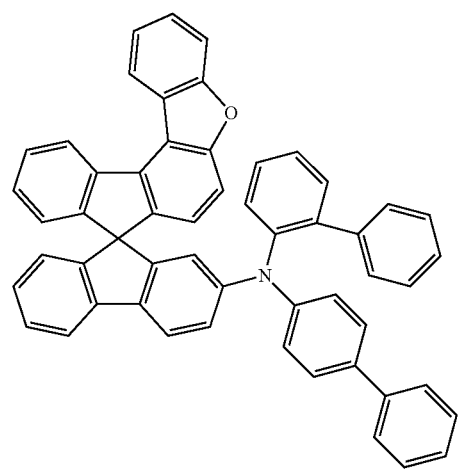
10
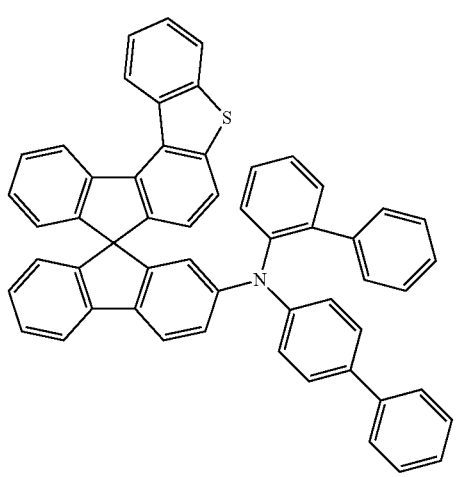
11
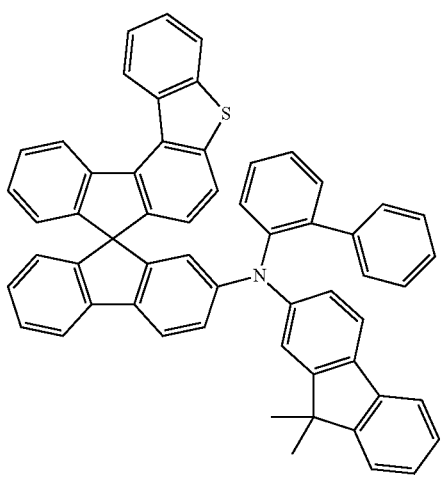
12
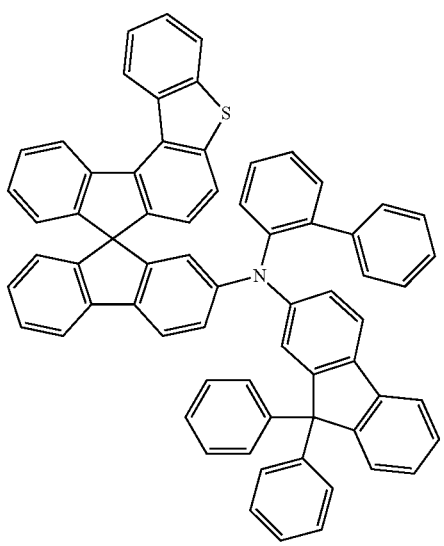
13
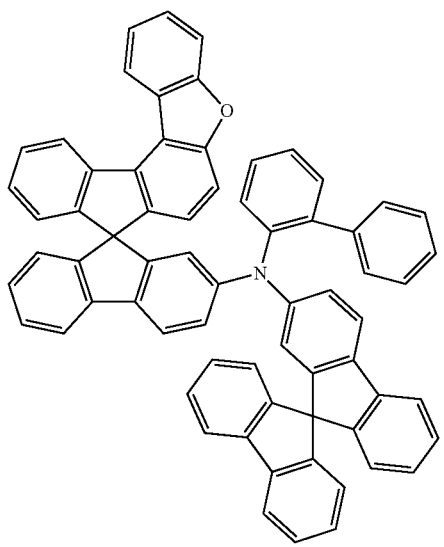

14
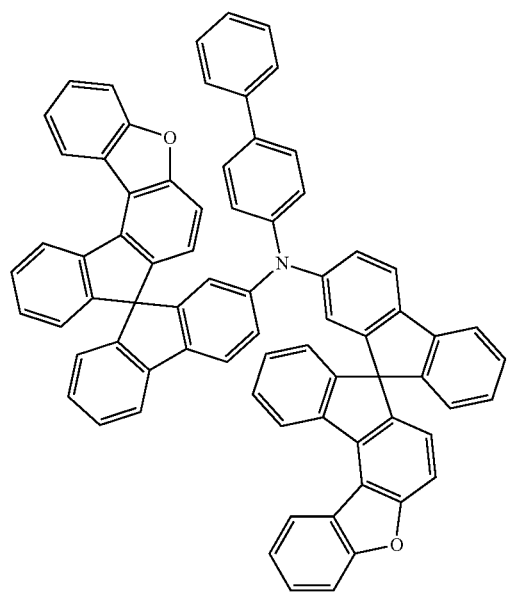
15
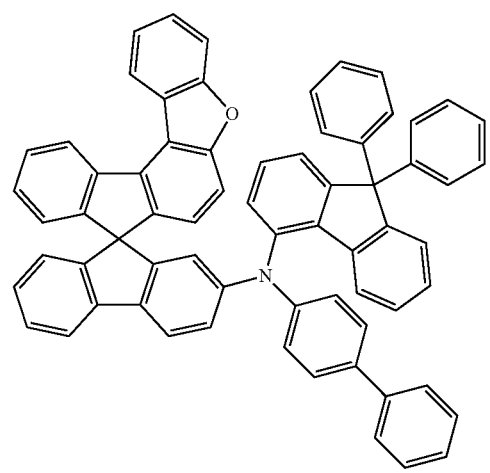
16
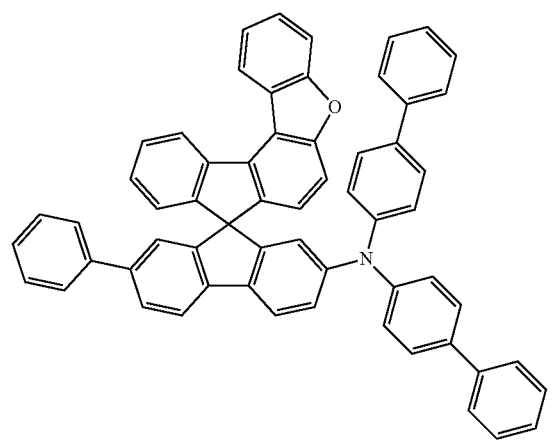
17
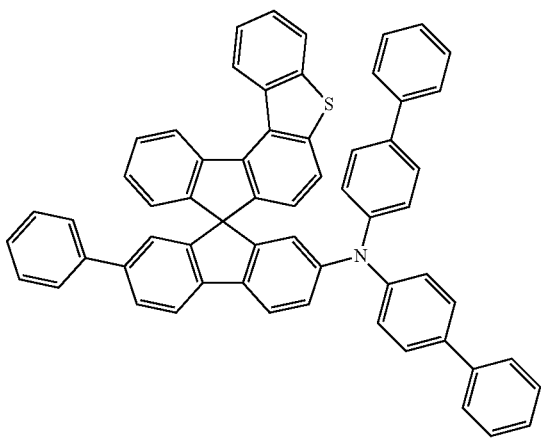
18
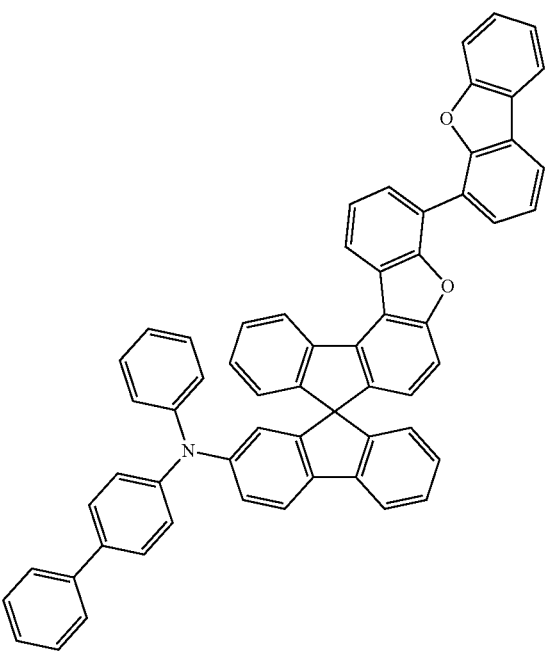
19
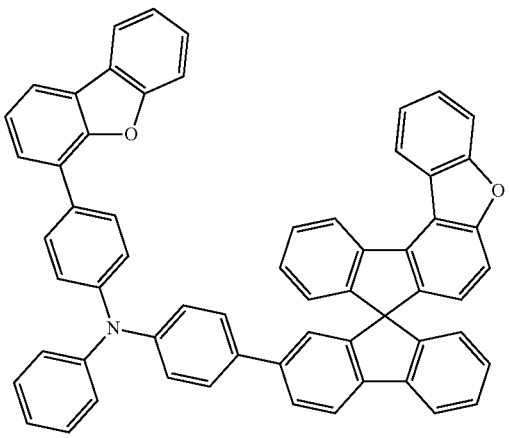

20
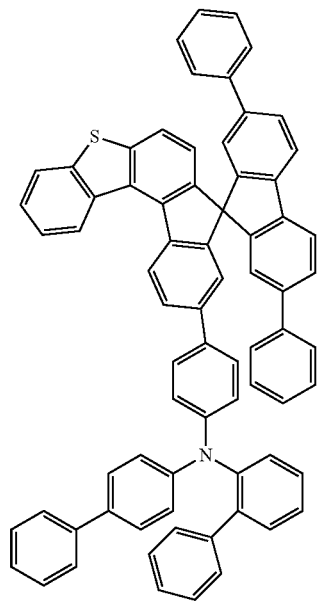
21
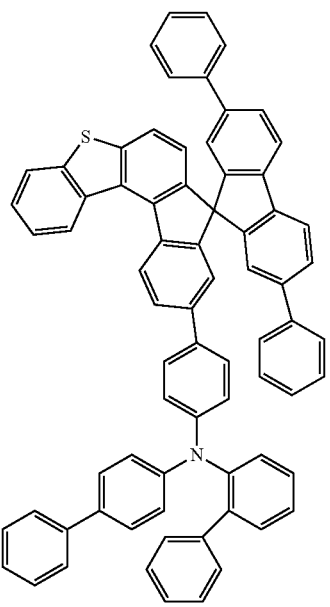
22
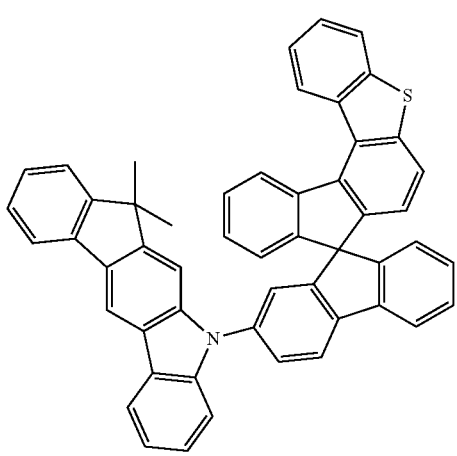
23
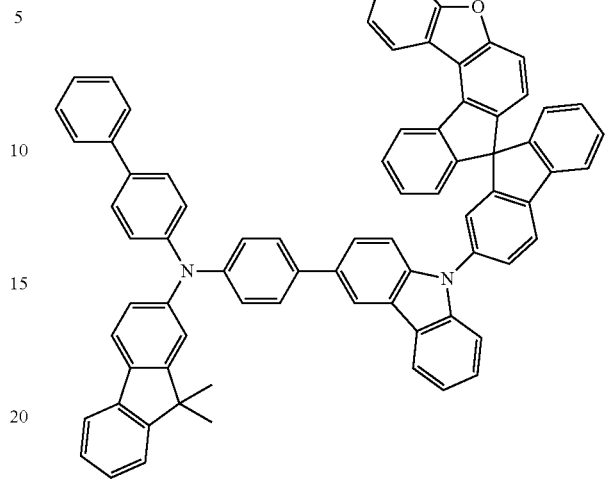
24
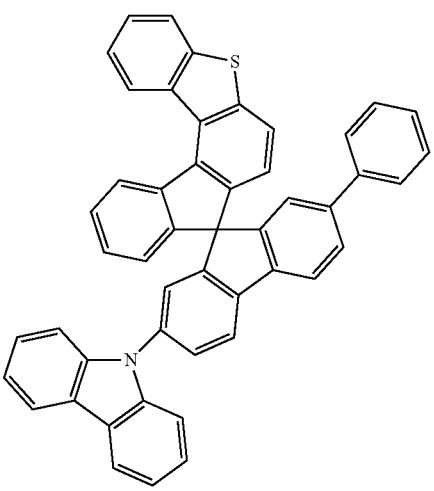
25
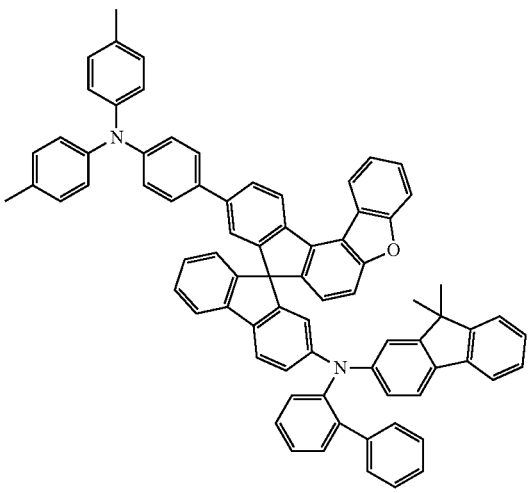

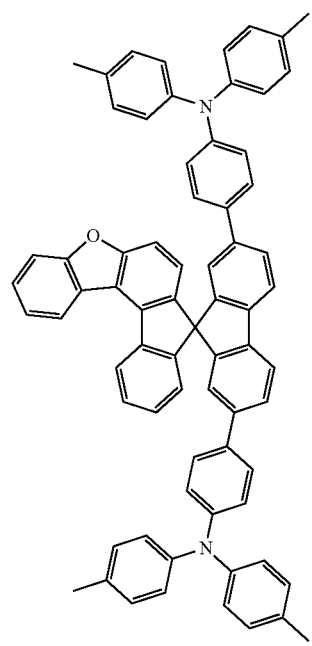
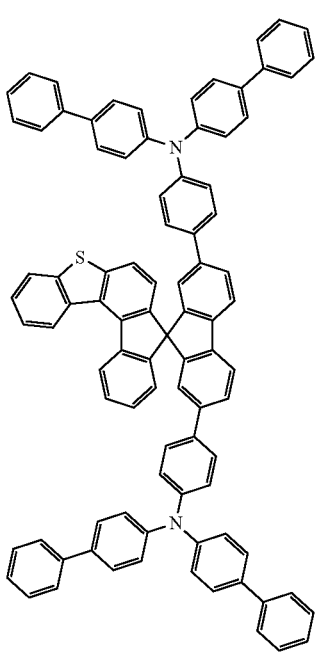
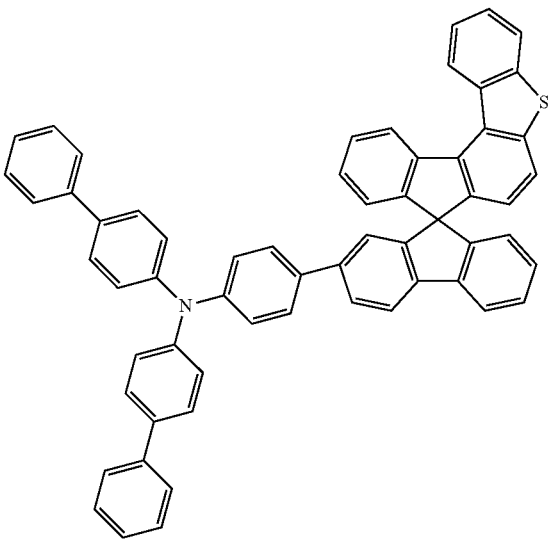

31
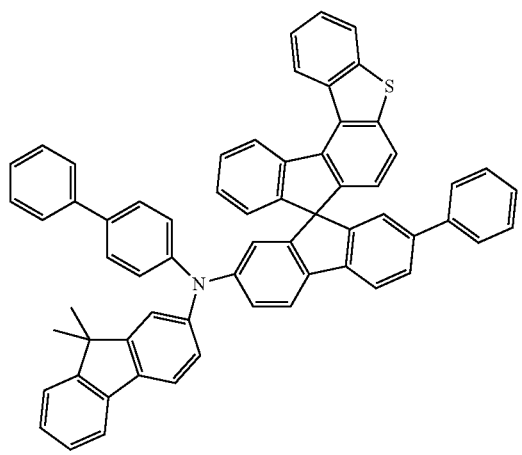
34
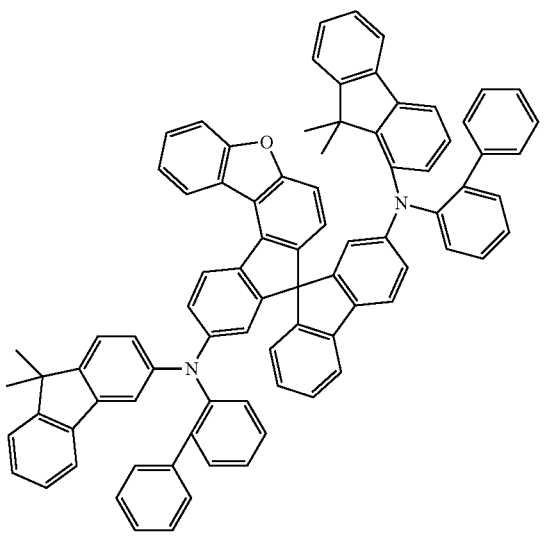
32
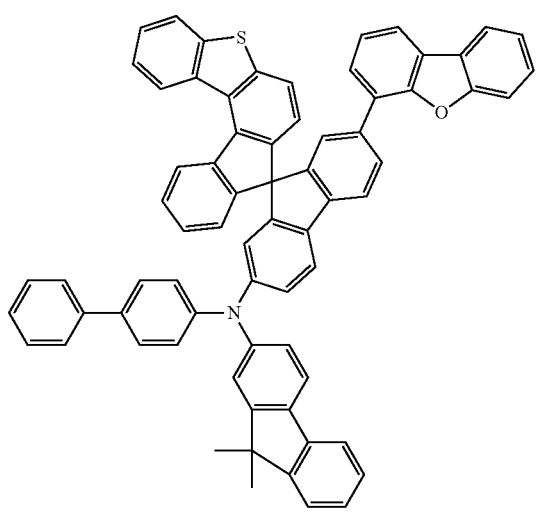
35
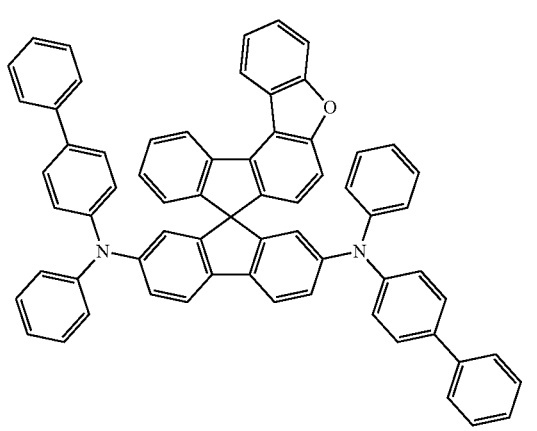
33
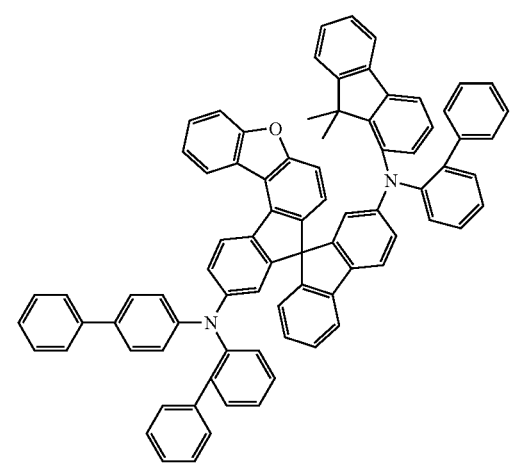
36
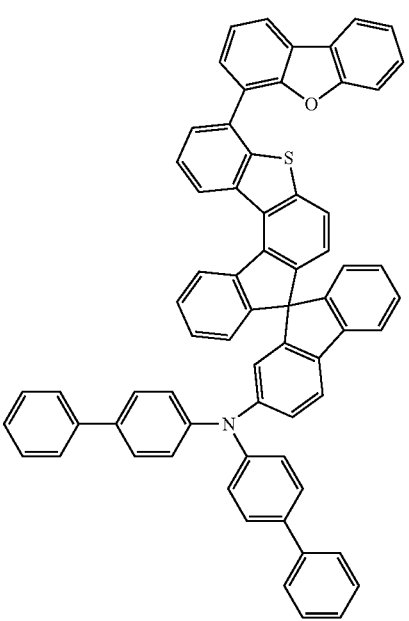

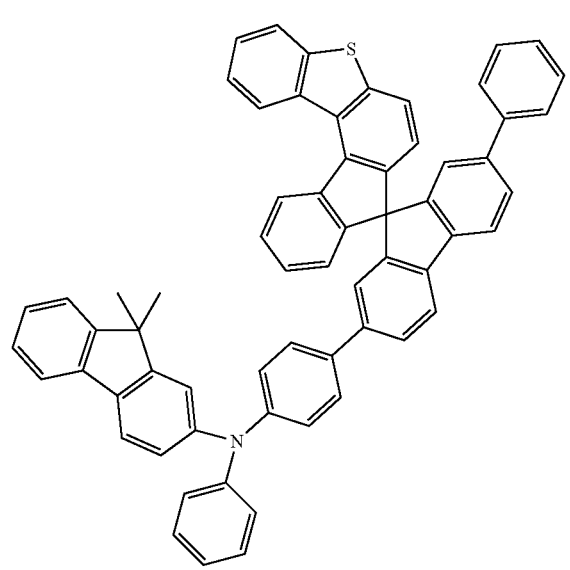
37
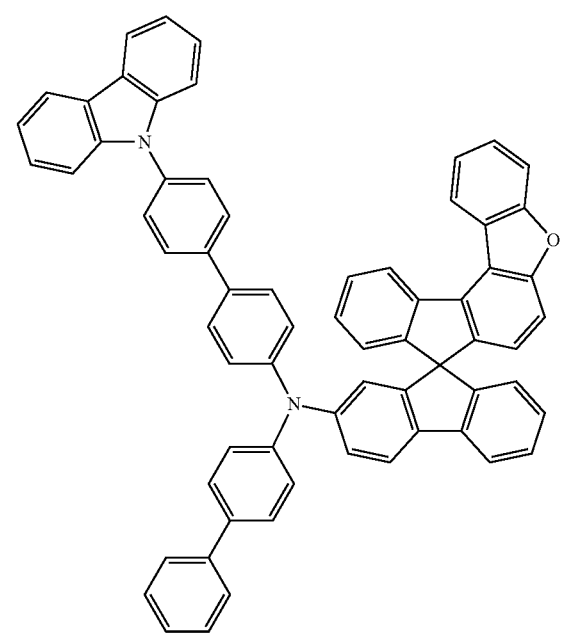
38
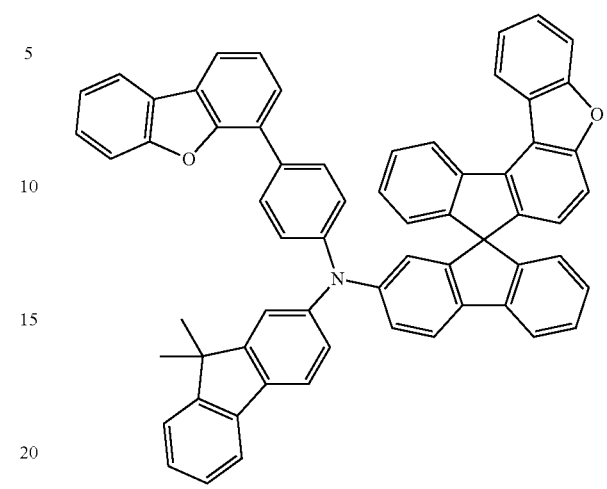
39
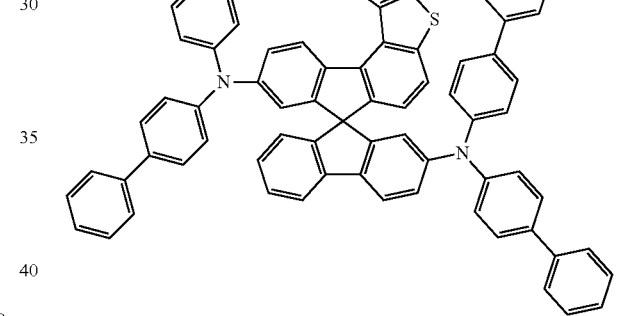
40
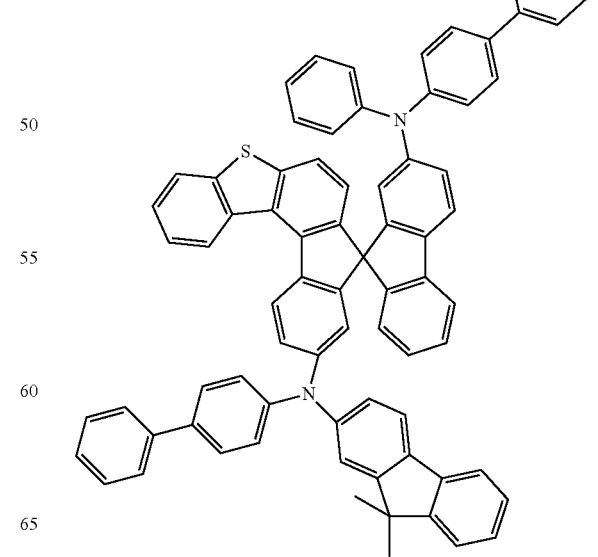
41

42
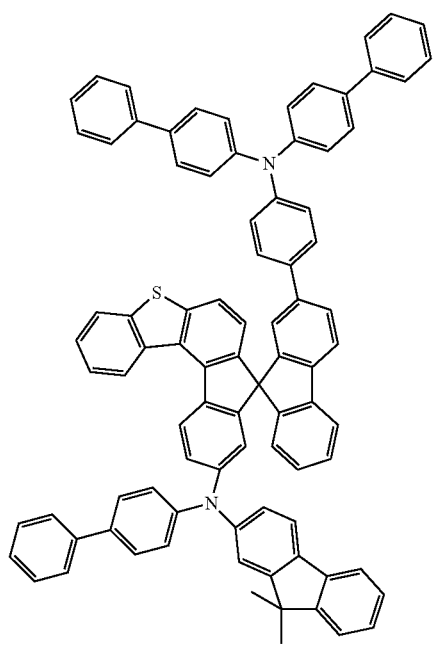
43
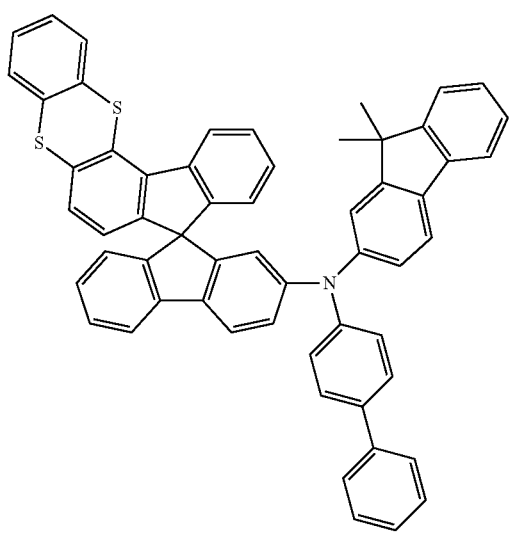
44
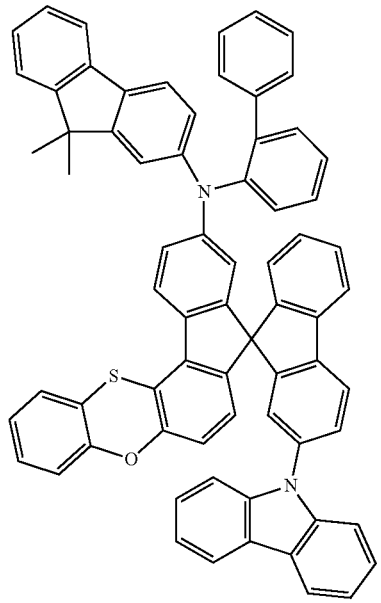
45
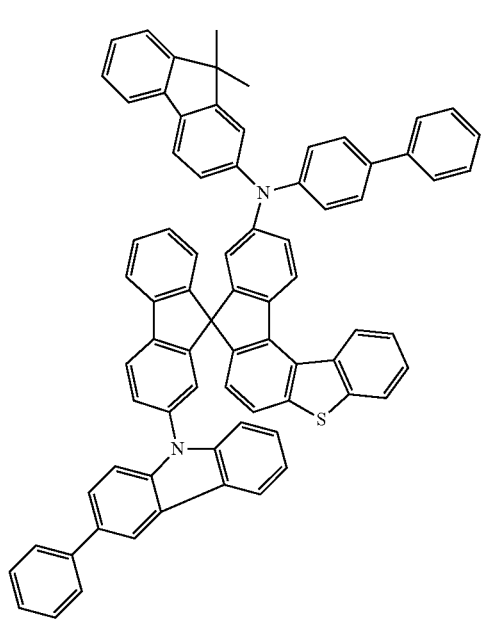

46
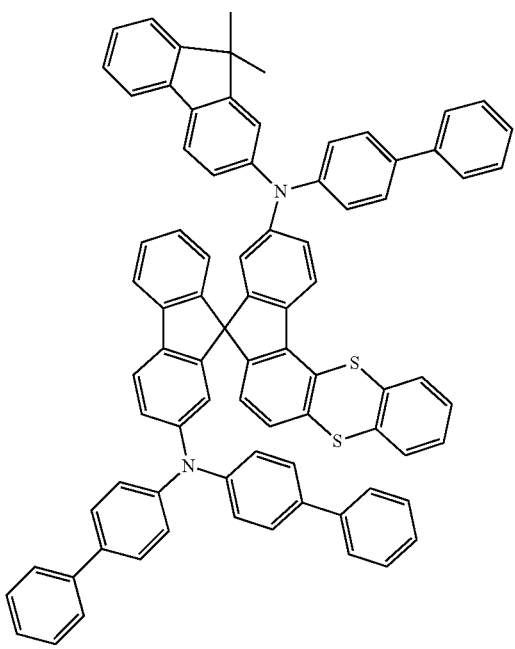
47
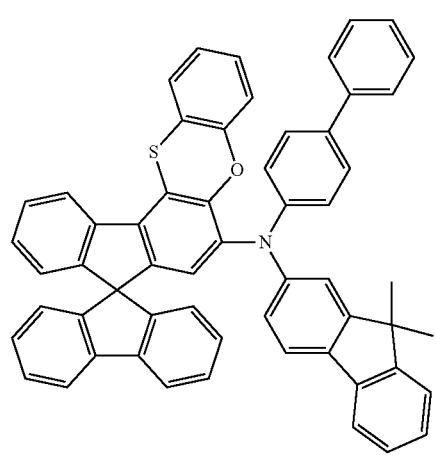
48
49
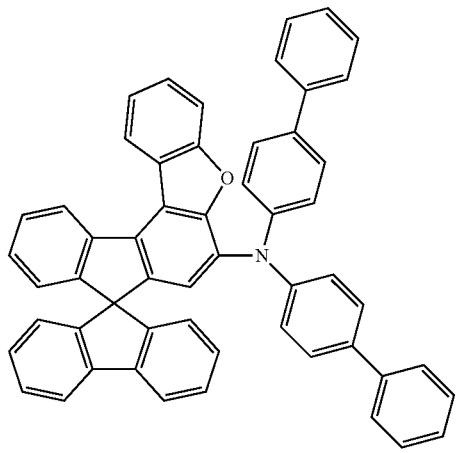
50
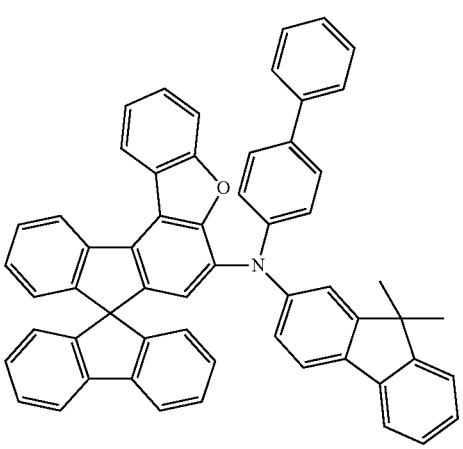
51
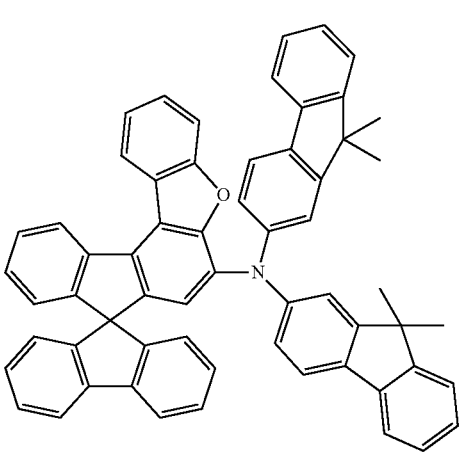

52
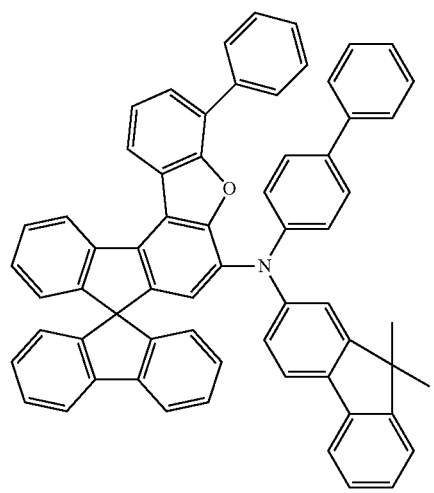
53
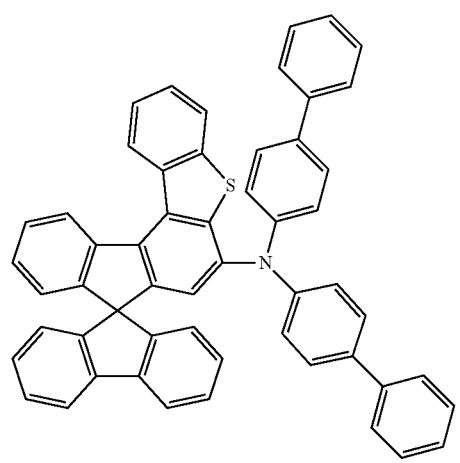
54
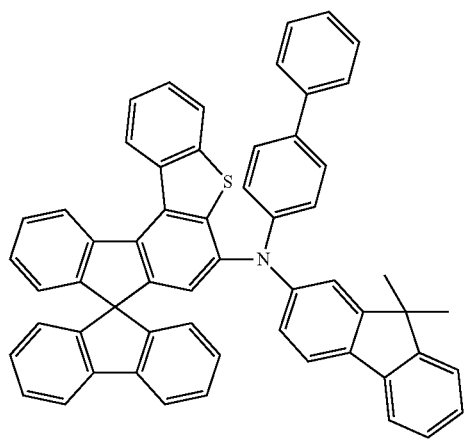
55
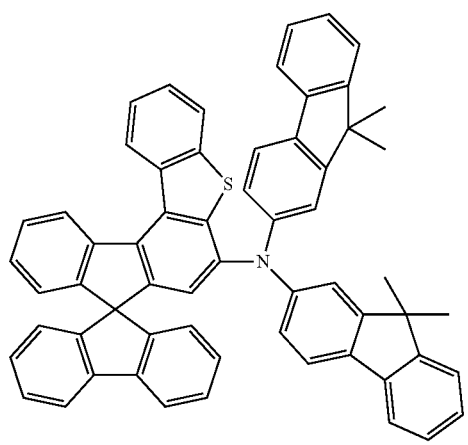
56
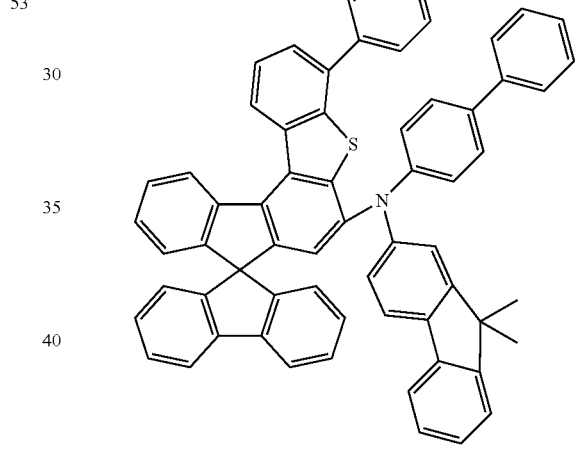
57
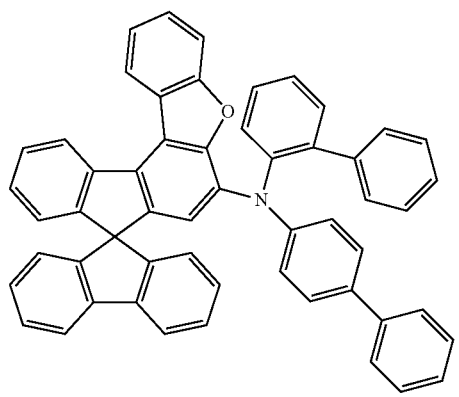

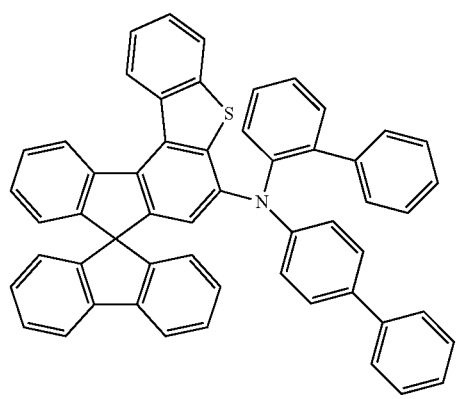
58
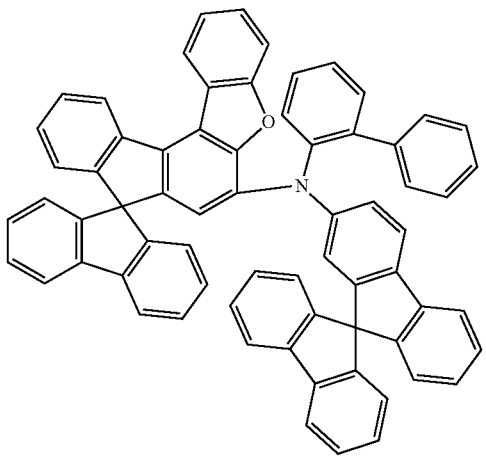
61
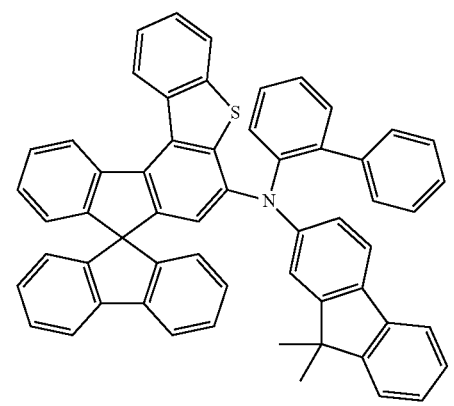
59
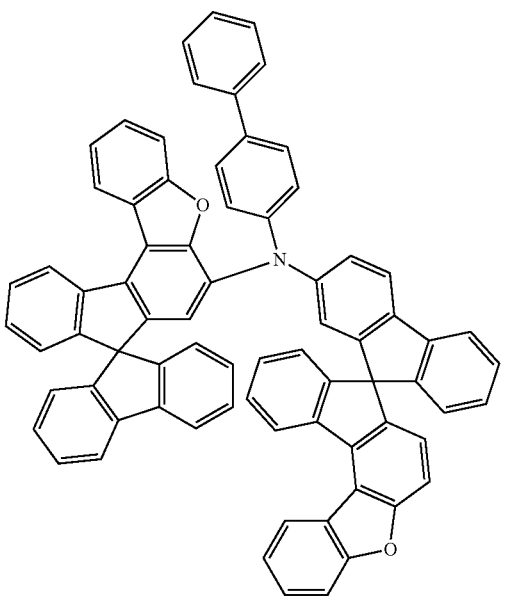
62
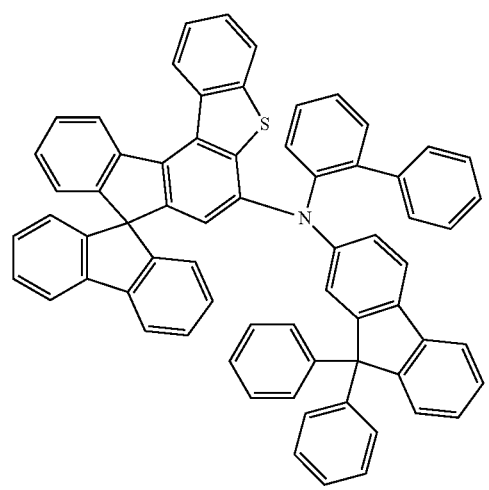
60
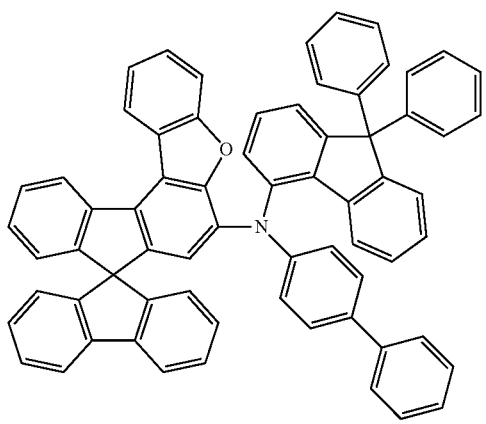
63

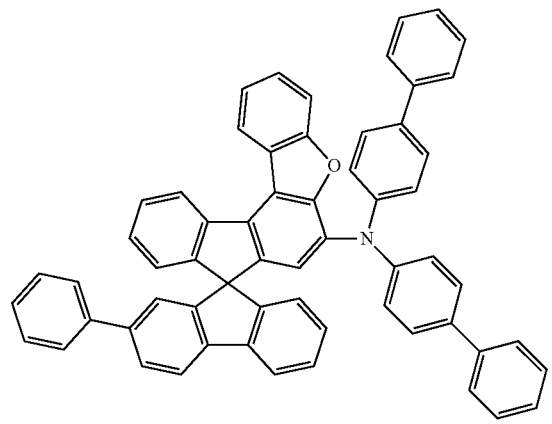
64
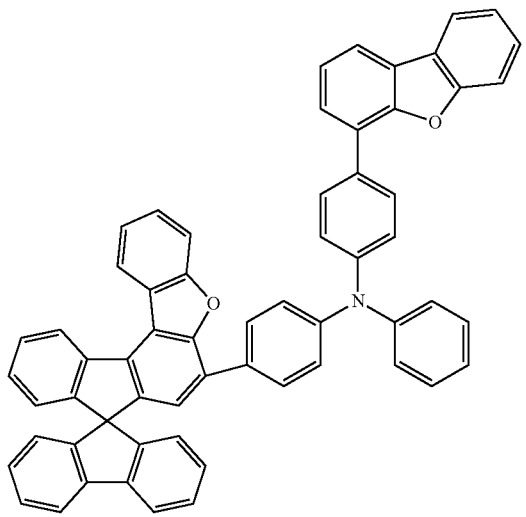
67
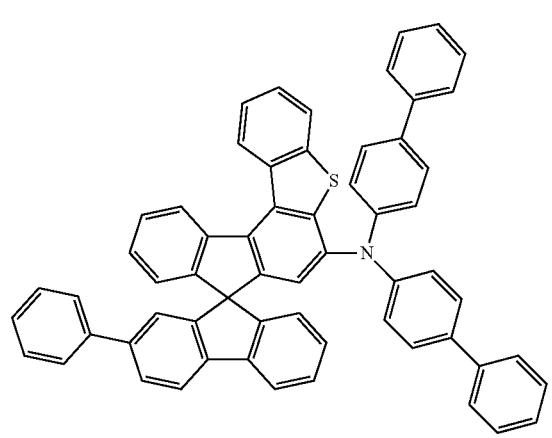
65
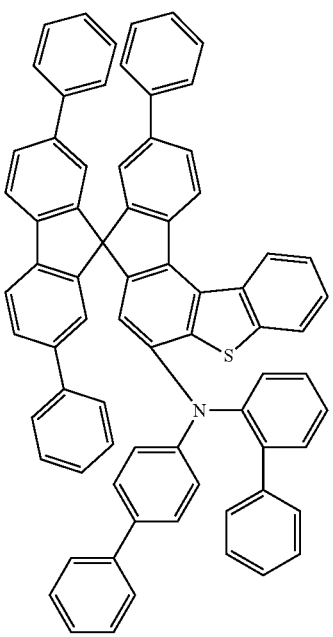
68
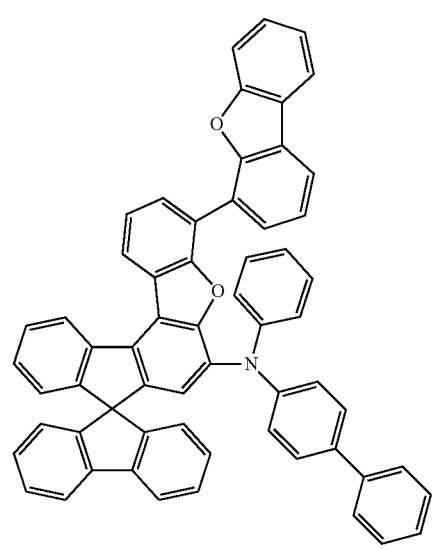
66
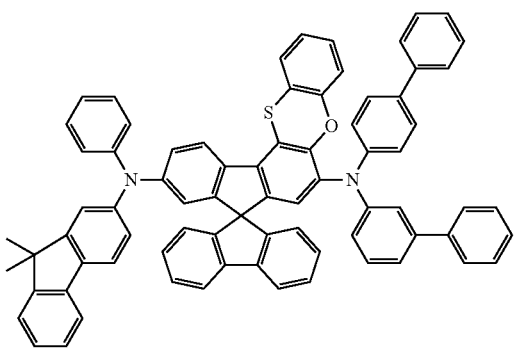
69

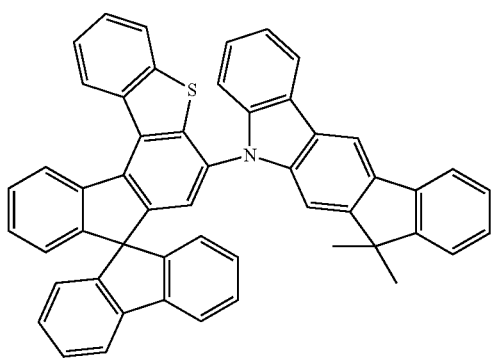
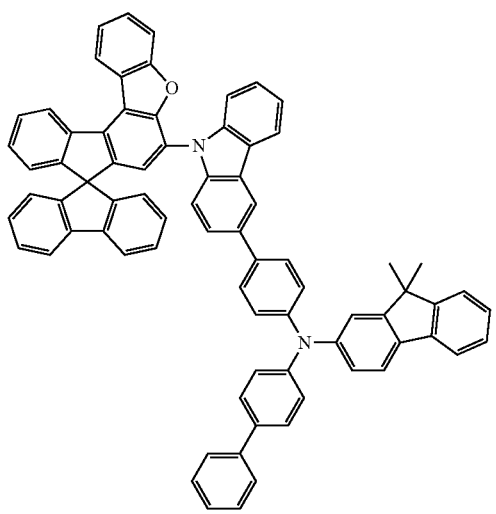
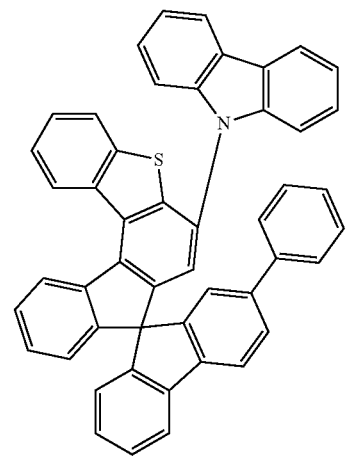
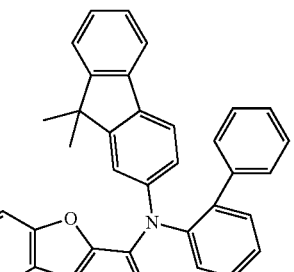
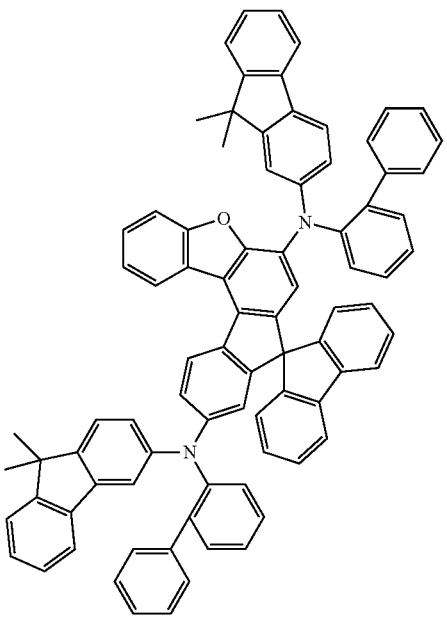
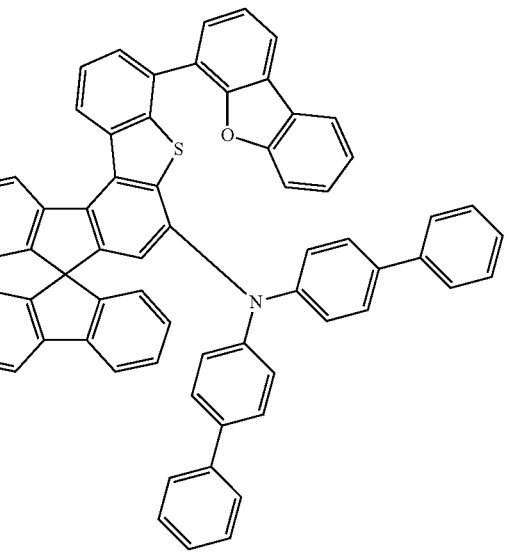

76
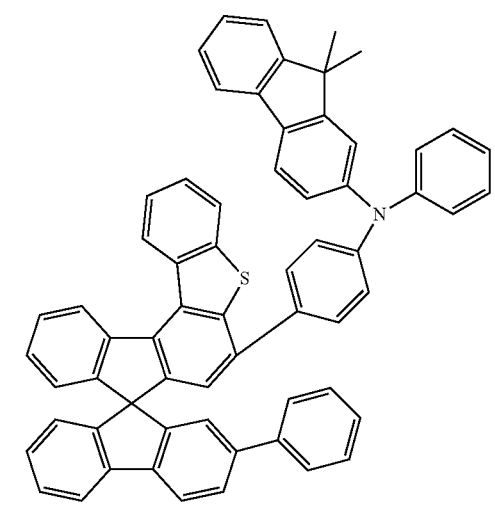
77
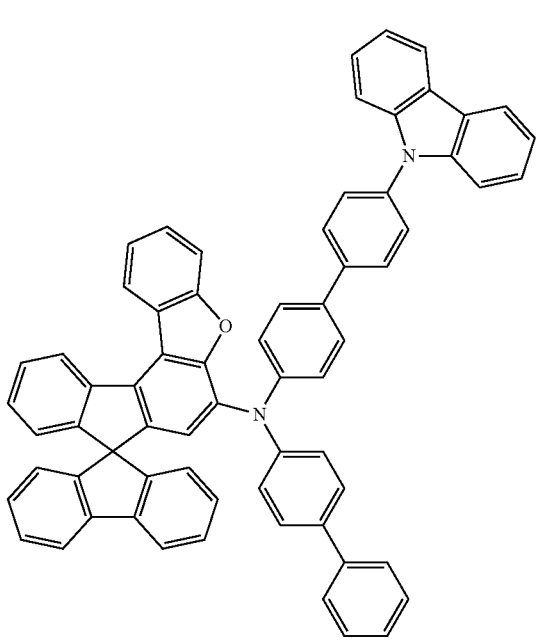
78
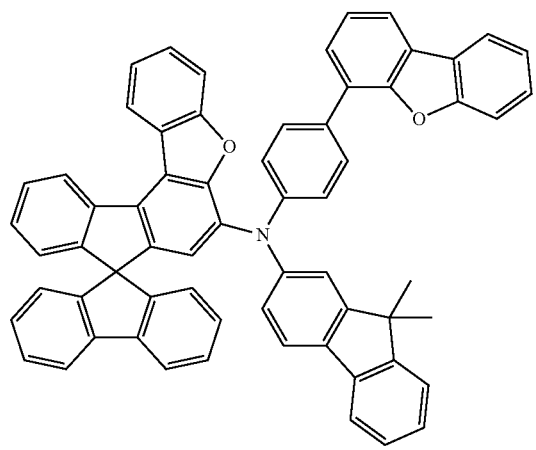
79
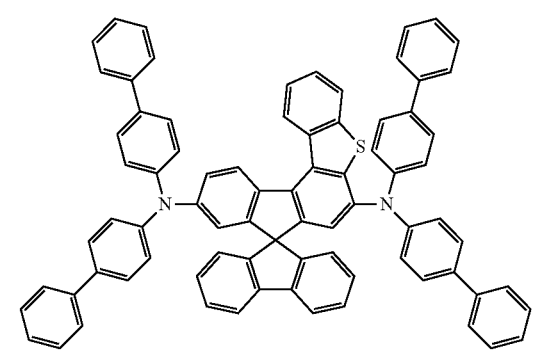
80
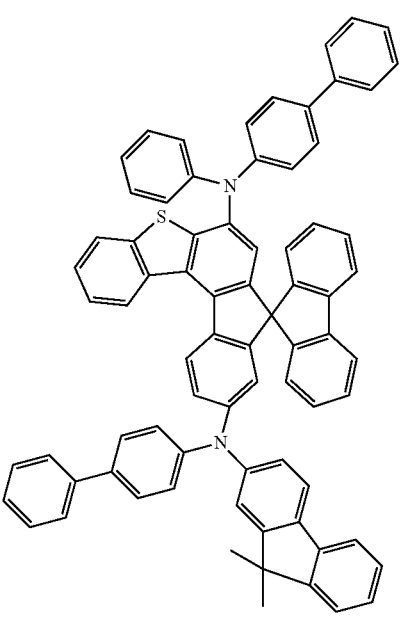
81
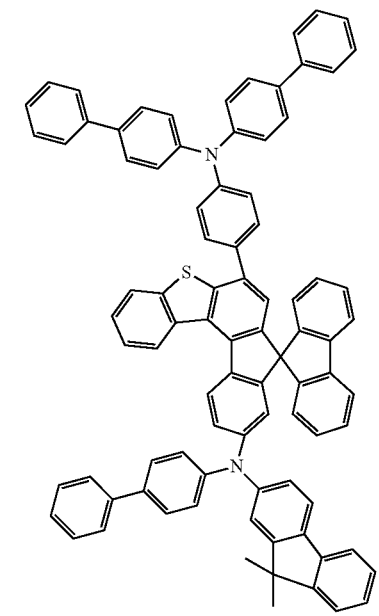

-continued

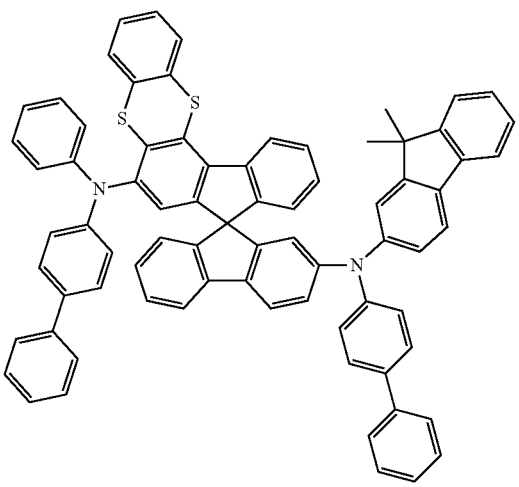
82

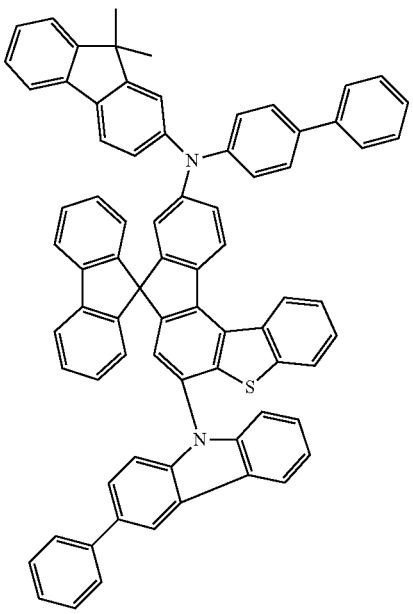
84

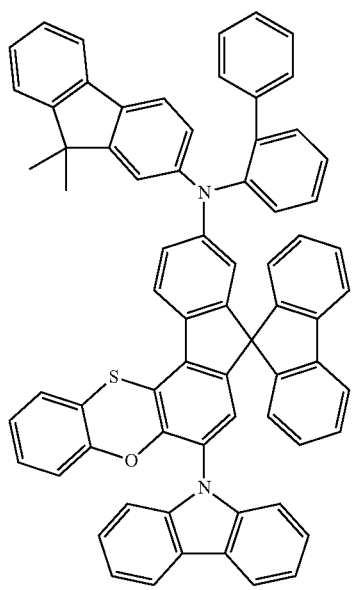
83

The synthesis of the compounds of formula (I) can be conducted using processes and reaction types known in the prior art, for example halogenation, organometallic addition, Buchwald coupling and Suzuki coupling.

Schemes 1 to 3 show possible synthesis routes for preparation of the inventive compounds. They serve to elucidate the invention to the person skilled in the art, and should not be interpreted in a restrictive manner. The person skilled in the art will be able, within the scope of his common knowledge in the art, to modify the synthesis routes shown, or to develop other routes if this appears to be more advantageous.

In the synthesis schemes that follow, the compounds are shown in unsubstituted form. This does not rule out the presence of any desired substituents in the processes.

Scheme 1 shows a suitable synthesis for the intermediate of formula (Z-I).

Scheme 1

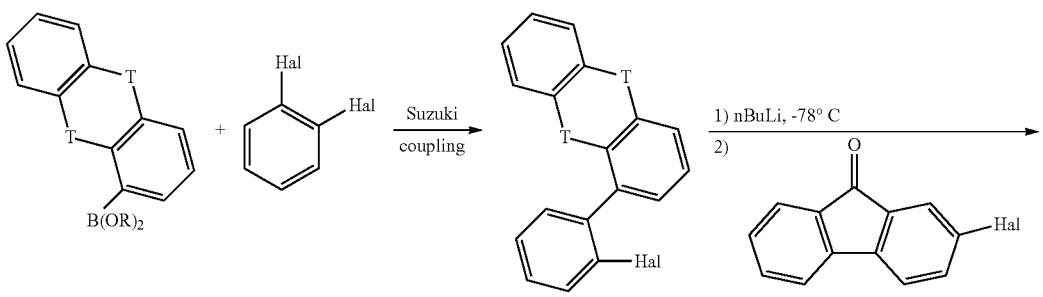

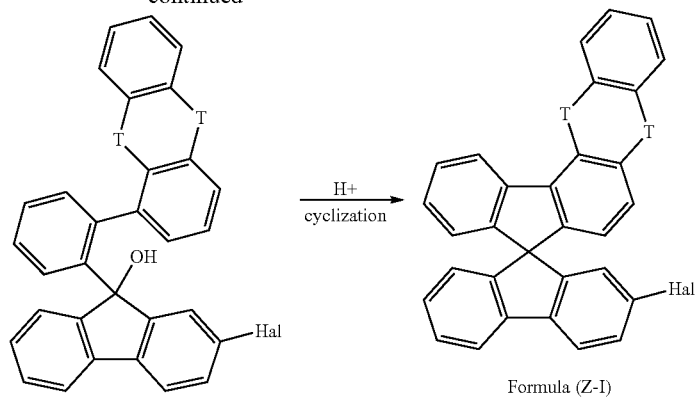
Formula (Z-I)
or other reactive group. preferably Cl, Br or I
R: organic radical or H
T: single bond or bridge, selected from O, S and Se
In an analogous manner, it is possible to prepare the intermediates of formula (Z-II) (Scheme 2).
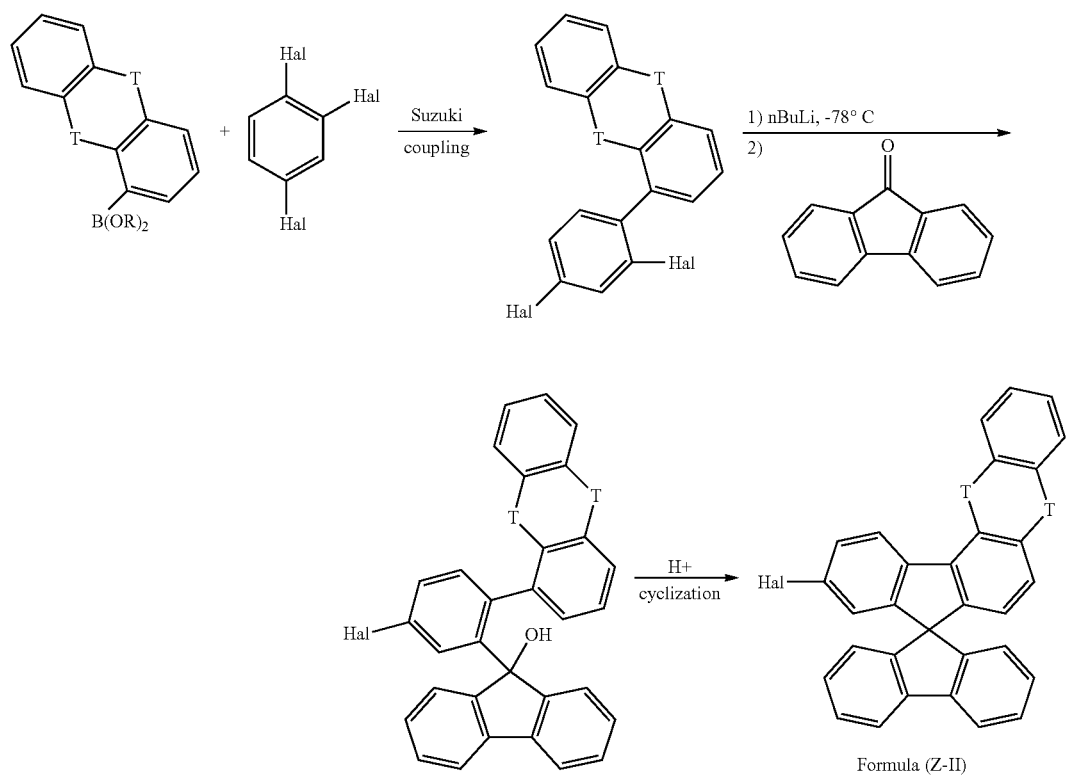
or other reactive group, preferably Cl, Br or I
R: organic radical or h
T: single bond or bridge, selected from O, S and Se By means of a modification of Scheme 1 or 2, it is possible to prepare Intermediates bearing two or more reactive Hal groups. For this purpose, it is possible to use either a Hal-substituted fluorenone unit or a phenyl group substituted by three Hal groups. Alternatively, it is also possible to use a fluorenone unit disubstituted or polysubstituted by Hal.

The intermediates provided with reactive Z groups according to the formulae (Z-I) and (Z-II) are versatile units which can be converted to compounds of the formula (I), as shown by the following scheme:

dendrimer may be localized at any desired positions substituted by $R^1$ or $R^2$ in formula (I). According to the linkage of the compound of formula (I), the compound is part of a side chain of the oligomer or polymer or part of the main chain. An oligomer in the context of the invention is understood to mean a compound formed from at least three monomer units. A polymer in the context of the invention is understood to mean a compound formed from at least ten monomer units. The inventive polymers, oligomers or dendrimers may be conjugated, partly conjugated or nonconjugated. The inventive oligomers or polymers may be linear, branched or

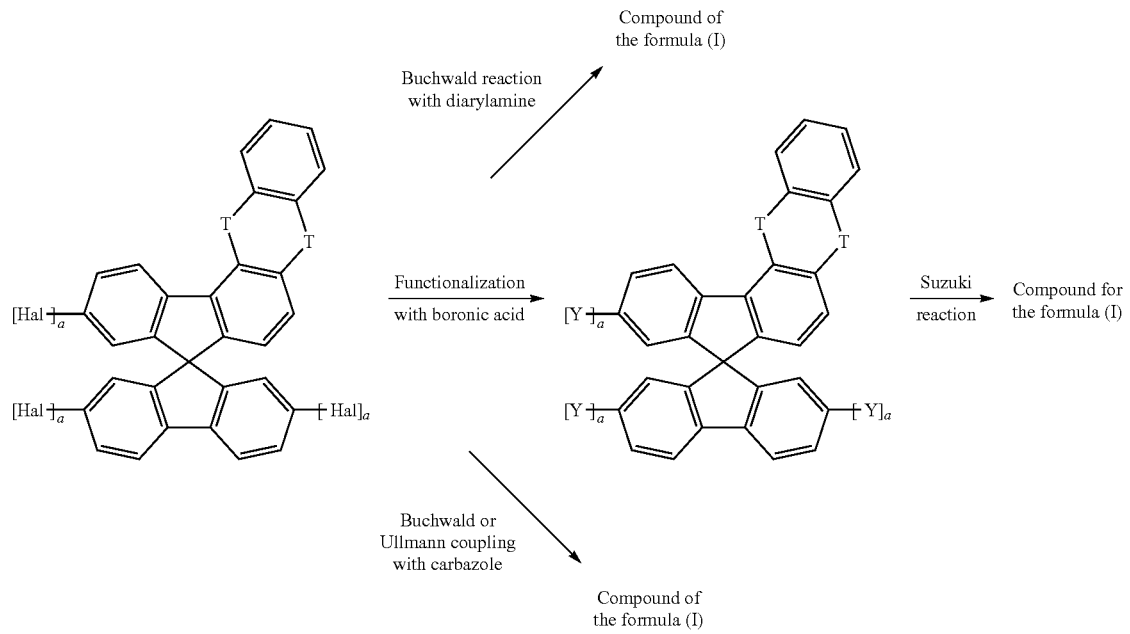

Scheme 3

Hal = halogen or other reactive functional group
T = single bond or divalent group selected from the O, S and Se
Y = boronic acid or derivative The present application therefore also provides a process for preparing compounds of formula (I), characterized in that
first the spirobifluorene base skeleton is prepared and, in a later step, via an organometallic coupling reaction, an arylamino or carbazole group or an aryl or heteroaryl group substituted by an arylamino or carbazole group is introduced.

The organometallic coupling reaction is preferably a Buchwald coupling or a Suzuki coupling.

The above-described compounds, especially compounds substituted by reactive leaving groups, such as bromine, iodine, chlorine, boronic acid or boronic ester, may find use as monomers for production of corresponding oligomers, dendrimers or polymers. Suitable reactive leaving groups are, for example, bromine, iodine, chlorine, boronic acids, boronic esters, amines, alkenyl or alkynyl groups having a terminal C=C double bond or C—C triple bond, oxiranes, oxetanes, groups which enter into a cycloaddition, for example a 1,3-dipolar cycloaddition, for example dienes or azides, carboxylic acid derivatives, alcohols and silanes.

The invention therefore further provides oligomers, polymers or dendrimers containing one or more compounds of formula (I), wherein the bond(s) to the polymer, oligomer or dendritic. In the structures having linear linkage, the units of formula (I) may be joined directly to one another, or they may be joined to one another via a bivalent group, for example via a substituted or unsubstituted alkylene group, via a heteroatom or via a bivalent aromatic or heteroaromatic group. In branched and dendritic structures, it is possible, for example, for three or more units of formula (1) to be joined by a trivalent or higher-valency group, for example via a trivalent or higher-valency aromatic or heteroaromatic group, to give a branched or dendritic oligomer or polymer.

For the repeat units of formula (I) in oligomers, dendrimers and polymers, the same preferences apply as described above for compounds of formula (I).

For preparation of the oligomers or polymers, the monomers of the invention are homopolymerized or copolymerized with further monomers. Suitable and preferred comonomers are chosen from fluorenes (for example according to EP 842208 or WO 2000/22026), spirobifluorenes (for example according to EP 707020, EP 894107 or WO 2006/061181), paraphenylenes (for example according to WO 1992/18552), carbazoles (for example according to WO 2004/070772 or WO 2004/113468), thiophenes (for example according to EP 1028136), dihydrophenanthrenes (for example according to WO 2005/014689 or WO 2007/006383), cis- and trans-indenofluorenes (for example according to WO 2004/041901 or WO 2004/113412), ketones (for example according to WO 2005/040302), phenanthrenes (for example according to WO 2005/104264 or WO 2007/017066) or else a plurality of these units. The polymers, oligomers and dendrimers typically contain still further units, for example emitting (fluorescent or phosphorescent) units, for example vinyltriarylamines (for example according to WO 2007/068325) or phosphorescent metal complexes (for example according to WO 2006/003000), and/or charge transport units, especially those based on triarylamines.

The inventive polymers and oligomers are generally prepared by polymerization of one or more monomer types, of which at least one monomer leads to repeat units of the formula (I) in the polymer. Suitable polymerization reactions are known to those skilled in the art and are described in the literature. Particularly suitable and preferred polymerization reactions which lead to formation of C—C or C—N bonds are the SUZUKI polymerization, the YAMAMOTO polymerization, the STILLE polymerization and the HARTWIG-BUCHWALD polymerization.

For the processing of the inventive compounds from the liquid phase, for example by spin-coating or by printing methods, formulations of the inventive compounds are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The invention therefore further provides a formulation, especially a solution, dispersion or emulsion, comprising at least one compound of formula (I) and at least one solvent, preferably an organic solvent. The way in which such solutions can be prepared is known to those skilled in the art and is described, for example, in WO 2002/072714, WO 2003/019694 and the literature cited therein.

The inventive compounds are suitable for use in electronic devices, especially in organic electroluminescent devices (OLEDs). Depending on the substitution, the compounds are used in different functions and layers.

The invention therefore further provides for the use of the compound of formula (I) in an electronic device. This electronic device is preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and more preferably organic electroluminescent devices (OLEDs).

The invention further provides, as already set out above, an electronic device comprising at least one compound of formula (I). This electronic device is preferably selected from the abovementioned devices.

It is more preferably an organic electroluminescent device (OLED) comprising anode, cathode and at least one emitting layer, characterized in that at least one organic layer, which may be an emitting layer, a hole transport layer or another layer, comprises at least one compound of formula (I).

Apart from the cathode, anode and emitting layer, the organic electroluminescent device may also comprise further layers. These are selected, for example, from in each case one or more hole injection layers, hole transport layers, hole blocker layers, electron transport layers, electron injection layers, electron blocker layers, exciton blocker layers, interlayers, charge generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions.

The sequence of the layers of the organic electroluminescent device comprising the compound of the formula (I) is preferably as follows: anode-hole injection layer-hole transport layer-optionally further hole transport layer-optionally electron blocker layer-emitting layer-optionally hole blocker layer-electron transport layer-electron injection layer-cathode. It is additionally possible for further layers to be present in the OLED.

The inventive organic electroluminescent device may contain two or more emitting layers. More preferably, these emission layers in this case have several emission maxima between 380 nm and 750 nm overall, such that the overall result is white emission; in other words, various emitting compounds which may fluoresce or phosphoresce and which emit blue, green, yellow, orange or red light are used in the emitting layers. Especially preferred are three-layer systems, i.e. systems having three emitting layers, where the three layers show blue, green and orange or red emission (for the basic construction see, for example, WO 2005/011013). The inventive compounds are preferably present in the hole transport layer, hole injection layer or electron blocker layer.

It is preferable in accordance with the invention when the compound of formula (I) is used in an electronic device comprising one or more phosphorescent emitting compounds. In this case, the compound may be present in different layers, preferably in a hole transport layer, an electron blocker layer, a hole injection layer or an emitting layer.

The term "phosphorescent emitting compounds" typically encompasses compounds where the emission of light is effected through a spin-forbidden transition, for example a transition from an excited triplet state or a state having a higher spin quantum number, for example a quintet state.

Suitable phosphorescent emitting compounds (=triplet emitters) are especially compounds which, when suitably excited, emit light, preferably in the visible region, and also contain at least one atom of atomic number greater than 20, preferably greater than 38, and less than 84, more preferably greater than 56 and less than 80. Preference is given to using, as phosphorescent emitting compounds, compounds containing copper, molybdenum, tungsten, rhenium, ruthenium, osmium, rhodium, iridium, palladium, platinum, silver, gold or europium, especially compounds containing iridium, platinum or copper. In the context of the present invention, all luminescent iridium, platinum or copper complexes are considered to be phosphorescent emitting compounds.

Examples of the above-described emitting compounds can be found in applications WO 00/70655, WO 01/41512, WO 02/02714, WO 02/15645, EP 1191613, EP 1191612, EP 1191614, WO 05/033244, WO 05/019373 and US 2005/0258742. In general, all phosphorescent complexes as used for phosphorescent OLEDs according to the prior art and as known to those skilled in the art in the field of organic electroluminescent devices are suitable. It is also possible for the person skilled in the art, without exercising inventive skill, to use further phosphorescent complexes in combination with the compounds of formula (I) in organic electroluminescent devices. Further examples are listed in a table which follows.

It is also possible in accordance with the invention to use the compound of formula (I) in an electronic device comprising one or more fluorescent emitting compounds.

In a preferred embodiment of the invention, the compounds of formula (I) are used as hole transport material. In that case, the compounds are preferably present in a hole transport layer, an electron blocker layer or a hole injection layer. Particular preference is given to use in an electron blocker layer.

A hole transport layer according to the present application is a layer having a hole-transporting function between the anode and emitting layer.

Hole injection layers and electron blocker layers are understood in the context of the present application to be specific embodiments of hole transport layers. A hole injection layer, in the case of a plurality of hole transport layers between the anode and emitting layer, is a hole transport layer which directly adjoins the anode or is separated therefrom only by a single coating of the anode. An electron blocker layer, in the case of a plurality of hole transport layers between the anode and emitting layer, is that hole transport layer which directly adjoins the emitting layer on the anode side.

If the compound of formula (I) is used as hole transport material in a hole transport layer, a hole injection layer or an electron blocker layer, the compound can be used as pure material, i.e. in a proportion of 100%, in the hole transport layer, or it can be used in combination with one or more further compounds. In a preferred embodiment, the organic layer containing the compound of the formula (I) then additionally contains one or more p-dopants. p-Dopants used according to the present invention are preferably those organic electron acceptor compounds capable of oxidizing one or more of the other compounds in the mixture.

Particularly preferred embodiments of p-dopants are the compounds disclosed in WO 2011/073149, EP 1968131, EP 2276085, EP 2213662, EP 1722602, EP 2045848, DE 102007031220, U.S. Pat. No. 8,044,390, U.S. Pat. No. 8,057,712, WO 2009/003455, WO 2010/094378, WO 2011/120709, US 2010/0096600, WO 2012/095143 and DE 102012209523.

Particularly preferred p-dopants are quinodimethane compounds, azaindenofluorenediones, azaphenalenes, azatriphenylenes, $I_2$, metal halides, preferably transition metal halides, metal oxides, preferably metal oxides containing at least one transition metal or a metal of main group 3, and transition metal complexes, preferably complexes of Cu, Co, Ni, Pd and Pt with ligands containing at least one oxygen atom as bonding site. Preference is further given to transition metal oxides as dopants, preferably oxides of rhenium, molybdenum and tungsten, more preferably $Re_2O_7$, $MoO_3$, $WO_3$ and $ReO_3$.

The p-dopants are preferably in substantially homogeneous distribution in the p-doped layers. This can be achieved, for example, by coevaporation of the p-dopant and the hole transport material matrix.

Preferred p-dopants are especially the following compounds:

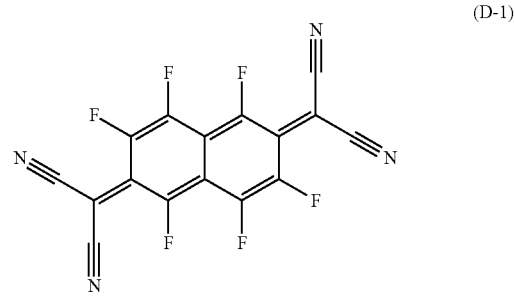

(D-1)

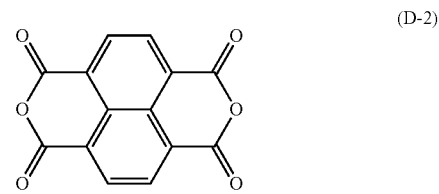

(D-2)

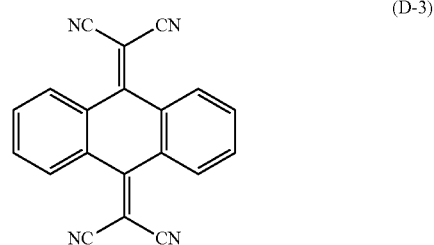

(D-3)

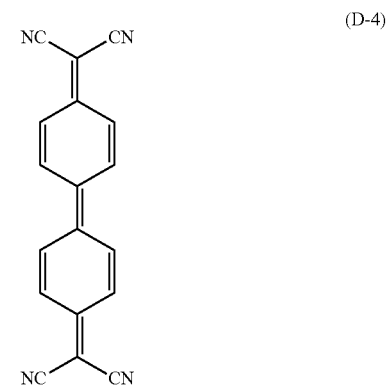

(D-4)

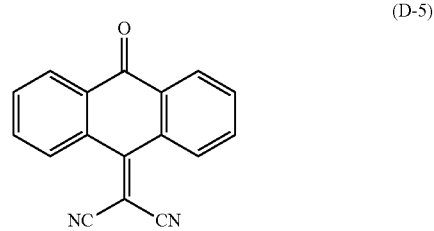

(D-5)

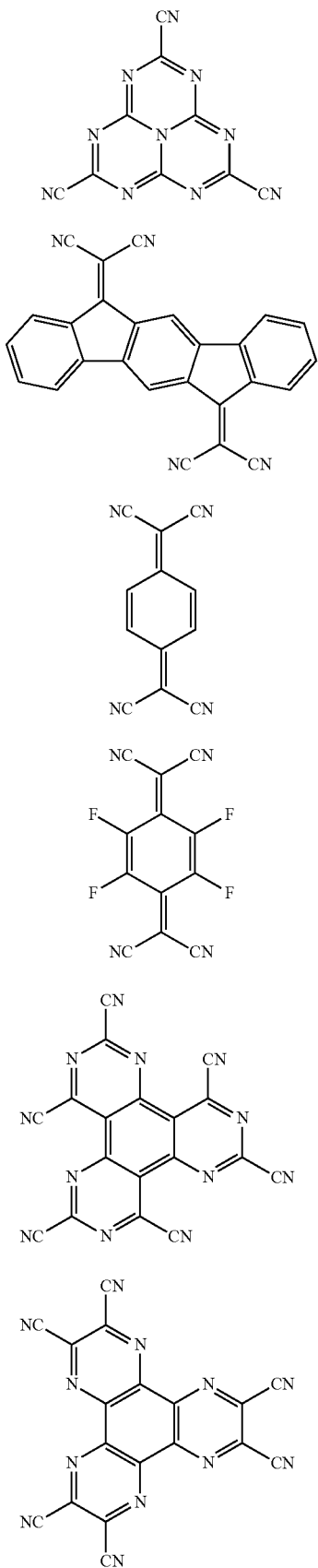

(D-6)
(D-7)
(D-8)
(D-9)
(D-10)
(D-11)

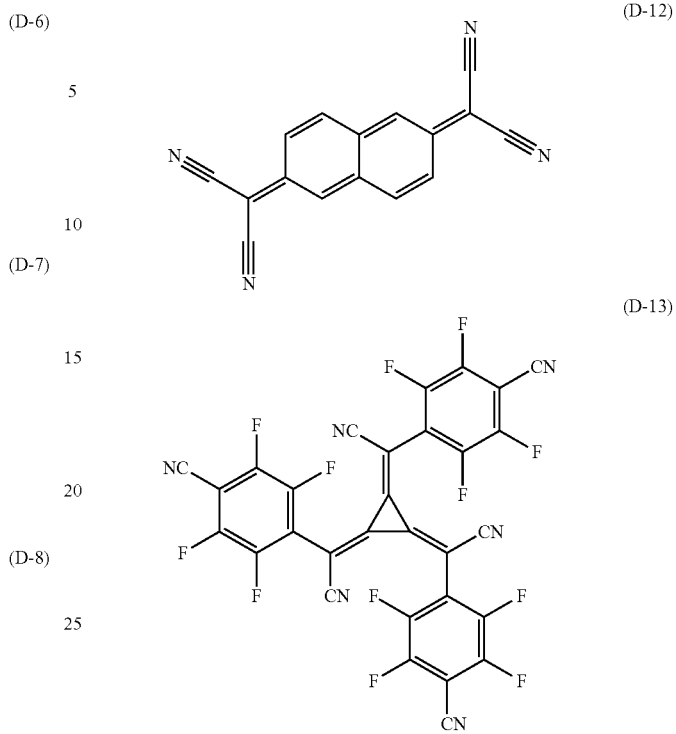

(D-12)
(D-13)

In a further preferred embodiment of the invention, the compound of formula (I) is used as hole transport material in combination with a hexaazatriphenylene derivative as described in US 2007/0092755. Particular preference is given here to using the hexaazatriphenylene derivative in a separate layer.

In a further embodiment of the present invention, the compound of the formula (I) is used in an emitting layer as matrix material in combination with one or more emitting compounds, preferably phosphorescent emitting compounds.

The proportion of the matrix material in the emitting layer in this case is between 50.0% and 99.9% by volume, preferably between 80.0% and 99.5% by volume, and more preferably between 92.0% and 99.5% by volume for fluorescent emitting layers and between 85.0% and 97.0% by volume for phosphorescent emitting layers.

Correspondingly, the proportion of the emitting compound is between 0.1% and 50.0% by volume, preferably between 0.5% and 20.0% by volume, and more preferably between 0.5% and 8.0% by volume for fluorescent emitting layers and between 3.0% and 15.0% by volume for phosphorescent emitting layers.

An emitting layer of an organic electroluminescent device may also comprise systems comprising a plurality of matrix materials (mixed matrix systems) and/or a plurality of emitting compounds. In this case too, the emitting compounds are generally those compounds having the smaller proportion in the system and the matrix materials are those compounds having the greater proportion in the system. In individual cases, however, the proportion of a single matrix material in the system may be less than the proportion of a single emitting compound.

It is preferable that the compounds of formula (I) are used as a component of mixed matrix systems. The mixed matrix systems preferably comprise two or three different matrix materials, more preferably two different matrix materials. Preferably, in this case, one of the two materials is a material having hole-transporting properties and the other material is a material having electron-transporting properties. The compound of the formula (I) is preferably the matrix material having hole-transporting properties. The desired electron-transporting and hole-transporting properties of the mixed matrix components may, however, also be combined mainly or entirely in a single mixed matrix component, in which case the further mixed matrix component(s) fulfil(s) other functions. The two different matrix materials may be present in a ratio of 1:50 to 1:1, preferably 1:20 to 1:1, more preferably 1:10 to 1:1 and most preferably 1:4 to 1:1. Preference is given to using mixed matrix systems in phosphorescent organic electroluminescent devices. One source of more detailed information about mixed matrix systems is the application WO 2010/108579.

The mixed matrix systems may comprise one or more emitting compounds, preferably one or more phosphorescent emitting compounds. In general, mixed matrix systems are preferably used in phosphorescent organic electroluminescent devices.

Particularly suitable matrix materials which can be used in combination with the inventive compounds as matrix components of a mixed matrix system are selected from the preferred matrix materials specified below for phosphorescent emitting compounds or the preferred matrix materials for fluorescent emitting compounds, according to what type of emitting compound is used in the mixed matrix system.

Preferred phosphorescent emitting compounds for use in mixed matrix systems are the same as detailed further up as generally preferred phosphorescent emitter materials.

Preferred embodiments of the different functional materials in the electronic device are listed hereinafter.

Preferred phosphorescent emitting compounds are those mentioned above.

Preferred fluorescent emitting compounds are selected from the class of the arylamines. An arylamine or an aromatic amine in the context of this invention is understood to mean a compound containing three substituted or unsubstituted aromatic or heteroaromatic ring systems bonded directly to the nitrogen. Preferably, at least one of these aromatic or heteroaromatic ring systems is a fused ring system, more preferably having at least 14 aromatic ring atoms. Preferred examples of these are aromatic anthraceneamines, aromatic anthracenediamines, aromatic pyreneamines, aromatic pyrenediamines, aromatic chryseneamines or aromatic chrysenediamines. An aromatic anthraceneamine is understood to mean a compound in which a diarylamino group is bonded directly to an anthracene group, preferably in the 9 position. An aromatic anthracenediamine is understood to mean a compound in which two diarylamino groups are bonded directly to an anthracene group, preferably in the 9,10 positions. Aromatic pyreneamines, pyrenediamines, chryseneamines and chrysenediamines are defined analogously, where the diarylamino groups in the pyrene are bonded preferably in the 1 position or 1,6 positions. Further preferred emitting compounds are indenofluoreneamines or -diamines, for example according to WO 2006/108497 or WO 2006/122630, benzoindenofluoreneamines or -diamines, for example according to WO 2008/006449, and dibenzoindenofluoreneamines or -diamines, for example according to WO 2007/140847, and the indenofluorene derivatives having fused aryl groups disclosed in WO 2010/012328. Likewise preferred are the pyrenearylamines disclosed in WO 2012/048780 and in WO 2013/185871. Likewise preferred are the benzoindenofluoreneamines disclosed in WO 2014/037077, the benzofluoreneamines disclosed in WO 2014/106522 and the extended benzoindenofluorenes disclosed in WO 2014/111269.

Useful matrix materials, preferably for fluorescent emitting compounds, include materials of various substance classes. Preferred matrix materials are selected from the classes of the oligoarylenes (e.g. 2,2',7,7'-tetraphenylspirobifluorene according to EP 676461 or dinaphthylanthracene), especially of the oligoarylenes containing fused aromatic groups, the oligoarylenevinylenes (e.g. DPVBi or spiro-DPVBi according to EP 676461), the polypodal metal complexes (for example according to WO 2004/081017), the hole-conducting compounds (for example according to WO 2004/058911), the electron-conducting compounds, especially ketones, phosphine oxides, sulphoxides, etc. (for example according to WO 2005/084081 and WO 2005/084082), the atropisomers (for example according to WO 2006/048268), the boronic acid derivatives (for example according to WO 2006/117052) or the benzanthracenes (for example according to WO 2008/145239). Particularly preferred matrix materials are selected from the classes of the oligoarylenes comprising naphthalene, anthracene, benzanthracene and/or pyrene or atropisomers of these compounds, the oligoarylenevinylenes, the ketones, the phosphine oxides and the sulphoxides. Very particularly preferred matrix materials are selected from the classes of the oligoarylenes comprising, anthracene, benzanthracene, benzophenanthrene and/or pyrene or atropisomers of these compounds. An oligoarylene in the context of this invention shall be understood to mean a compound in which at least three aryl or arylene groups are bonded to one another. Preference is further given to the anthracene derivatives disclosed in WO 2006/097208, WO 2006/131192, WO 2007/065550, WO 2007/110129, WO 2007/065678, WO 2008/145239, WO 2009/100925, WO 2011/054442 and EP 1553154, and the pyrene compounds disclosed in EP 1749809, EP 1905754 and US 2012/0187826.

Preferred matrix materials for phosphorescent emitting compounds are, as well as the compounds of the formula (I), aromatic ketones, aromatic phosphine oxides or aromatic sulphoxides or sulphones, for example according to WO 2004/013080, WO 2004/093207, WO 2006/005627 or WO 2010/006680, triarylamines, carbazole derivatives, e.g. CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example according to WO 2007/063754 or WO 2008/056746, indenocarbazole derivatives, for example according to WO 2010/136109, WO 2011/000455 or WO 2013/041176, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2010/015306, WO 2007/063754 or WO 2008/056746, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to US 2009/0136779, WO 2010/050778, WO 2011/042107, WO 2011/088877 or WO 2012/143080, triphenylene derivatives, for example according to WO 2012/048781, or lactams, for example according to WO 2011/116865 or WO 2011/137951.

Suitable charge transport materials as usable in the hole injection or hole transport layer or electron blocker layer or in the electron transport layer of the electronic device of the invention are, as well as the compounds of the formula (I), for example, the compounds disclosed in Y. Shirota et al., Chem. Rev. 2007, 107(4), 953-1010, or other materials as used in these layers according to the prior art.

Preferably, the inventive OLED comprises two or more different hole-transporting layers. The compound of the formula (I) may be used here in one or more of or in all the hole-transporting layers. According to a preferred embodiment, the compound of the formula (I) is used in exactly one hole-transporting layer, and other compounds, preferably aromatic amine compounds, are used in the further hole-transporting layers present.

Materials used for the electron transport layer may be any materials as used according to the prior art as electron transport materials in the electron transport layer. Especially suitable are aluminium complexes, for example Alq$_3$, zirconium complexes, for example Zrq$_4$, lithium complexes, for example Liq, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives. Further suitable materials are derivatives of the above-mentioned compounds as disclosed in JP 2000/053957, WO 2003/060956, WO 2004/028217, WO 2004/080975 and WO 2010/072300.

Preferred cathodes of the electronic device are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag or Al, in which case combinations of the metals such as Ca/Ag, Mg/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, Li$_2$O, BaF$_2$, MgO, NaF, CsF, Cs$_2$CO$_3$, etc.). It is also possible to use lithium quinolinate (LiQ) for this purpose. The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/NiO$_x$, Al/PtO$_x$) may also be preferred. For some applications, at least one of the electrodes has to be transparent or partly transparent in order to enable the irradiation of the organic material (organic solar cell) or the emission of light (OLED, O-LASER). Preferred anode materials here are conductive mixed metal oxides. Particular preference is given to indium tin oxide (ITO) or indium zinc oxide (IZO). Preference is further given to conductive doped organic materials, especially conductive doped polymers. In addition, the anode may also consist of two or more layers, for example of an inner layer of ITO and an outer layer of a metal oxide, preferably tungsten oxide, molybdenum oxide or vanadium oxide.

The device is structured appropriately (according to the application), contact-connected and finally sealed, in order to rule out damaging effects by water and air.

In a preferred embodiment, the electronic device is characterized in that one or more layers are coated by a sublimation process. In this case, the materials are applied by vapour deposition in vacuum sublimation systems at an initial pressure of less than $10^{-5}$ mbar, preferably less than $10^{-6}$ mbar. In this case, however, it is also possible that the initial pressure is even lower, for example less than $10^{-7}$ mbar.

Preference is likewise given to an electronic device, characterized in that one or more layers are coated by the OVPD (organic vapour phase deposition) method or with the aid of a carrier gas sublimation. In this case, the materials are applied at a pressure between $10^{-5}$ mbar and 1 bar. A special case of this method is the OVJP (organic vapour jet printing) method, in which the materials are applied directly by a nozzle and thus structured (for example M. S. Arnold et al., Appl. Phys. Lett. 2008, 92, 053301).

Preference is additionally given to an electronic device, characterized in that one or more layers are produced from solution, for example by spin-coating, or by any printing method, for example screen printing, flexographic printing, nozzle printing or offset printing, but more preferably LITI (light-induced thermal imaging, thermal transfer printing) or inkjet printing. For this purpose, soluble compounds of formula (I) are needed. High solubility can be achieved by suitable substitution of the compounds.

It is further preferable that an electronic device of the invention is produced by applying one or more layers from solution and one or more layers by a sublimation method.

According to the invention, the electronic devices comprising one or more compounds of formula (I) can be used in displays, as light sources in lighting applications and as light sources in medical and/or cosmetic applications (e.g. light therapy).

WORKING EXAMPLES

A) Synthesis Examples

Example 1: Synthesis of Compounds (I-1) to (I-26)

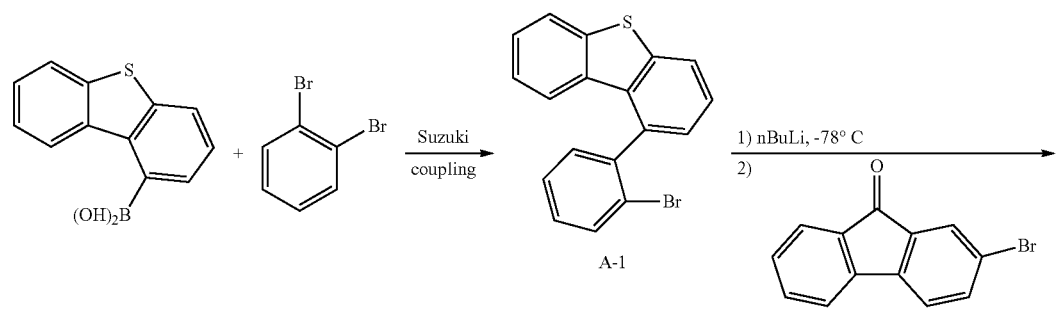

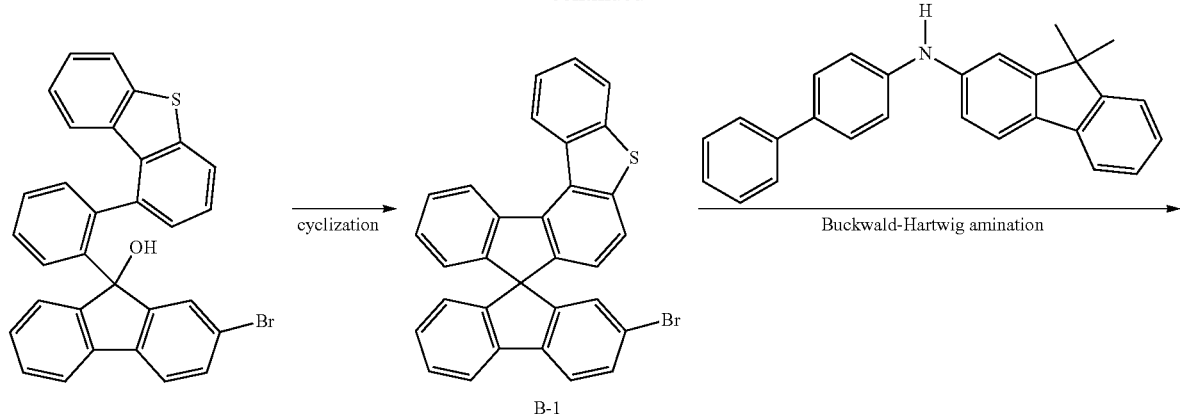

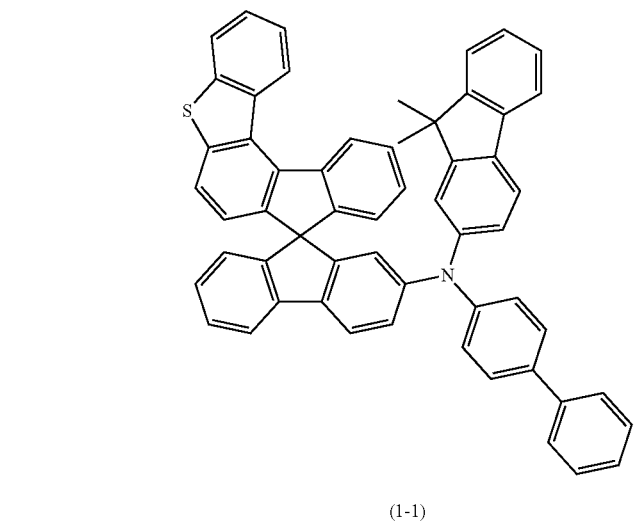

(1-1)

Synthesis of 1-(2-bromophenyl)dibenzothiophene A-1

80 g (351 mmol) of dibenzothiophene-1-boronic acid (CAS: 1245943-60-5), 83 g (351 mmol) of 1,2-dibromobenzene and 8.2 g (7.02 mmol) of Pd(Ph₃P)₄ are suspended in 700 ml of dioxane. Added gradually to this suspension are 440 ml (877 mmol) of 2 M potassium carbonate solution, and the reaction mixture is heated under reflux for 18 h. After cooling, the organic phase is removed, filtered through silica gel, washed three times with 200 ml of water and then concentrated to dryness. The residue is purified by chromatography on silica gel. Yield: 101 g (297 mmol), 85% of theory, purity by HPLC>97%.

In a manner analogous to the synthesis of compound A-1 described, the following compounds are prepared:

| | Reactant 1 | Reactant 2 | Product | Yield |
|---|---|---|---|---|
| A-2 | ![dibenzothiophene boronic acid] HO—B(OH)₂ 1245943-60-5 | Br-phenyl-Cl (I) | dibenzothiophene-phenyl Br/Cl | 70% |

| | Reactant 1 | Reactant 2 | Product | Yield |
|---|---|---|---|---|
| A-3 | 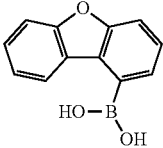 [SMILES: OB(O)c1cccc2oc3ccccc3c12]<br>162607-19-4 |  | 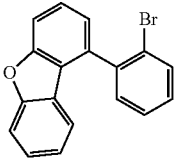 [SMILES: Brc1ccccc1-c1cccc2oc3ccccc3c12] | 75% |
| A-4 | 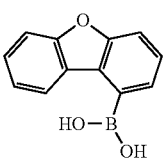 [SMILES: OB(O)c1cccc2oc3ccccc3c12]<br>162607-19-4 | 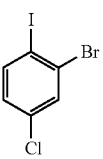 | 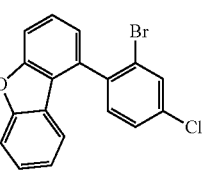 | 60% |
| A-5 | 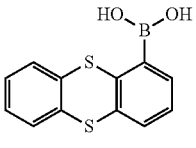<br>108847-76-3 |  | 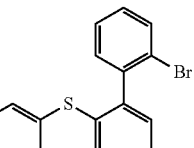 | 55% |
| A-6 | 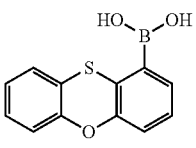 [SMILES: OB(O)c1cccc2c1Sc1ccccc1O2]<br>636607-99-3 |  | 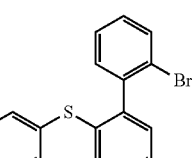 | 67% |
| A-13 | 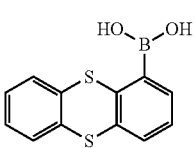 [SMILES: OB(O)c1cccc2c1Sc1ccccc1S2]<br>108847-76-3 | 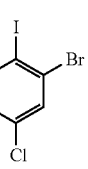 | 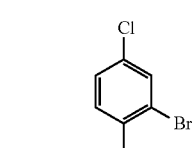 | 73% |
| A-14 | 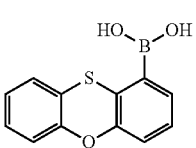 [SMILES: OB(O)c1cccc2c1Sc1ccccc1O2]<br>636607-99-3 | 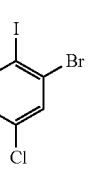 | 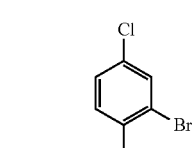 | 81% |

Synthesis of Intermediate B-1

56.3 g (166 mmol) of 1-(2-bromophenyl)dibenzothiophene A-1 are initially charged in 700 ml of THF at −78° C. At this temperature, 70 ml of BuLi (2.5 M in hexane) are added dropwise. After 1 hour, 45.2 g (174 mmol) of 2-bromofluoren-9-one in 200 ml of THF are added dropwise. The mixture is left to stir at room temperature overnight, added to ice-water and extracted with dichloromethane. The combined organic phases are washed with water and dried over sodium sulphate. The solvent is removed under reduced pressure and the residue, without further purification, is heated with 90 ml of HCl and 1 l of AcOH at 75° C. overnight. After cooling, the precipitated solid is filtered off with suction and washed twice with 150 ml of water and three times with 150 ml each time of ethanol, and finally recrystallized from heptane. Yield: 59 g (117 mmol), 71%; purity about 98% by $^1$H NMR.

In a manner analogous to the synthesis of compound B-1 described, the following compounds are prepared:

| Reactant 1 | Reactant 2 | Product | Yield |
|---|---|---|---|
| B-2 | 4269-17-4 | | 62% |
| B-3 | 486-25-9 | | 70% |
| B-4 | 3096-56-8 | | 70% |
| B-5 | 3096-49-9 | | 81% |
| B-6 | 154851-21-3 | | 75% |

-continued

| | Reactant 1 | Reactant 2 | Product | Yield |
|---|---|---|---|---|
| B-7 | | 115033-91-5 | | 60% |
| B-8 | | 58775-13-6 | | 68% |
| B-9 | | 58775-11-4 | | 75% |
| B-10 | | 14348-75-5 | | 62% |
| B-11 | | 24313-53-9 | | 62% |

| | Reactant 1 | Reactant 2 | Product | Yield |
|---|---|---|---|---|
| B-11 | 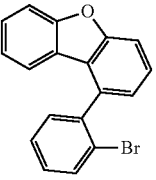 [SMILES: Brc1ccccc1-c1cccc2oc3ccccc3c12] | 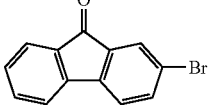 3096-56-8 | 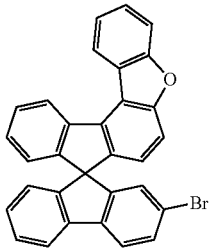 [SMILES: Brc1ccc2c(c1)C1(c3ccccc3-2)c2ccccc2-c2c1ccc1oc3ccccc3c21] | 70% |
| B-12 | 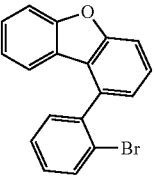 [SMILES: Brc1ccccc1-c1cccc2oc3ccccc3c12] | 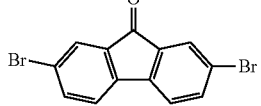 14348-75-5 | 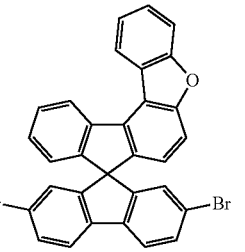 | 65% |
| B-13 | 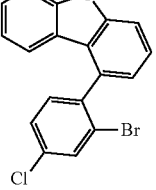 | 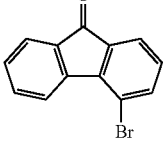 4269-17-4 | 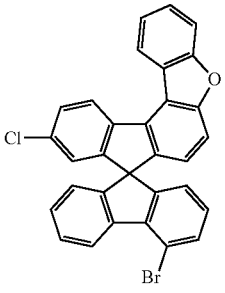 [SMILES: Clc1ccc2c(c1)C1(c3ccccc3-c3c(Br)cccc31)c1ccc3oc4ccccc4c3c1-2] | 75% |
| B-14 | 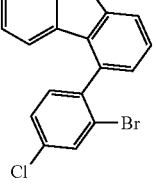 | 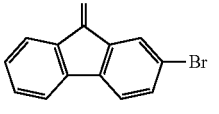 3096-56-8 | 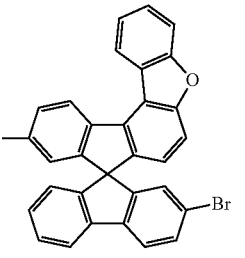 | 68% |
| B-17 | 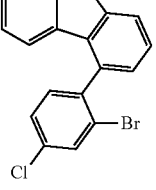 | 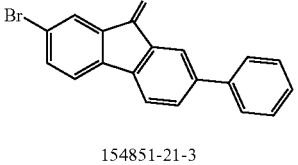 154851-21-3 | 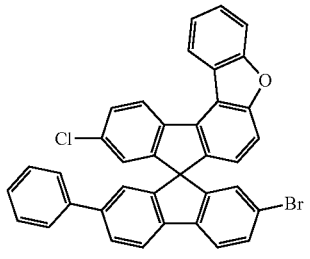 [SMILES: Clc1ccc2c(c1)C1(c3cc(Br)ccc3-c3ccc(-c4ccccc4)cc31)c1ccc3oc4ccccc4c3c1-2] | 67% |
| B-18 | 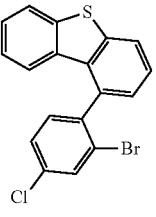 [SMILES: Clc1ccc(-c2cccc3sc4ccccc4c23)c(Br)c1] | 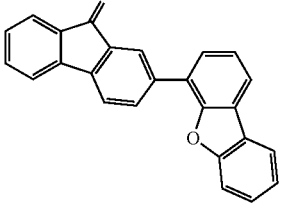 | 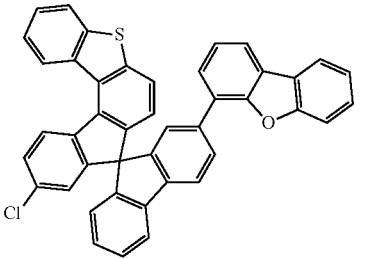 [SMILES: Clc1ccc2c(c1)C1(c3ccccc3-c3ccc(-c4cccc5c4oc4ccccc45)cc31)c1ccc3sc4ccccc4c3c1-2] | 74% |

| | Reactant 1 | Reactant 2 | Product | Yield |
|---|---|---|---|---|
| B-19 | | 3096-56-8 | | 65% |
| B-20 | | 486-25-9 | | 72% |
| B-21 | | 486-25-9 | | 68% |

Synthesis of Compound (1-1)

13.7 g (38 mmol) of biphenyl-4-yl(9,9-dimethyl-9H-fluoren-2-yl)amine and 17.4 g (38 mol) of the bromo-spiro derivative B-1 are dissolved in 300 ml of toluene. The solution is degassed and saturated with $N_2$. Thereafter, 1.52 ml (1.52 mmol) of a 1 M tri-tert-butylphosphine solution and 170 mg (0.76 mmol) of Pd(AcO)$_2$ are added thereto, and then 9.0 g of sodium tert-butoxide (94.2 mmol) are added. The reaction mixture is heated to boiling under a protective atmosphere for 5 h. The mixture is subsequently partitioned between toluene and water, and the organic phase is washed three times with water and dried over $Na_2SO_4$ and concentrated by rotary evaporation. After the crude product has been filtered through silica gel with toluene, the remaining residue is recrystallized from heptane/toluene and finally sublimed under high vacuum. The purity is 99.9% (HPLC). The yield of compound (1-1) is 22.7 g (77% of theory).

Synthesis of compounds (I-2) to (I-26)

In a manner analogous to the synthesis of compound (1-1) described in Example 1, the following compounds (1-2) to (1-26) are also prepared:

| | Reactant 1 | Reactant 2 | Product | Yield |
|---|---|---|---|---|
| 1-2 | | | | 75% |
| 1-3 | | | | 75% |

| | Reactant 1 | Reactant 2 | Product | Yield |
|---|---|---|---|---|
| 1-4 | 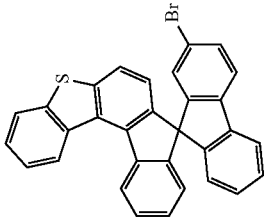 | 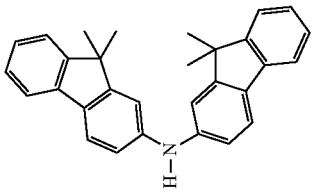 | 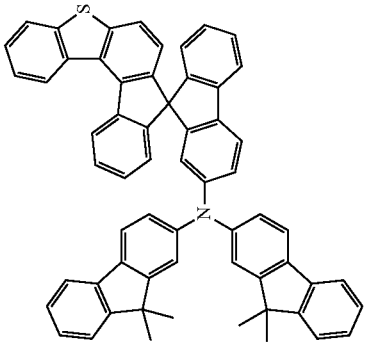 | 73% |
| 1-5 | 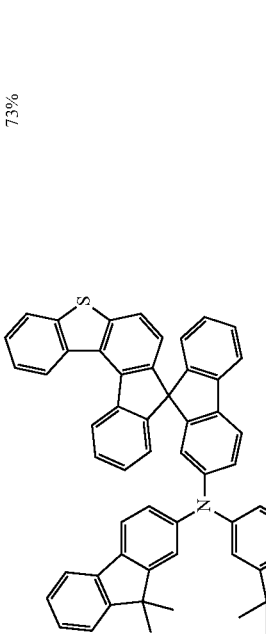 | 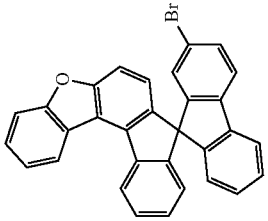 | 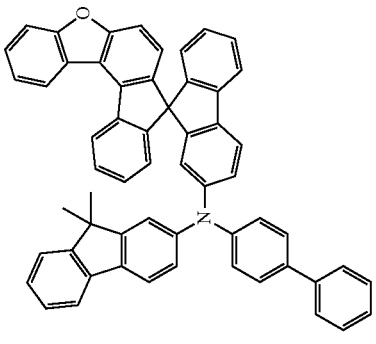 | 78% |

| | Reactant 1 | Reactant 2 | Product | Yield |
|---|---|---|---|---|
| 1-6 | | | | 80% |
| 1-7 | | | | 70% |

-continued

| | Reactant 1 | Reactant 2 | Product | Yield |
|---|---|---|---|---|
| 1-8 | | | | 75% |
| 1-9 | | | | 81% |

| | Reactant 1 | Reactant 2 | Product | Yield |
|---|---|---|---|---|
| 1-10 | | | | 78% |
| 1-11 | | | | 70% |
| 1-12 | | | | 76% |

-continued
| | Reactant 1 | Reactant 2 | Product | Yield |
|---|---|---|---|---|
| 1-13 | 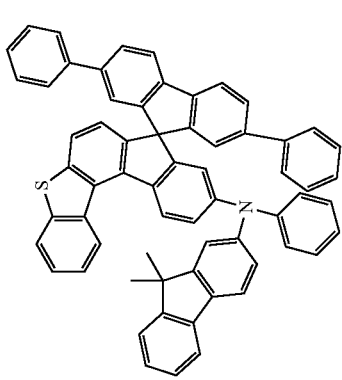 | 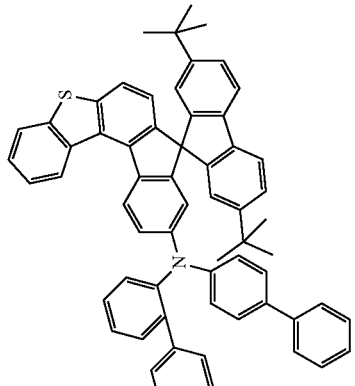 | 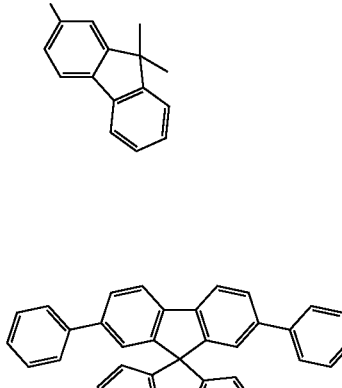 | 70% |
| 1-14 | 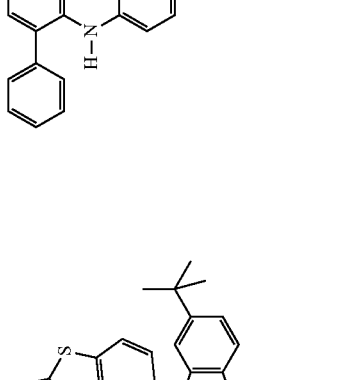 | 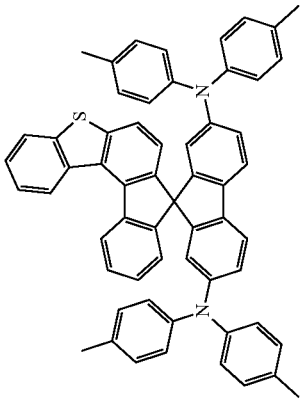 | 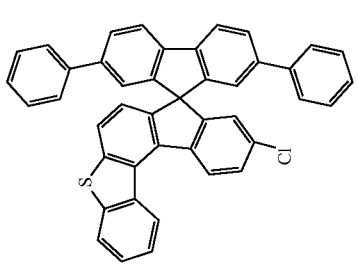 | 65% |
| 1-15 | 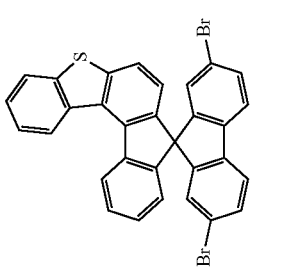 | (2 eq) | | 60% |

| | Reactant 1 | Reactant 2 | Product | Yield |
|---|---|---|---|---|
| 1-16 | | (2 eq) | | 70% |
| 1-17 | | | | 78% |

-continued
| | Reactant 1 | Reactant 2 | Product | Yield |
|---|---|---|---|---|
| 1-18 | 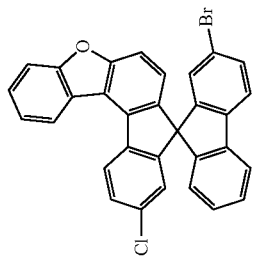 | 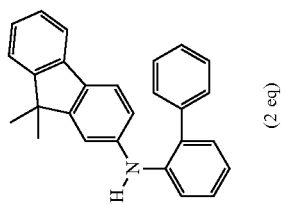 (2 eq) | 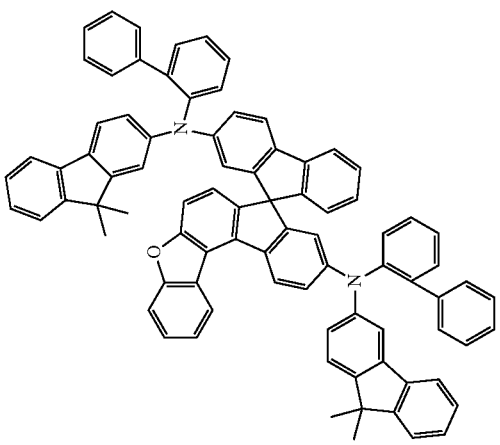 | 80% |
| 1-19 | 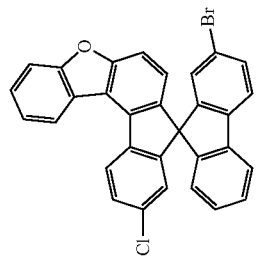 | 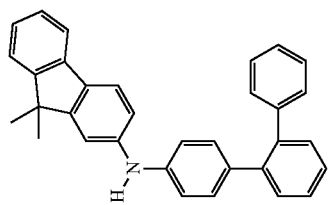 | 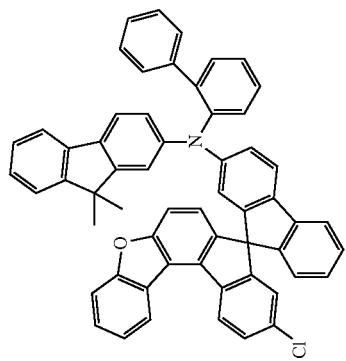 | 67% |

| | Reactant 1 | Reactant 2 | Product | Yield |
|---|---|---|---|---|
| 1-20 | 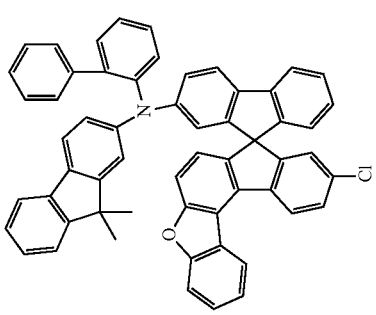 | 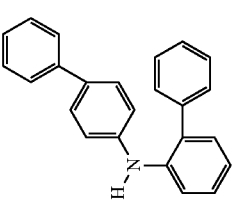 | 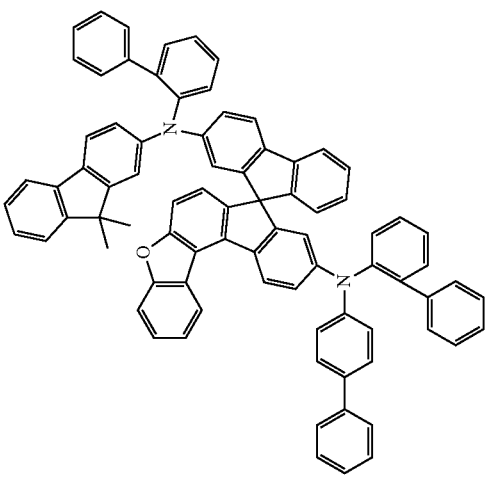 | 75% |
| 1-21 | 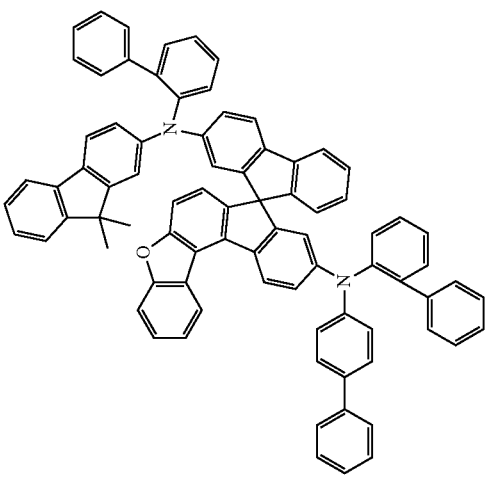 | 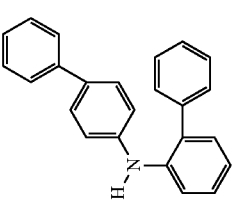 | 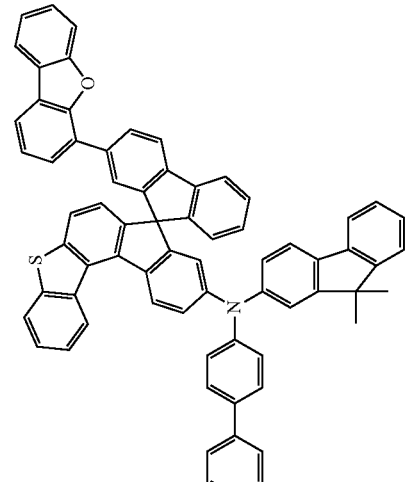 | 80% |

| | Reactant 1 | Reactant 2 | Product | Yield |
|---|---|---|---|---|
| 1-22 | | | | 75% |
| 1-23 | | | | 80% |
| 1-24 | | | | 65% |

-continued

| | Reactant 1 | Reactant 2 | Product | Yield |
|---|---|---|---|---|
| 1-25 | | | | 77% |
| 1-26 | | | | 67% |

Example 2: Synthesis of Compounds 2-1 to 2-9

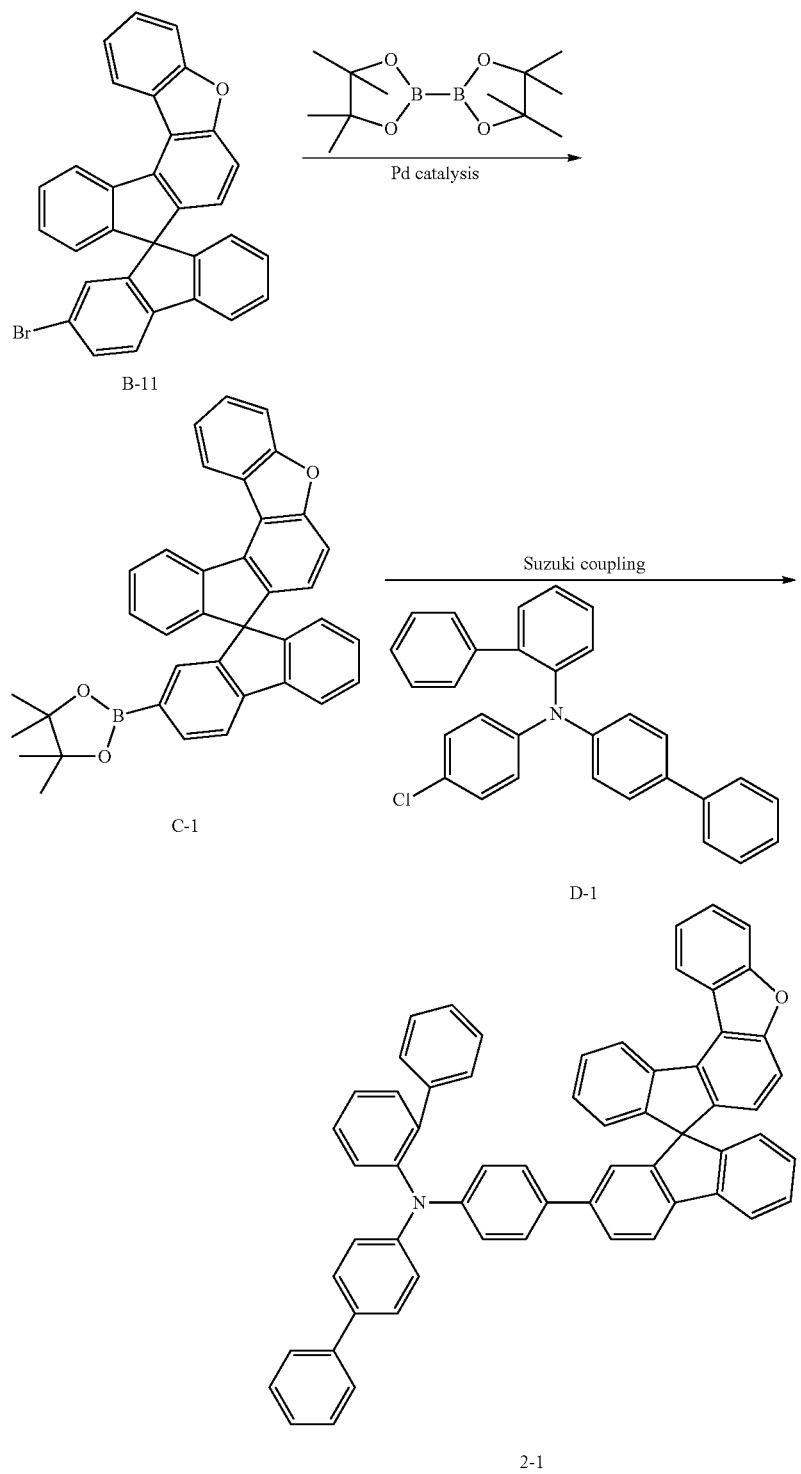

Spirofluorene-Boronic Ester Derivative (C-1)

36 g (74.2 mmol) of the spirofluorene-bromo derivative B11, 22.6 g (89 mmol) of bis(pinacolato)diborane and 21.8 g (222 mmol) of potassium acetate are suspended in 400 ml of DMF. To this suspension is added 1.82 g (2.23 mmol) of 1,1-bis(diphenylphosphino)ferrocenedichloropalladium(II) complex with DCM. The reaction mixture is heated under reflux for 16 h. After cooling, the organic phase is removed, washed three times with 400 ml of water and then concentrated to dryness. The residue is recrystallized from toluene (37 g, 94% yield).

In a manner analogous thereto, the following compounds are prepared:

| | Reactant 1 | Product | Yield |
|---|---|---|---|
| C-2 | | | 62% |
| C-3 | | | 70% |
| C-4 | | | 70% |
| C-5 | | | 81% |
| C-6 | | | 87% |

| Reactant 1 | Product | Yield |
|---|---|---|
| C-7 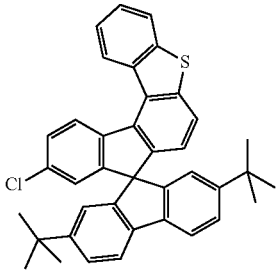 [SMILES: CC(C)(C)c1ccc2c(c1)C1(c3cc(C(C)(C)C)ccc3-2)c2cc(Cl)ccc2-c2c1ccc1sc3ccccc3c21] | 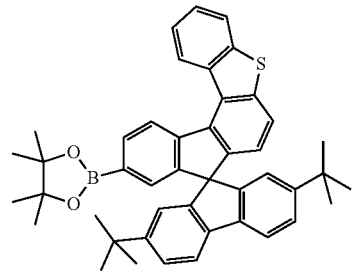 [SMILES: CC(C)(C)c1ccc2c(c1)C1(c3cc(C(C)(C)C)ccc3-2)c2cc(B3OC(C)(C)C(C)(C)O3)ccc2-c2c1ccc1sc3ccccc3c21] | 85% |
| C-10 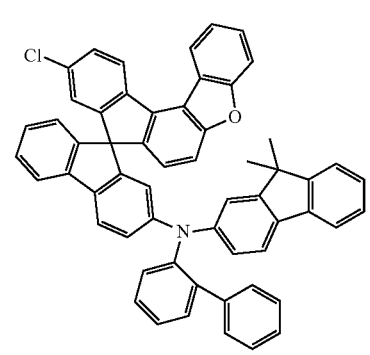 [SMILES: CC1(C)c2ccccc2-c2ccc(N(c3ccc4c(c3)C3(c5ccccc5-4)c4cc(Cl)ccc4-c4c3ccc3oc5ccccc5c43)c3ccccc3-c3ccccc3)cc21] | 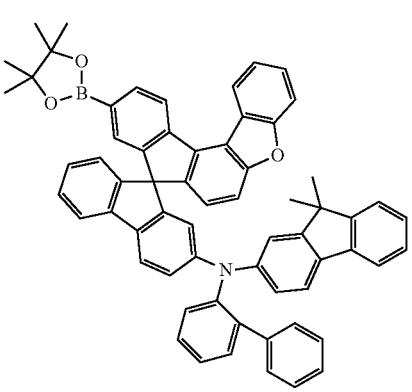 [SMILES: CC1(C)c2ccccc2-c2ccc(N(c3ccc4c(c3)C3(c5ccccc5-4)c4cc(B5OC(C)(C)C(C)(C)O5)ccc4-c4c3ccc3oc5ccccc5c43)c3ccccc3-c3ccccc3)cc21] | 70% |

Biphenyl-2-yl(biphenyl-4-yl)(4-chlorophenyl)amine (D-1)

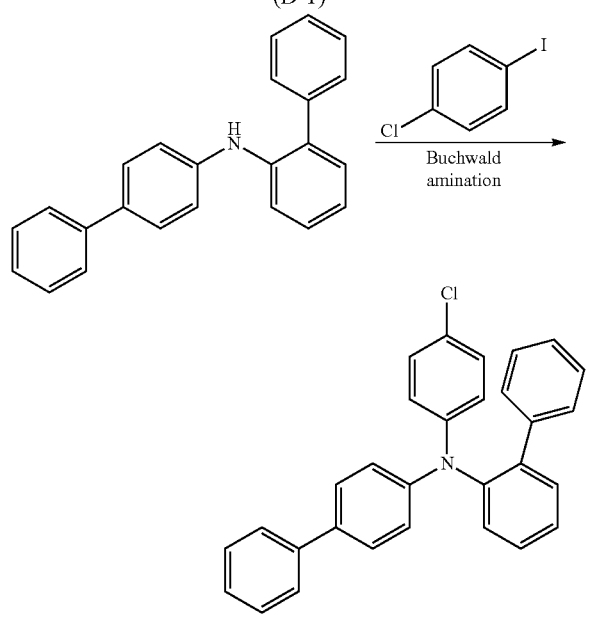

23.8 g of biphenyl-2-yl(biphenyl-4-yl)amine (74 mmol) and 21.2 g of 4-chloroiodobenzene (89 mmol) are dissolved in 500 ml of toluene. The solution is degassed and saturated with $N_2$. Thereafter, 3 ml (3 mmol) of a 1 M tri-tert-butylphosphine solution and 0.33 g (1.48 mmol) of palladium(II) acetate are added thereto, and then 10.7 g of sodium tert-butoxide (111 mmol) are added. The reaction mixture is heated to boiling under a protective atmosphere for 12 h. The mixture is subsequently partitioned between toluene and water, and the organic phase is washed three times with water and dried over $Na_2SO_4$ and concentrated by rotary evaporation. After the crude product has been filtered through silica gel with toluene, the remaining residue is recrystallized from heptane/toluene. The yield is 29 g (90% of theory).

In a manner analogous thereto, the following compounds are prepared:

| | Reactant 1 | Reactant 2 | Product | Yield |
|---|---|---|---|---|
| D-2 | 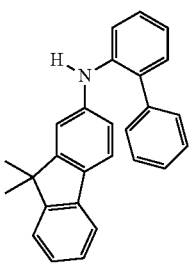 [SMILES: CC1(C)c2ccccc2-c2ccc(Nc3ccccc3-c3ccccc3)cc21] | 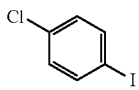 | 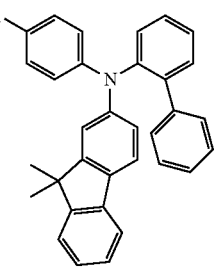 | 78% |
| D-3 | 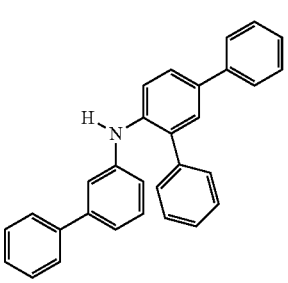 [SMILES: c1ccc(-c2cccc(Nc3ccc(-c4ccccc4)cc3-c3ccccc3)c2)cc1] | 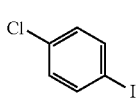 | 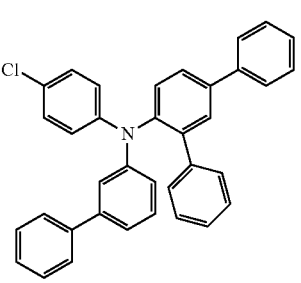 [SMILES: Clc1ccc(N(c2cccc(-c3ccccc3)c2)c2ccc(-c3ccccc3)cc2-c2ccccc2)cc1] | 80% |
| D-4 | 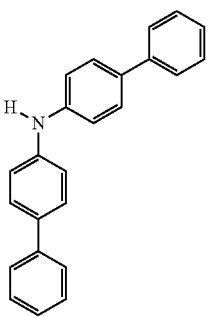 [SMILES: c1ccc(-c2ccc(Nc3ccc(-c4ccccc4)cc3)cc2)cc1] | 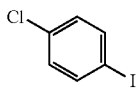 | 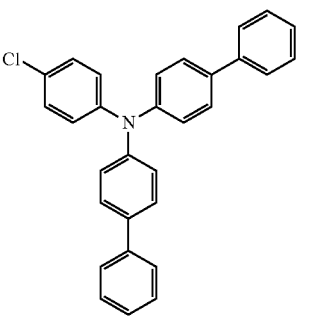 | 81% |
| D-5 | 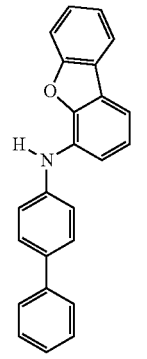 | 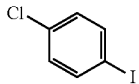 | 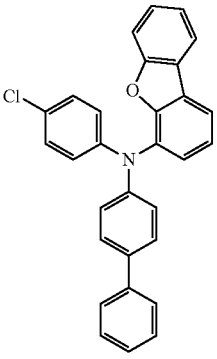 [SMILES: Clc1ccc(N(c2ccc(-c3ccccc3)cc2)c2cccc3c2oc2ccccc23)cc1] | 92% |
| D-6 | 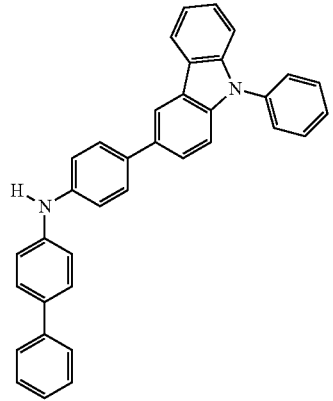 [SMILES: c1ccc(-c2ccc(Nc3ccc(-c4ccc5c(c4)c4ccccc4n5-c4ccccc4)cc3)cc2)cc1] | 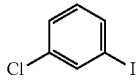 | 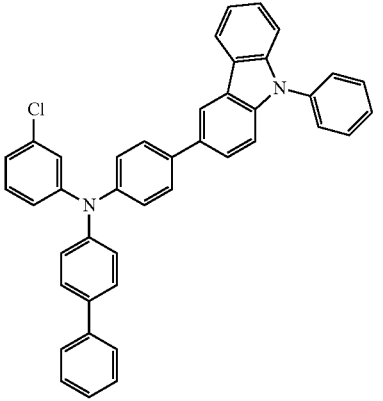 [SMILES: Clc1cccc(N(c2ccc(-c3ccccc3)cc2)c2ccc(-c3ccc4c(c3)c3ccccc3n4-c3ccccc3)cc2)c1] | 85% |

-continued

| | Reactant 1 | Reactant 2 | Product | Yield |
|---|---|---|---|---|
| D-7 | 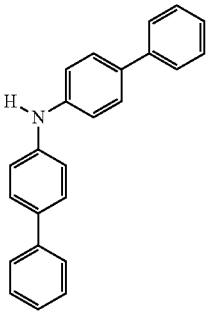 | 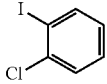 | 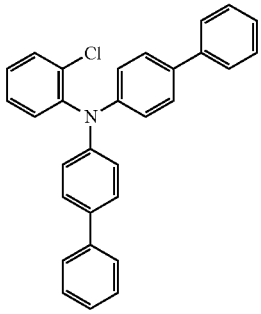 [SMILES: Clc1ccccc1N(c1ccc(-c2ccccc2)cc1)c1ccc(-c2ccccc2)cc1] | 75% |
| C-8 | 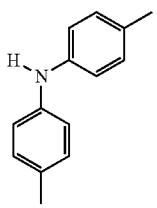 | 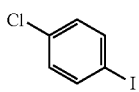 | 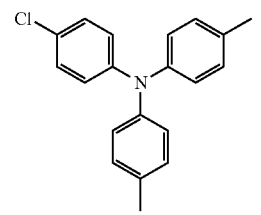 [SMILES: Cc1ccc(N(c2ccc(C)cc2)c2ccc(Cl)cc2)cc1] | 89% |

Synthesis of Compound (2-1)

18.0 g (32 mmol) of spirofluorene pinacolboronic ester derivative C-1 and 15.3 g (32 mmol) of chloro derivative D-1 are suspended in 360 ml of dioxane and 9.8 g of caesium fluoride (64 mmol). 1.19 g (1.6 mmol) of bis(tricyclohexylphosphine)palladium dichloride are added to this suspension, and the reaction mixture is heated under reflux for 16 h. After cooling, the organic phase is removed, filtered through silica gel, washed three times with 100 ml of water and then concentrated to dryness. After the crude product has been filtered through silica gel with toluene, the remaining residue is recrystallized from heptane/toluene and finally sublimed under high vacuum. The purity is 99.9%. The yield is 18 g (70% of theory).

Synthesis of Compounds (2-2) to (2-9)

In a manner analogous to the synthesis of compound (2-1) described, the following compounds (2-2) to (2-9) are also prepared:

| | Reactant 1 | Reactant 2 | Product | Yield |
|---|---|---|---|---|
| 2-2 | 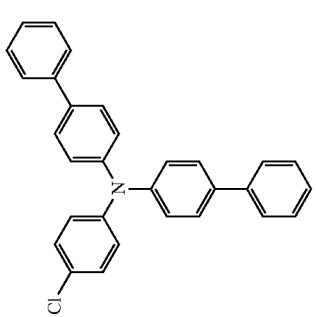 | 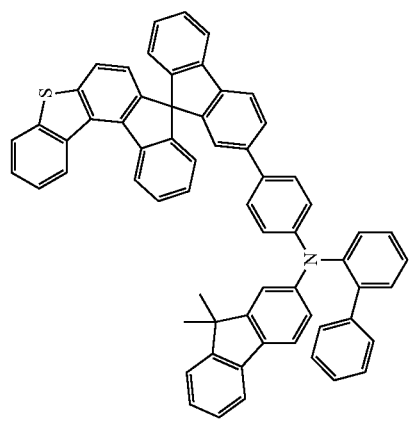 | 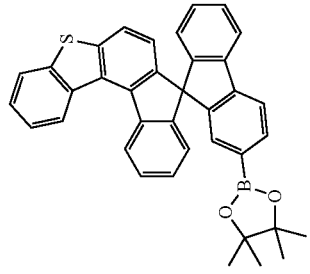 | 72% |
| 2-3 | 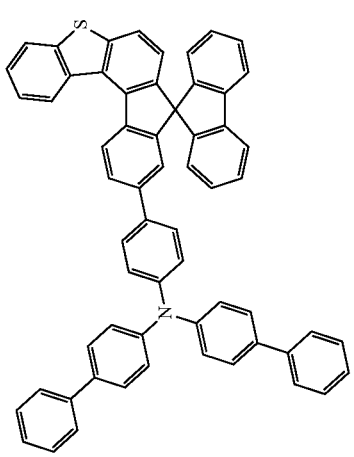 | 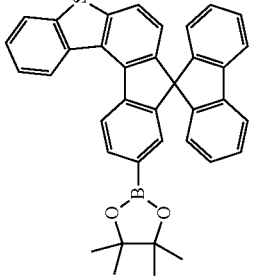 | 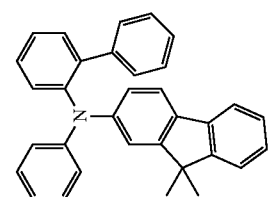 | 71% |

US 10,032,989 B2
-continued
| | Reactant 1 | Reactant 2 | Product | Yield |
|---|---|---|---|---|
| 2-4 | 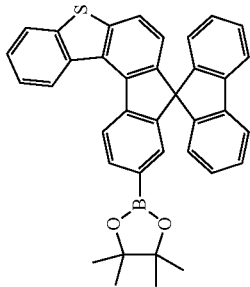 | 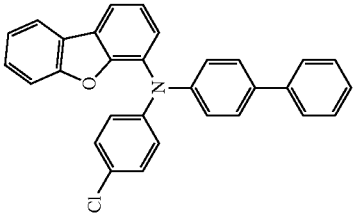 | 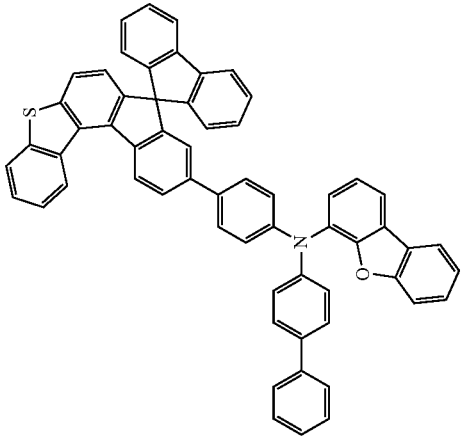 | 82% |
| 2-5 | 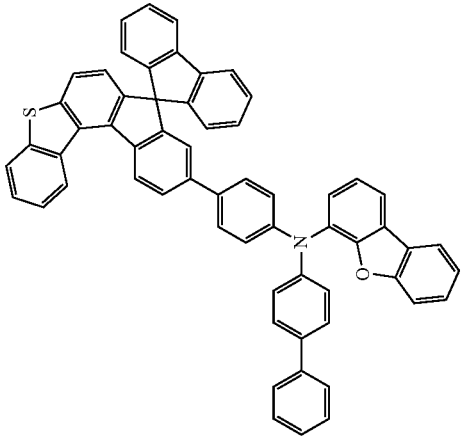 | 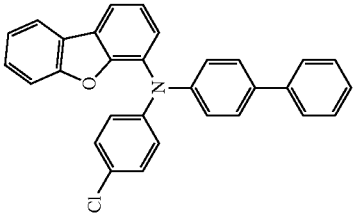 | 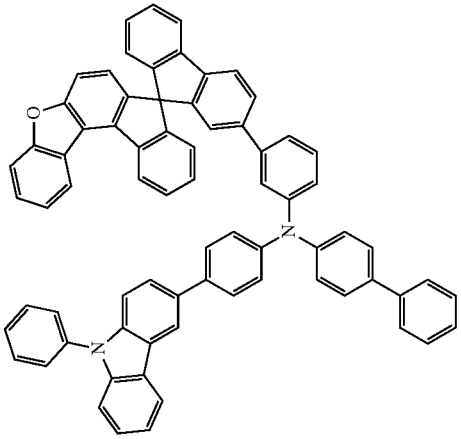 | 89% |

| | Reactant 1 | Reactant 2 | Product | Yield |
|---|---|---|---|---|
| 2-6 | (structure) | (structure) | (structure) | 69% |

-continued

| | Reactant 1 | Reactant 2 | Product | Yield |
|---|---|---|---|---|
| 2-7 | | | | 55% |
| 2-8 | | | | 72% |

-continued

| | Reactant 1 | Reactant 2 | Product | Yield |
|---|---|---|---|---|
| 2-9 | | | | 76% |

Example 3: Synthesis of Compounds 3-1 to 3-4

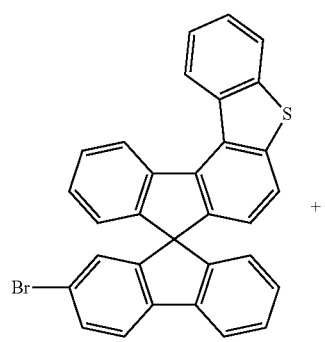

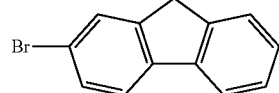

+

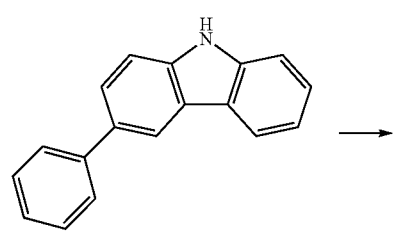

→

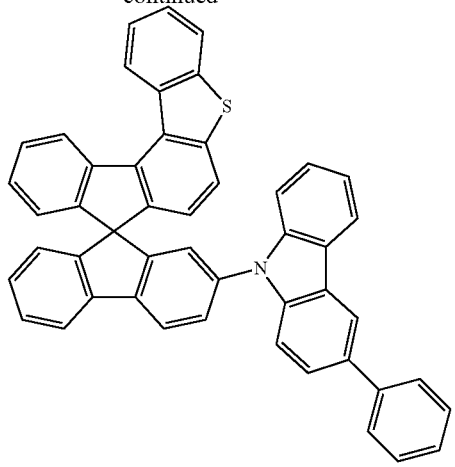

3-1

12.2 g (50 mmol) of 3-phenylcarbazole and 21 g (42 mmol) of the bromo-spiro derivative are dissolved in 300 ml of toluene. The solution is degassed and saturated with $N_2$. Thereafter, 1.68 ml (1.68 mmol) of a 1 M tri-tert-butylphosphine solution and 770 mg (0.84 mmol) of $Pd_2(dba)_3$ are added thereto, and then 6.18 g of sodium tert-butoxide (63 mmol) are added. The reaction mixture is heated to boiling under a protective atmosphere for 26 h. The mixture is subsequently partitioned between toluene and water, and the organic phase is washed three times with water and dried over $Na_2SO_4$ and concentrated by rotary evaporation. After the crude product has been filtered through silica gel with toluene, the remaining residue is recrystallized from heptane/toluene and finally sublimed under high vacuum. The purity is 99.9% (HPLC). The yield of compound (3-1) is 13.5 g (58% of theory).

Synthesis of Compounds (3-2) to (3-4)

In a manner analogous to the synthesis of compound (3-1) described in Example 1, the following compounds (3-2) to (3-4) are also prepared:

| | Reactant 1 | Reactant 2 | Product | Yield |
|---|---|---|---|---|
| 3-2 | | | | 38% |

1257220-47-5

| Reactant 1 | Reactant 2 | Product | Yield |
|---|---|---|---|
| 3-3 | 1427738-11-1 | | 45% |
| 3-4 | | | 43% |

B) Device Examples

OLEDs of the invention and OLEDs according to the prior art are produced by a general method according to WO 04/058911, which is adapted to the circumstances described here (e.g. materials).

In the inventive examples which follow, the data for various OLEDs are presented. Substrates used are glass plates coated with structured ITO (indium tin oxide) of thickness 50 nm. The OLEDs have the following general layer structure: substrate/p-doped hole transport layer (HIL)/hole transport layer (HTL)/electron blocker layer (EBL)/emission layer (EML)/electron transport layer (ETL)/electron injection layer (EIL) and finally a cathode. The cathode is formed by an aluminium layer of thickness 100 nm. The materials required for production of the OLEDs are shown in Table 1.

All materials are applied by thermal vapour deposition in a vacuum chamber. In this case, the emission layer always consists of at least one matrix material (host material) and an emitting dopant (emitter) which is added to the matrix material(s) in a particular proportion by volume by co-evaporation. Details given in such a form as H1:SEB(5%) mean here that the material H1 is present in the layer in a proportion by volume of 95% and SEB in a proportion by volume of 5%. In an analogous manner, the electron transport layers or the hole injection layers may also consist of a mixture of two or more materials. The number in brackets after the materials indicates the particular layer thickness in which the aformentioned materials are present.

The OLEDs are characterized in a standard manner. For this purpose, the external quantum efficiency (EQE, measured in percent) is determined as a function of luminance, calculated from current-voltage-luminance characteristics (IUL characteristics) assuming Lambertian radiation characteristics, and the lifetime. The parameter EQE @ 10 mA/cm$^2$ refers to the external quantum efficiency at a current density of 10 mA/cm$^2$. LD80 @ 60 mA/cm$^2$ is the lifetime before the OLED, given a starting brightness at constant current of 60 mA/cm$^2$, has fallen to 80% of the starting intensity.

TABLE 1

Structures of the materials used

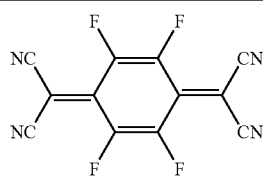

F4TCNQ

TABLE 1-continued
Structures of the materials used
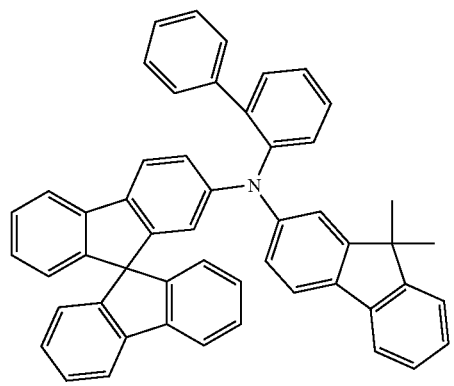 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
HIM
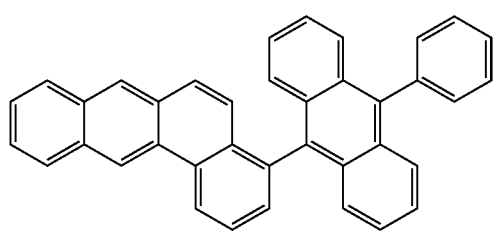 [SMILES: c1ccc(-c2c3ccccc3c(-c3cccc4c3ccc3cc5ccccc5cc34)c3ccccc23)cc1]
H1
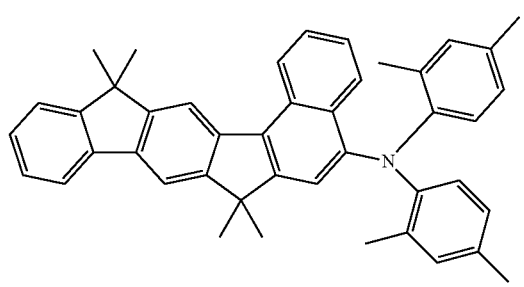 [SMILES: Cc1ccc(N(c2ccc(C)cc2C)c2cc3c(c4ccccc24)-c2cc4c(cc2C3(C)C)-c2ccccc2C4(C)C)c(C)c1]
SEB
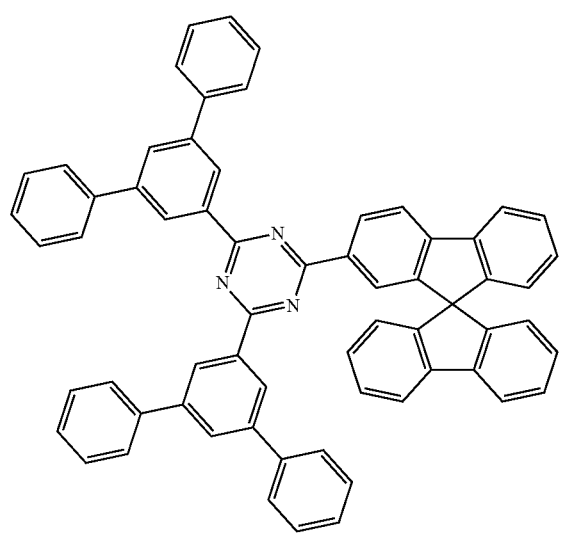 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ETM
TABLE 1-continued
Structures of the materials used
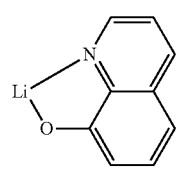
LiQ
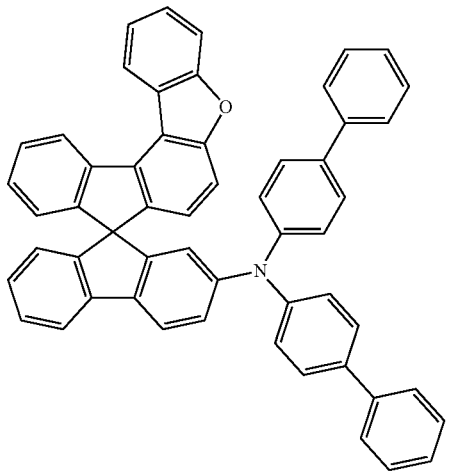 [SMILES: c1ccc(-c2ccc(N(c3ccc(-c4ccccc4)cc3)c3ccc4c(c3)C3(c5ccccc5-4)c4ccccc4-c4c3ccc3oc5ccccc5c43)cc2)cc1]
HTM1
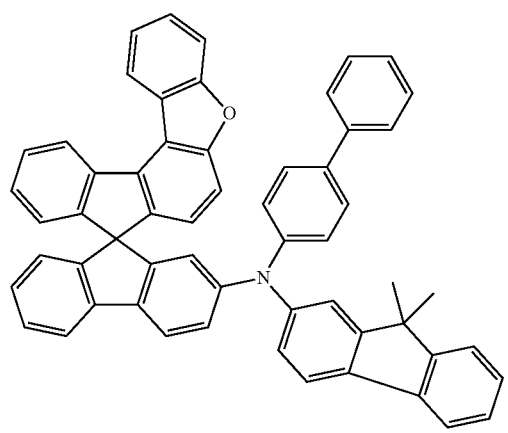 [SMILES: CC1(C)c2ccccc2-c2ccc(N(c3ccc(-c4ccccc4)cc3)c3ccc4c(c3)C3(c5ccccc5-4)c4ccccc4-c4c3ccc3oc5ccccc5c43)cc21]
HTM2

TABLE 1-continued
Structures of the materials used
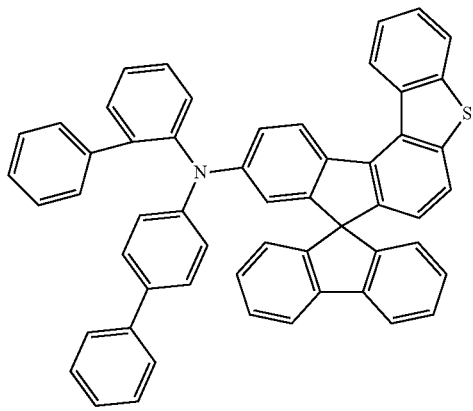 [SMILES: c1ccc(-c2ccc(N(c3ccc4c(c3)C3(c5ccccc5-c5ccccc53)c3ccc5sc6ccccc6c5c3-4)c3ccccc3-c3ccccc3)cc2)cc1]
HTM3
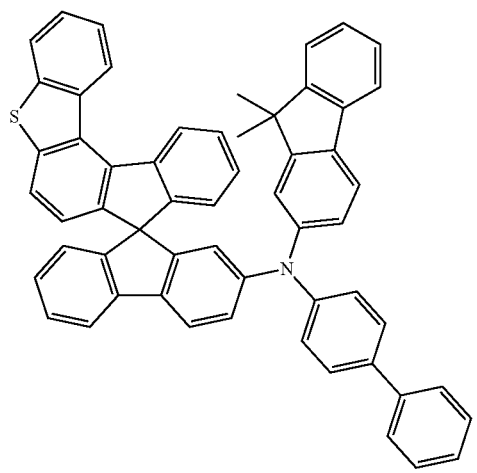 [SMILES: CC1(C)c2ccccc2-c2ccc(N(c3ccc(-c4ccccc4)cc3)c3ccc4c(c3)C3(c5ccccc5-4)c4ccccc4-c4c3ccc3sc5ccccc5c43)cc21]
HTM4
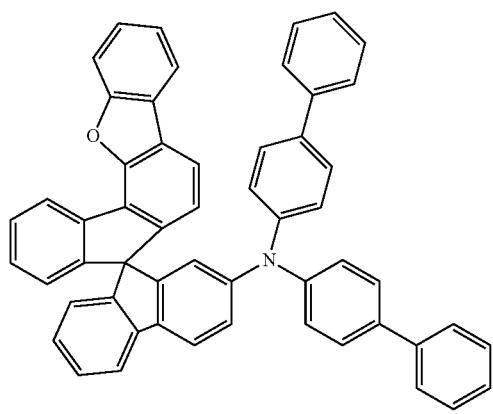 [SMILES: c1ccc(-c2ccc(N(c3ccc(-c4ccccc4)cc3)c3ccc4c(c3)C3(c5ccccc5-4)c4ccccc4-c4c3ccc3c4oc4ccccc43)cc2)cc1]
HTMv1
TABLE 1-continued
Structures of the materials used
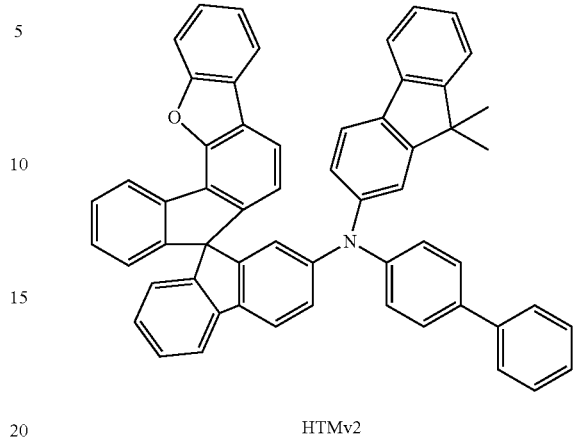
HTMv2
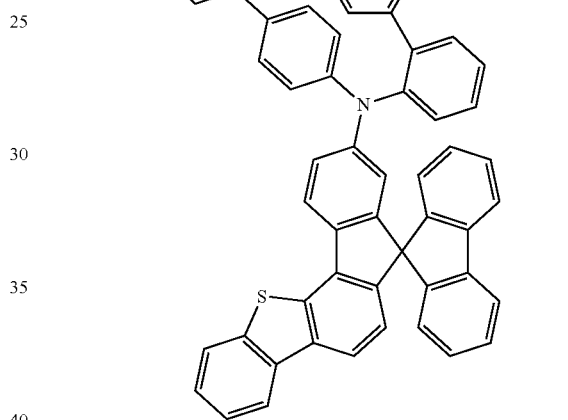
HTMv3
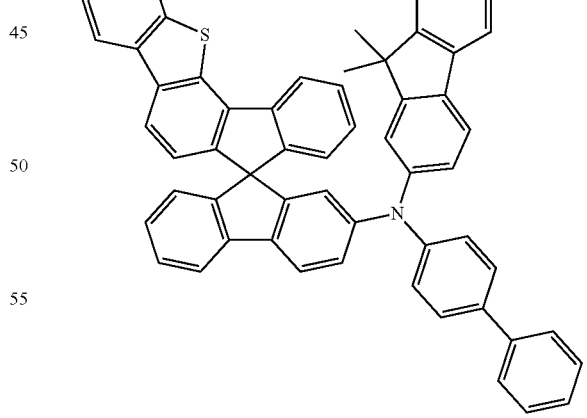
HTMv4
Example 1
The inventive compound HTM1 and the comparative compound HTMv1 are compared with one another in a blue stack. The structure of the stack is as follows: HIM:F4TCNQ(5%)(20 nm)/HIM(175 nm)/HTM1(20 nm)/H1:SEB(5%)(20 nm)/ETM:LiQ(50%)(30 nm)/LiQ(1 nm). In the comparative example, rather than HTM1, HTMv1 is evaporated in the layer in question. The evaluation of the external quantum efficiencies at 10 mA/cm² for the experiments conducted shows the following results: HTM1 achieves 8.1% EQE, whereas HTMv1 reaches only 6.6%. The operating voltage of the OLED comprising inventive material at 3.86 V is also well above the voltage across the diode in the case of the comparative material at 10 mA/cm². This is 4.08 V in the comparative case and is accordingly 6% higher.

Example 2

A further inventive material HTM2 is compared with the direct analogue HTMv2 having a twisted dibenzofuran unit. This OLED component has the following architecture: HIM:F4TCNQ(5%)(20 nm)/HIM(175 nm)/HTM2(20 nm) bzw. HTMv2 (20 nm)/H1:SEB(5%)(20 nm)/ETM:LiQ(50%)(30 nm)/LiQ(1 nm). Here too, the advantage of the inventive compound is apparent. The external quantum efficiency in the case of the sample comprising HTM2 is 7.5%, whereas the comparative sample only manages 7.2% EQE at a current density of 10 mA/cm².

Example 3

A further component having the layer structure HIM:F4TCNQ(5%)(20 nm)/HIM(175 nm)/HTM3(20 nm)/H1:SEB(5%)(20 nm)/ETM:LiQ(50%)(30 nm)/LiQ(1 nm) is produced. In the comparative experiment, HTM3 is replaced by HTMv3. The component comprising the inventive substance in the EBL achieves an external quantum efficiency at 10 mA/cm² of 7.3%. The component having the comparative substance in the same functional layer achieves only 7.0%.

Example 4

Finally, the compounds HTM4 und HTMv4 are also tested in a singlet blue stack: HIM:F4TCNQ(5%)(20 nm)/HIM(175 nm)/HTM4(20 nm)/H1:SEB(5%)(20 nm)/ETM:LiQ(50%)(30 nm)/LiQ(1 nm). In the comparative test, rather than HTM4, HTMv4 is introduced into the EBL. The inventive substance shows an external quantum efficiency at 10 mA/cm² of 7.5%. The comparative compound achieves only 7.2% EQE at 10 mA/cm².

The invention claimed is:
1. A compound of the formula (I)

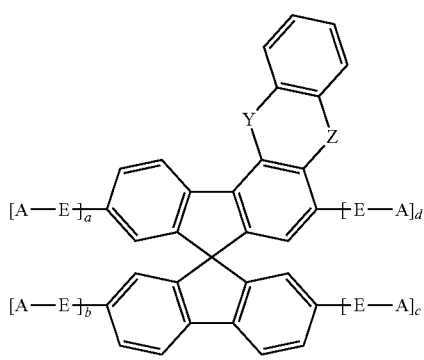

Formula (I)

which is optionally substituted at one or more positions shown as unsubstituted in the base structure of formula (I) by one R¹ radical each; and
which has the following definitions of the variables:
Y is selected from a single bond, O, S and Se;
Z is selected from O, S and Se;
E is the same or different at each instance and is a single bond or an aromatic or heteroaromatic ring system which has 6 to 30 aromatic ring atoms and is optionally substituted by one or more R² radicals;
A is the same or different at each instance and is a group of the formula (A1), (A2) or (A3) which is bonded via the bond marked with #;

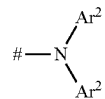

Formula (A1)

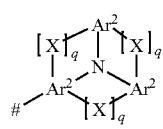

Formula (A2)

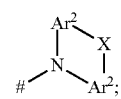

Formula (A3)

wherein
N is a nitrogen atom,
Ar² is the same or different at each instance and is an aromatic or heteroaromatic ring system which has 6 to 30 aromatic ring atoms and is optionally substituted by one or more R² radicals;
X is the same or different at each instance and is a single bond or a group selected from BR², C(R²)₂, Si(R²)₂, C=O, O, S, S=O, SO₂, NR², PR² and P(=O)R²;
R¹ is the same or different at each instance and is selected from H, D, F, C(=O)R³, CN, Si(R³)₃, P(=O)(R³)₂, OR³, S(=O)R³, S(=O)₂R³, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more R¹ radicals is optionally joined to one another and optionally forms a ring; where the alkyl, alkoxy, alkenyl and alkynyl groups mentioned and the aromatic ring systems and heteroaromatic ring systems mentioned optionally each is substituted by one or more R³ radicals; and where one or more CH₂ groups in the alkyl, alkoxy, alkenyl and alkynyl groups mentioned is optionally replaced by —R³C=CR³—, —C≡C—, Si(R³)₂, C=O, C=NR³, —C(=O)O—, —C(=O)NR³—, NR³, P(=O)(R³), —O—, —S—, SO or SO₂;
R² is the same or different at each instance and is selected from H, D, F, C(=O)R³, CN, Si(R³)₃, N(R³)₂, P(=O)(R³)₂, OR³, S(=O)R³, S(=O)₂R³, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^2$ radicals is optionally joined to one another and optionally forms a ring; where the alkyl, alkoxy, alkenyl and alkynyl groups mentioned and the aromatic ring systems and heteroaromatic ring systems mentioned optionally each is substituted by one or more $R^3$ radicals; and where one or more $CH_2$ groups in the alkyl, alkoxy, alkenyl and alkynyl groups mentioned is optionally replaced by —$R^3C$=$CR^3$—, —C≡C—, $Si(R^3)_2$, C=O, C=$NR^3$, —C(=O)$NR_3$—, $NR^3$, P(=O)($R^3$), —O—, —S—, SO or $SO_2$;

$R^3$ is the same or different at each instance and is selected from H, D, F, C(=O)$R^4$, CN, Si($R^4$)$_3$, N($R^4$)$_2$, P(=O)($R^4$)$_2$, $OR^4$, S(=O)$R^4$, S(=O)$_2R^4$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^1$ or $R^2$ radicals is optionally joined to one another and optionally forms a ring; where the alkyl, alkoxy, alkenyl and alkynyl groups mentioned and the aromatic ring systems and heteroaromatic ring systems mentioned optionally each is substituted by one or more $R^4$ radicals; and where one or more $CH_2$ groups in the alkyl, alkoxy, alkenyl and alkynyl groups mentioned is optionally replaced by —$R^4C$=$CR^4$—, —C≡C—, $Si(R^4)_2$, C=O, C=$NR^4$, —C(=O)O—, —C(=O)$NR_4$—, $NR^4$, P(=O)($R^4$), —O—, —S—, SO or $SO_2$;

$R^4$ is the same or different at each instance and is selected from H, D, F, CN, alkyl groups having 1 to 20 carbon atoms, aromatic ring systems having 6 to 40 aromatic ring atoms and heteroaromatic ring systems having 5 to 40 aromatic ring atoms; where two or more $R^4$ radicals is optionally joined to one another and optionally forms a ring; and where the alkyl groups, aromatic ring systems and heteroaromatic ring systems mentioned is optionally substituted by F or CN;

q is the same or different at each instance and is 0 or 1, where at least one q in formula (A2) is 1;

a, b, c, and d are the same or different at each instance and are 0 or 1, where at least one of the indices a, b, c and d is 1, and where, in the case that one or more of the indices a, b, c and d are 0, an $R^1$ group is attached at the position in question.

2. The compound according to claim 1, wherein Y is a single bond and Z is O or S.

3. The compound according to claim 1, wherein Y is O and S and Z is O or S.

4. The compound according to claim 1, wherein E is the same or different at each instance and is selected from a single bond and a divalent group derived from benzene, biphenyl, terphenyl, fluorene, spirobifluorene, indenofluorene, carbazole, dibenzofuran or dibenzothiophene, each optionally substituted by $R^2$ radicals, or a combination of two or more of these groups, where not more than 30 aromatic ring atoms are present in the E group.

5. The compound according to claim 1, wherein X is a single bond.

6. The compound according to claim 1, wherein A is the same or different at each instance and is a group of the formula (A-1) or (A-3).

7. The compound according to claim 1, wherein $Ar^2$ is the same or different at each instance and is selected from phenyl, biphenyl, terphenyl, fluorenyl, spirobifluorenyl, indenofluorenyl, naphthyl, phenanthrenyl, furanyl, benzofuranyl, dibenzofuranyl, thiophenyl, benzothiophenyl, dibenzothiophenyl, carbazolyl, indolocarbazolyl and indenocarbazolyl, each of which may be substituted by one or more $R^2$ radicals.

8. The compound according to claim 1, wherein $R^1$ is the same or different at each instance and is selected from H, F, CN, methyl, tert-butyl, phenyl, biphenyl, dibenzofuran, dibenzothiophene and carbazole.

9. The compound according to claim 1, wherein $R^1$ is H.

10. The compound according to claim 1, wherein exactly one of the indices a, b, c and d is 1 and the other indices are 0; or in that exactly two of the indices a, b, c and d are 1, and the other indices are 0.

11. The compound according to claim 1, wherein the index d is 0, and in that exactly one or exactly two of the indices a, b and c are 1.

12. The compound according to claim 1, wherein the compound corresponds to the following embodiment of formula (I-A)

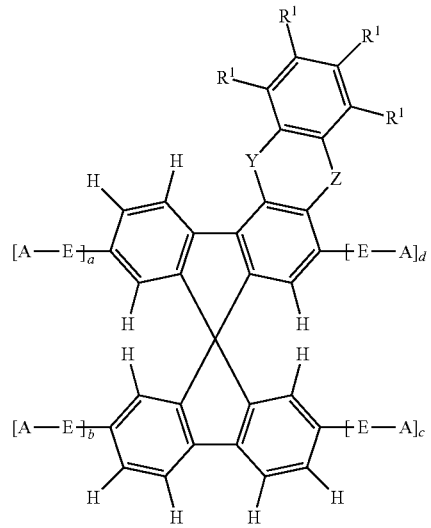

Formula (I-A)

wherein variables that occur are as defined as in claim 1.

13. A process for preparing the compound of the formula (I) according to claim 1, which comprises first preparing a spirobifluorene base skeleton and, in a later step, via an organometallic coupling reaction, an arylamino or carbazole group or an aryl or heteroaryl group substituted by an arylamino or carbazole group is introduced.

14. Oligomers, polymers or dendrimers containing one or more compounds of formula (I) according to claim 1, wherein the bond(s) to the polymer, oligomer or dendrimer may be localized at any desired positions substituted by $R^1$ or $R^2$ in formula (I).

15. A formulation comprising at least one compound according to claim 1, and at least one solvent.

16. An electronic device comprising at least one compound according to claim 1.

17. The electronic device according to claim 16, wherein the device is an organic electroluminescent device comprising anode, cathode and at least one emitting layer, where at least one organic layer of the device, which may be an emitting layer, a hole transport layer or another layer, comprises the at least one compound.

18. The electronic device according to claim 17, wherein the at least one organic layer is selected from a hole transport layer and an emitting layer.

19. The electronic device according to claim 17, wherein the at least one organic layer is selected from an electron blocker layer, and an emitting layer comprising one or more phosphorescent emitters.

\* \* \* \* \*